(12) United States Patent
Marczyk et al.

(10) Patent No.: US 7,624,902 B2
(45) Date of Patent: Dec. 1, 2009

(54) SURGICAL STAPLING APPARATUS

(75) Inventors: Stanislaw Marczyk, Stratford, CT (US); Kenneth Cappola, Monroe, CT (US); Frank C. Maffei, Shelton, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 12/200,004

(22) Filed: Aug. 28, 2008

(65) Prior Publication Data

US 2009/0057370 A1 Mar. 5, 2009

Related U.S. Application Data

(63) Continuation-in-part of application No. 11/974,638, filed on Oct. 15, 2007, now Pat. No. 7,515,993.

(60) Provisional application No. 60/967,169, filed on Aug. 31, 2007.

(51) Int. Cl.
*A61B 17/068* (2006.01)
(52) U.S. Cl. .................... 227/175.1; 227/19; 227/176.1
(58) Field of Classification Search .................. 227/19, 227/175.1, 176.1, 180.1, 178.1; 606/139, 606/219
See application file for complete search history.

(56) References Cited

U.S. PATENT DOCUMENTS

| | | | |
|---|---|---|---|
| 3,079,606 A | 3/1963 | Bobrov et al. |
| 3,490,675 A | 1/1970 | Green et al. |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |

(Continued)

FOREIGN PATENT DOCUMENTS

AU 5476586 9/1986

(Continued)

*Primary Examiner*—Scott A. Smith

(57) ABSTRACT

A surgical stapling device particularly suited for endoscopic procedures is described. The device includes a handle assembly and an elongated body extending distally from the handle assembly. The distal end of the elongated body is adapted to engage a disposable loading unit. A control rod having a proximal end operatively connected to the handle assembly includes a distal end extending through the elongated body. A control rod locking member is provided to prevent movement of the control rod until the disposable loading unit is fully secured to the elongated body of the stapling device.

14 Claims, 48 Drawing Sheets

U.S. PATENT DOCUMENTS

| | | |
|---|---|---|
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | deSalis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughetti et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A * | 5/1994 | Green et al. ............. 227/175.1 |
| 5,318,221 A | 6/1994 | Green et al. |
| 5,326,013 A * | 7/1994 | Green et al. ............. 227/176.1 |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A * | 12/1996 | Conlon et al. ............. 227/176.1 |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |

| Patent | Date | Inventor |
|---|---|---|
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A * | 8/1998 | Oberlin et al. ............ 227/176.1 |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,827,776 A * | 10/1998 | Bandyopadhyay et al. .. 438/624 |
| 5,829,662 A | 11/1998 | Allen et al. |
| 5,833,695 A | 11/1998 | Yoon |
| 5,836,147 A | 11/1998 | Schnipke |
| 5,855,311 A * | 1/1999 | Hamblin et al. ........... 227/176.1 |
| 5,862,972 A | 1/1999 | Green et al. |
| 5,865,361 A * | 2/1999 | Milliman et al. ......... 227/176.1 |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A * | 1/2000 | Johnson et al. ........... 227/176.1 |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 * | 6/2001 | Milliman et al. ......... 227/175.1 |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| 6,644,532 B2 | 11/2003 | Green et al. |
| 6,656,193 B2 | 12/2003 | Grant et al. |
| 6,669,073 B2 * | 12/2003 | Milliman et al. ......... 227/175.2 |
| 6,681,978 B2 | 1/2004 | Geiste et al. |
| 6,698,643 B2 | 3/2004 | Whitman |
| 6,716,232 B1 | 4/2004 | Vidal et al. |

| | | |
|---|---|---|
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,724 B2 | 11/2007 | Green et al. |
| 7,296,772 B2 | 11/2007 | Wang |
| 7,300,444 B1 | 11/2007 | Nielsen et al. |
| 7,303,108 B2 | 12/2007 | Shelton, IV |
| 7,308,998 B2 | 12/2007 | Mastri et al. |
| 7,328,828 B2 | 2/2008 | Ortiz et al. |
| 7,328,829 B2 | 2/2008 | Arad et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,399,310 B2 | 7/2008 | Edoga et al. |
| 7,401,720 B1 | 7/2008 | Durrani |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,419,495 B2 | 11/2008 | Menn et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,510,107 B2 | 3/2009 | Timm et al. |
| 7,513,408 B2 | 4/2009 | Shelton, IV et al. |
| 7,517,356 B2 | 4/2009 | Heinrich |
| 2002/0004498 A1 | 1/2002 | Doherty |
| 2002/0009193 A1 | 1/2002 | Deguchi |
| 2002/0018323 A1 | 2/2002 | Li |
| 2002/0032948 A1 | 3/2002 | Ahn |
| 2002/0036748 A1 | 3/2002 | Chapoy |
| 2002/0045442 A1 | 4/2002 | Silen et al. |
| 2002/0069595 A1 | 6/2002 | Knudson et al. |
| 2002/0084304 A1 | 7/2002 | Whitman |
| 2002/0111621 A1 | 8/2002 | Wallace et al. |
| 2002/0143346 A1 | 10/2002 | McGuckin, Jr. et al. |
| 2002/0177843 A1 | 11/2002 | Anderson et al. |
| 2002/0188294 A1 | 12/2002 | Couture et al. |
| 2002/0190093 A1 | 12/2002 | Fenton, Jr. |
| 2003/0009193 A1 | 1/2003 | Corsaro |
| 2003/0105476 A1 | 6/2003 | Sancoff et al. |
| 2003/0132268 A1 | 7/2003 | Whitman |
| 2004/0004105 A1 | 1/2004 | Jankowski |
| 2004/0007608 A1 | 1/2004 | Ehrenfels et al. |
| 2004/0050902 A1 | 3/2004 | Green |
| 2004/0093029 A1 | 5/2004 | Zubik et al. |
| 2004/0094597 A1 | 5/2004 | Whitman |
| 2004/0108357 A1 | 6/2004 | Milliman |
| 2004/0149802 A1 | 8/2004 | Whitman |
| 2004/0173659 A1 | 9/2004 | Green |
| 2004/0199180 A1 | 10/2004 | Knodel et al. |
| 2004/0199181 A1 | 10/2004 | Knodel et al. |
| 2004/0232199 A1 | 11/2004 | Shelton, IV et al. |

| Publication No. | Date | Inventor |
|---|---|---|
| 2004/0232200 A1 | 11/2004 | Shelton, IV et al. |
| 2004/0232201 A1 | 11/2004 | Wenchell |
| 2004/0243151 A1 | 12/2004 | Demmy |
| 2004/0267310 A1 | 12/2004 | Racenet |
| 2004/0267311 A1 | 12/2004 | Viola et al. |
| 2005/0006429 A1 | 1/2005 | Wales |
| 2005/0006430 A1 | 1/2005 | Wales |
| 2005/0006431 A1 | 1/2005 | Shelton, IV et al. |
| 2005/0006432 A1 | 1/2005 | Racenet |
| 2005/0006433 A1 | 1/2005 | Milliman |
| 2005/0006434 A1 | 1/2005 | Wales et al. |
| 2005/0023324 A1 | 2/2005 | Doll et al. |
| 2005/0023325 A1 | 2/2005 | Gresham |
| 2005/0067457 A1 | 3/2005 | Shelton |
| 2005/0067458 A1 | 3/2005 | Swayze et al. |
| 2005/0067459 A1 | 3/2005 | Swayze et al. |
| 2005/0067460 A1 | 3/2005 | Milliman |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0082336 A1 | 4/2005 | Ivanko |
| 2005/0103819 A1 | 5/2005 | Racenet |
| 2005/0119669 A1 | 6/2005 | Demmy |
| 2005/0127131 A1 | 6/2005 | Mastri |
| 2005/0145671 A1 | 7/2005 | Viola |
| 2005/0159778 A1 | 7/2005 | Heinrich et al. |
| 2005/0165415 A1 | 7/2005 | Wales |
| 2005/0173490 A1 | 8/2005 | Shelton, IV |
| 2005/0178813 A1 | 8/2005 | Swayze et al. |
| 2005/0184121 A1 | 8/2005 | Heinrich |
| 2005/0184123 A1 | 8/2005 | Scirica et al. |
| 2005/0184124 A1 | 8/2005 | Scirica et al. |
| 2005/0184125 A1 | 8/2005 | Marczyk |
| 2005/0184126 A1 | 8/2005 | Green et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0230453 A1 | 10/2005 | Viola |
| 2005/0263562 A1 | 12/2005 | Shelton et al. |
| 2005/0279804 A1 | 12/2005 | Scirica et al. |
| 2006/0000867 A1 | 1/2006 | Shelton, IV et al. |
| 2006/0000868 A1 | 1/2006 | Shelton, IV et al. |
| 2006/0011699 A1 | 1/2006 | Olson et al. |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0043147 A1 | 3/2006 | Mastri et al. |
| 2006/0049229 A1 | 3/2006 | Milliman et al. |
| 2006/0049230 A1 | 3/2006 | Shelton, IV et al. |
| 2006/0060630 A1 | 3/2006 | Shelton, IV et al. |
| 2006/0081678 A1 | 4/2006 | Ehrenfels et al. |
| 2006/0097026 A1 | 5/2006 | Shelton, IV |
| 2006/0124688 A1 | 6/2006 | Racenet et al. |
| 2006/0124689 A1 | 6/2006 | Arad et al. |
| 2006/0138193 A1 | 6/2006 | Viola et al. |
| 2006/0138194 A1 | 6/2006 | Viola et al. |
| 2006/0151567 A1 | 7/2006 | Roy |
| 2006/0151568 A1 | 7/2006 | Weller et al. |
| 2006/0151569 A1 | 7/2006 | Ehrenfels et al. |
| 2006/0175375 A1 | 8/2006 | Shelton, IV et al. |
| 2006/0180634 A1 | 8/2006 | Shelton, IV et al. |
| 2006/0201990 A1 | 9/2006 | Mastri et al. |
| 2006/0201991 A1 | 9/2006 | Mastri et al. |
| 2006/0226195 A1 | 10/2006 | Scirica et al. |
| 2006/0226196 A1 | 10/2006 | Hueil et al. |
| 2006/0255090 A1 | 11/2006 | Milliman et al. |
| 2006/0278680 A1 | 12/2006 | Viola et al. |
| 2006/0278681 A1 | 12/2006 | Viola et al. |
| 2006/0289600 A1 | 12/2006 | Wales et al. |
| 2006/0289602 A1 | 12/2006 | Wales et al. |
| 2007/0023477 A1 | 2/2007 | Whitman et al. |
| 2007/0027469 A1 | 2/2007 | Smith et al. |
| 2007/0034669 A1 | 2/2007 | de la Torre et al. |
| 2007/0034670 A1 | 2/2007 | Racenet et al. |
| 2007/0045379 A1 | 3/2007 | Shelton, IV |
| 2007/0045380 A1 | 3/2007 | Mastri et al. |
| 2007/0068989 A1 | 3/2007 | Shelton, IV |
| 2007/0068990 A1 | 3/2007 | Shelton, IV et al. |
| 2007/0073340 A1 | 3/2007 | Shelton, IV et al. |
| 2007/0073341 A1 | 3/2007 | Smith et al. |
| 2007/0075114 A1 | 4/2007 | Shelton, IV et al. |
| 2007/0075115 A1 | 4/2007 | Olson et al. |
| 2007/0075116 A1 | 4/2007 | Whitman |
| 2007/0083233 A1 | 4/2007 | Ortiz et al. |
| 2007/0083234 A1 | 4/2007 | Shelton, IV et al. |
| 2007/0084896 A1 | 4/2007 | Doll et al. |
| 2007/0084897 A1 | 4/2007 | Shelton, IV et al. |
| 2007/0084898 A1 | 4/2007 | Scirica |
| 2007/0084899 A1 | 4/2007 | Taylor |
| 2007/0102472 A1 | 5/2007 | Shelton, IV |
| 2007/0102473 A1 | 5/2007 | Shelton, IV |
| 2007/0102474 A1 | 5/2007 | Shelton, IV |
| 2007/0102475 A1 | 5/2007 | Ortiz et al. |
| 2007/0102476 A1 | 5/2007 | Shelton, IV |
| 2007/0106317 A1 | 5/2007 | Shelton, IV |
| 2007/0108252 A1 | 5/2007 | Racenet et al. |
| 2007/0114261 A1 | 5/2007 | Ortiz et al. |
| 2007/0114262 A1 | 5/2007 | Mastri et al. |
| 2007/0119900 A1 | 5/2007 | Ehrenfels et al. |
| 2007/0119901 A1 | 5/2007 | Ehrenfels et al. |
| 2007/0125826 A1 | 6/2007 | Shelton, IV |
| 2007/0125827 A1 | 6/2007 | Viola |
| 2007/0125828 A1 | 6/2007 | Rethy et al. |
| 2007/0145095 A1 | 6/2007 | Heinrich et al. |
| 2007/0145096 A1 | 6/2007 | Viola et al. |
| 2007/0152014 A1 | 7/2007 | Gillum et al. |
| 2007/0158385 A1 | 7/2007 | Hueil et al. |
| 2007/0170225 A1 | 7/2007 | Shelton, IV et al. |
| 2007/0175947 A1 | 8/2007 | Ortiz et al. |
| 2007/0175948 A1 | 8/2007 | Scirica et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175954 A1 | 8/2007 | Viola |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179528 A1 | 8/2007 | Soltz et al. |
| 2007/0187453 A1 | 8/2007 | Smith et al. |
| 2007/0187454 A1 | 8/2007 | Scirica |
| 2007/0187455 A1 | 8/2007 | Demmy et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0278277 A1 | 12/2007 | Wixey et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |

| | | | | | | |
|---|---|---|---|---|---|---|
| 2008/0048002 A1 | 2/2008 | Smith et al. | | 2009/0105535 A1 | 4/2009 | Green |
| 2008/0078800 A1 | 4/2008 | Hess et al. | | 2009/0108048 A1 | 4/2009 | Zemlok et al. |
| 2008/0078801 A1 | 4/2008 | Shelton et al. | | 2009/0108049 A1 | 4/2009 | Roy |
| 2008/0078802 A1 | 4/2008 | Hess et al. | | 2009/0114699 A1 | 5/2009 | Viola |
| 2008/0078803 A1 | 4/2008 | Shelton et al. | | 2009/0114700 A1 | 5/2009 | Marczyk |
| 2008/0078804 A1 | 4/2008 | Shelton et al. | | 2009/0114701 A1 | 5/2009 | Zemlok et al. |
| 2008/0078805 A1 | 4/2008 | Omaits et al. | | | | |
| 2008/0078806 A1 | 4/2008 | Omaits et al. | | | | |
| 2008/0078807 A1 | 4/2008 | Hess et al. | | | | |

FOREIGN PATENT DOCUMENTS

| | | |
|---|---|---|
| DE | 2744824 | 4/1978 |
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0760230 | 3/1997 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| GB | 2165559 | 4/1986 |
| JP | 51-149985 | 5/1975 |
| SU | 728848 | 5/1977 |
| SU | 659146 | 4/1979 |
| SU | 980703 | 12/1982 |
| SU | 990220 | 1/1983 |
| WO | WO8302247 | 7/1983 |

| | | | |
|---|---|---|---|
| 2008/0078808 A1 | 4/2008 | Hess et al. | |
| 2008/0110958 A1 | 5/2008 | McKenna et al. | |
| 2008/0110961 A1 | 5/2008 | Voegele et al. | |
| 2008/0125812 A1 | 5/2008 | Zubik et al. | |
| 2008/0149685 A1 | 6/2008 | Smith et al. | |
| 2008/0164296 A1 | 7/2008 | Shelton et al. | |
| 2008/0169327 A1 | 7/2008 | Shelton et al. | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0210738 A1 | 9/2008 | Shelton et al. | |
| 2008/0237296 A1 | 10/2008 | Boudreaux et al. | |
| 2008/0237298 A1 | 10/2008 | Schall et al. | |
| 2008/0277447 A1 | 11/2008 | Smith et al. | |
| 2008/0283570 A1 | 11/2008 | Boyden et al. | |
| 2008/0283571 A1 | 11/2008 | Boyden et al. | |
| 2008/0283572 A1 | 11/2008 | Boyden et al. | |
| 2008/0283574 A1 | 11/2008 | Boyden et al. | |
| 2008/0283576 A1 | 11/2008 | Boyden et al. | |
| 2008/0283577 A1 | 11/2008 | Boyden et al. | |
| 2008/0287987 A1 | 11/2008 | Boyden et al. | |
| 2008/0296343 A1 | 12/2008 | Schall et al. | |
| 2008/0296344 A1 | 12/2008 | Cropper et al. | |
| 2008/0296345 A1 | 12/2008 | Shelton, IV et al. | |
| 2008/0296346 A1 | 12/2008 | Shelton, IV et al. | |
| 2008/0296347 A1 | 12/2008 | Shelton, IV et al. | |
| 2008/0302854 A1 | 12/2008 | Rethy et al. | |
| 2008/0308601 A1 | 12/2008 | Timm et al. | |
| 2008/0308602 A1 | 12/2008 | Timm et al. | |
| 2008/0308603 A1 | 12/2008 | Shelton, IV et al. | |
| 2008/0308604 A1 | 12/2008 | Timm et al. | |
| 2008/0308606 A1 | 12/2008 | Timm et al. | |
| 2008/0308607 A1 | 12/2008 | Timm et al. | |
| 2008/0314954 A1 | 12/2008 | Boudreaux | |
| 2008/0314955 A1 | 12/2008 | Boudreaux et al. | |
| 2008/0314957 A1 | 12/2008 | Boudreaux | |
| 2008/0314961 A1 | 12/2008 | Boudreaux et al. | |
| 2008/0314962 A1 | 12/2008 | Boudreaux | |
| 2009/0001121 A1 | 1/2009 | Hess et al. | |
| 2009/0001123 A1 | 1/2009 | Morgan et al. | |
| 2009/0001124 A1 | 1/2009 | Hess et al. | |
| 2009/0001125 A1 | 1/2009 | Hess et al. | |
| 2009/0001126 A1 | 1/2009 | Hess et al. | |
| 2009/0001130 A1 | 1/2009 | Hess et al. | |
| 2009/0005808 A1 | 1/2009 | Hess et al. | |
| 2009/0008424 A1 | 1/2009 | Green | |
| 2009/0050671 A1 | 2/2009 | Racenet et al. | |
| 2009/0057370 A1 | 3/2009 | Marczyk et al. | |
| 2009/0065549 A1 | 3/2009 | Viola | |
| 2009/0065550 A1 | 3/2009 | Green et al. | |
| 2009/0065551 A1 | 3/2009 | Green et al. | |
| 2009/0078738 A1 | 3/2009 | Racenet et al. | |
| 2009/0078739 A1 | 3/2009 | Viola | |
| 2009/0084826 A1 | 4/2009 | Shah et al. | |
| 2009/0090763 A1 | 4/2009 | Zemlok et al. | |
| 2009/0090764 A1 | 4/2009 | Viola | |
| 2009/0090765 A1 | 4/2009 | Blier et al. | |
| 2009/0090766 A1 | 4/2009 | Knodel | |
| 2009/0095790 A1 | 4/2009 | Whitman et al. | |
| 2009/0101692 A1 | 4/2009 | Whitman et al. | |
| 2009/0101694 A1 | 4/2009 | Marczyk | |

| WO | WO 89/10094 | 11/1989 |
| WO | WO9210976 | 7/1992 |
| WO | 9308754 | 5/1993 |
| WO | 9314706 | 8/1993 |

* cited by examiner

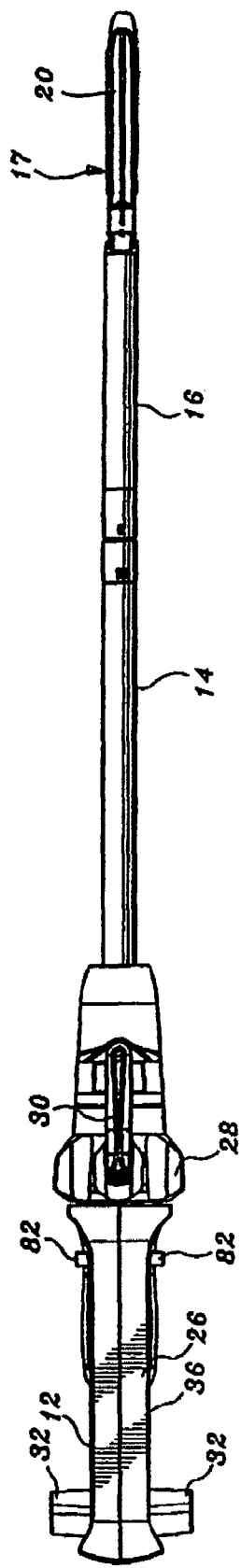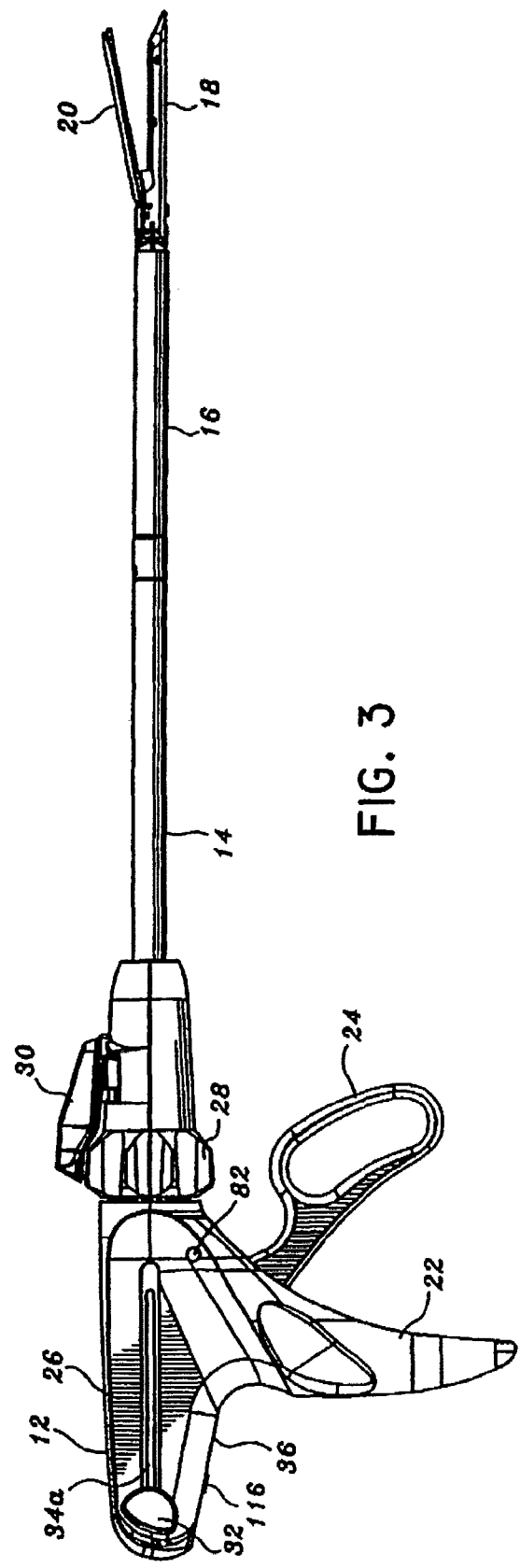
FIG. 2
FIG. 3

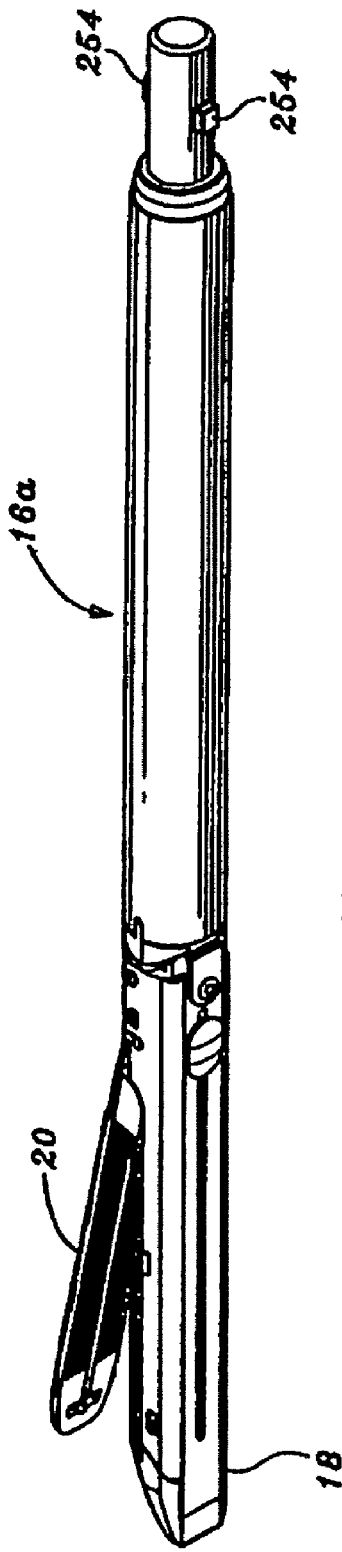
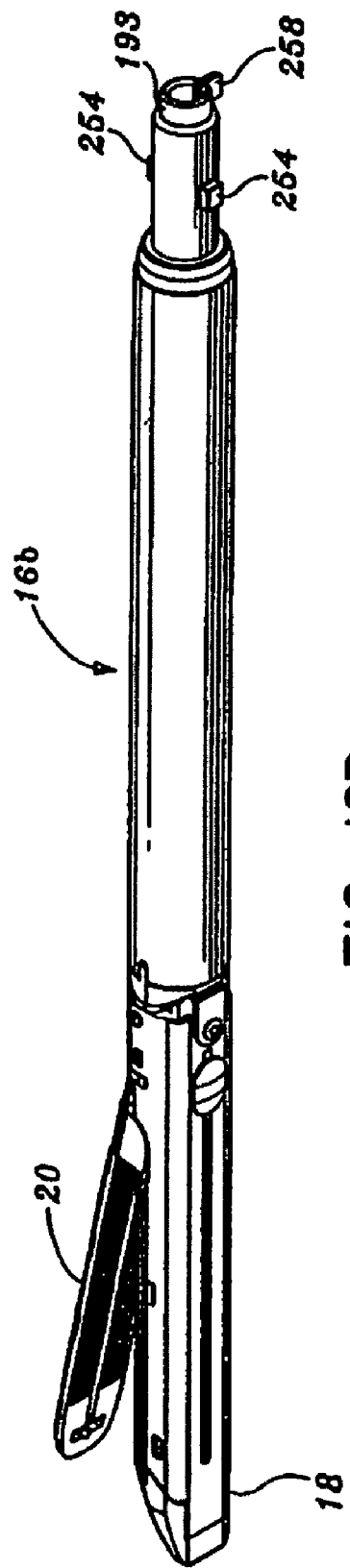

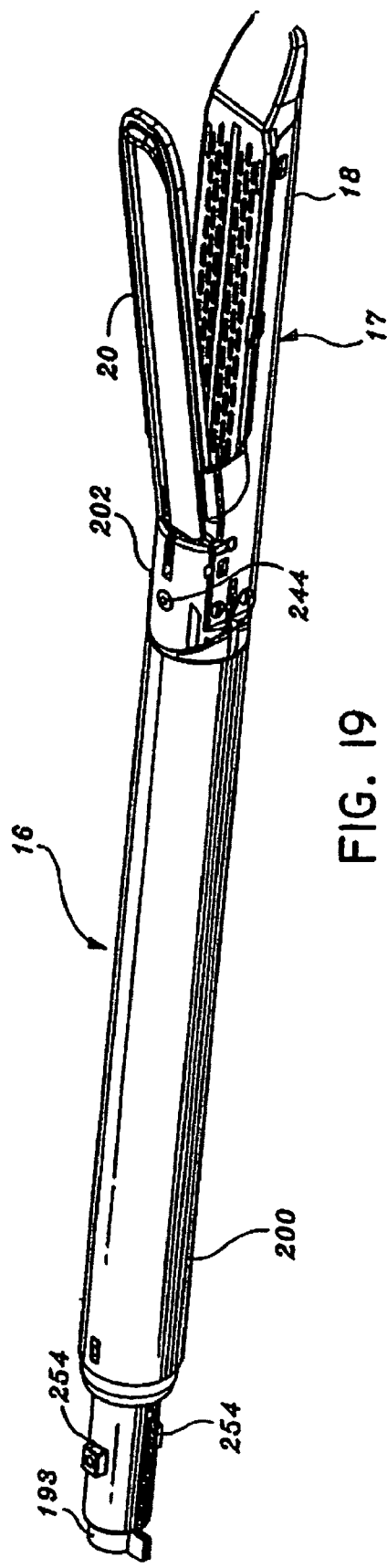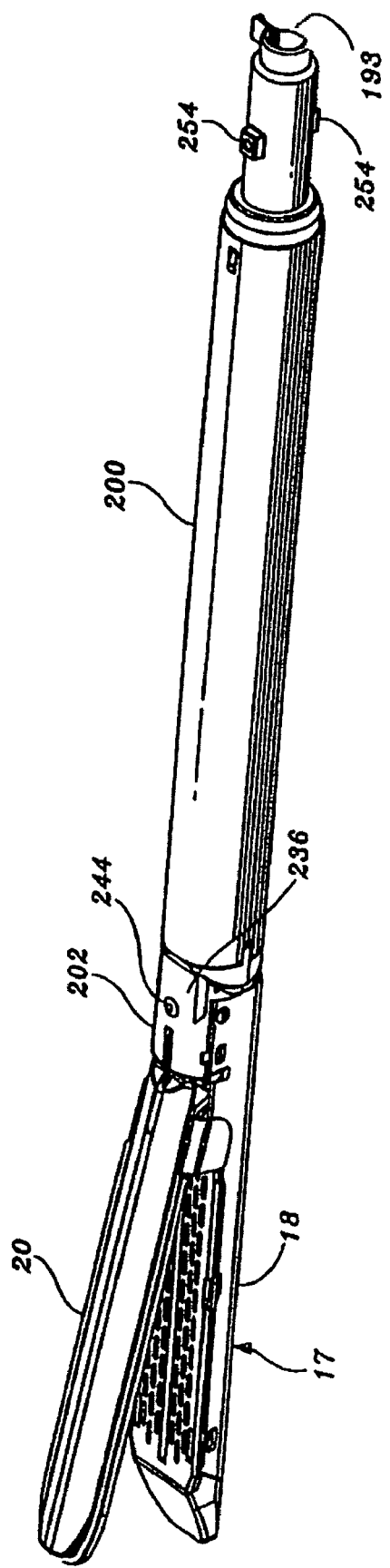

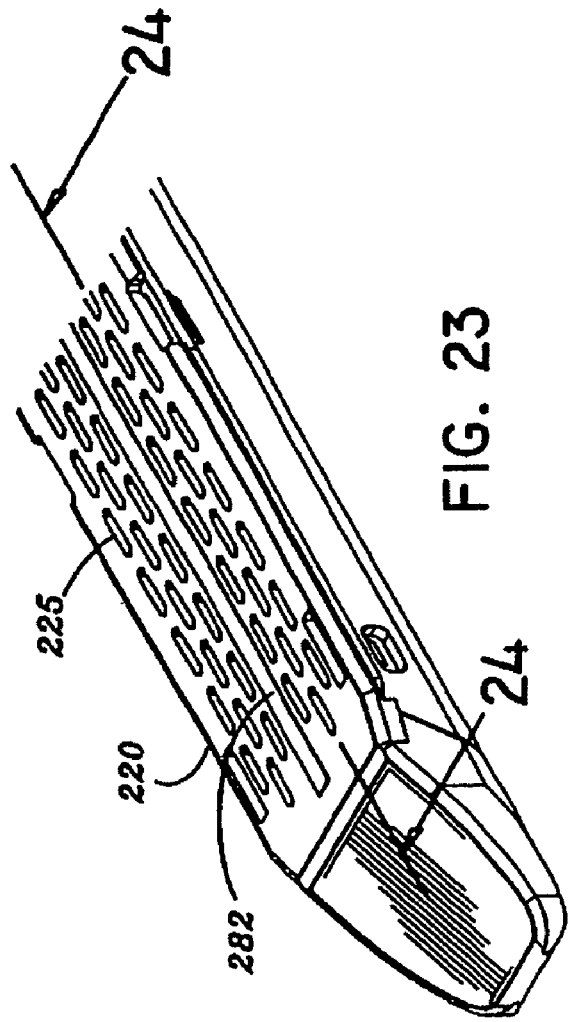
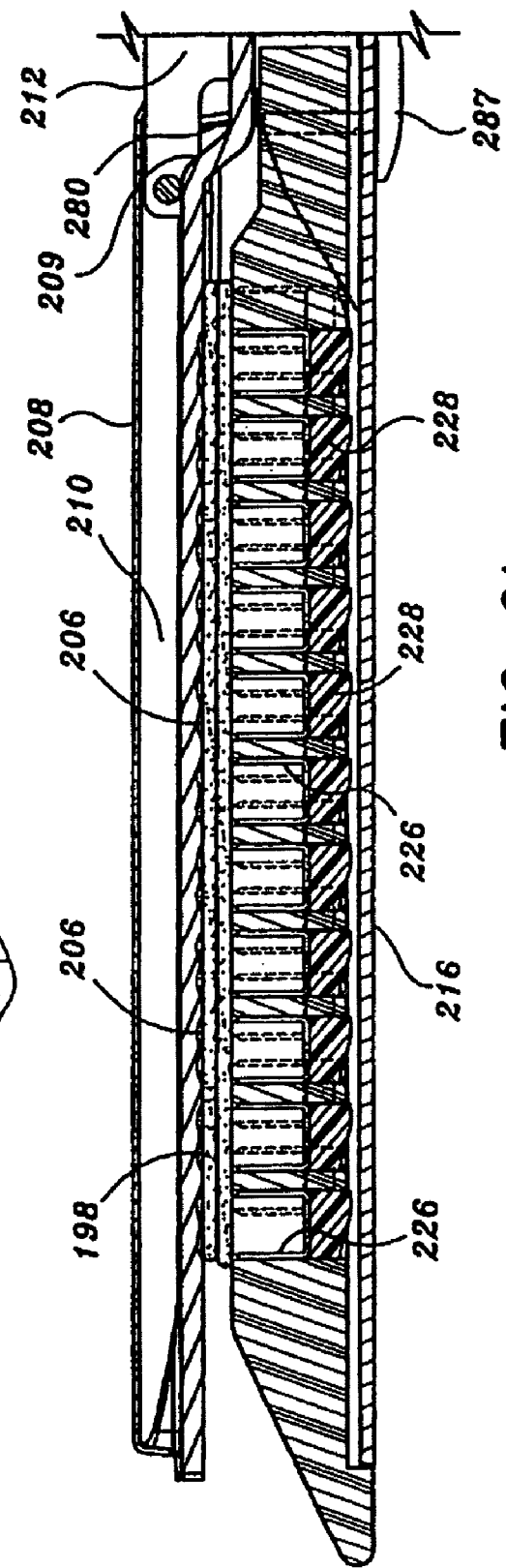
FIG. 23
FIG. 24

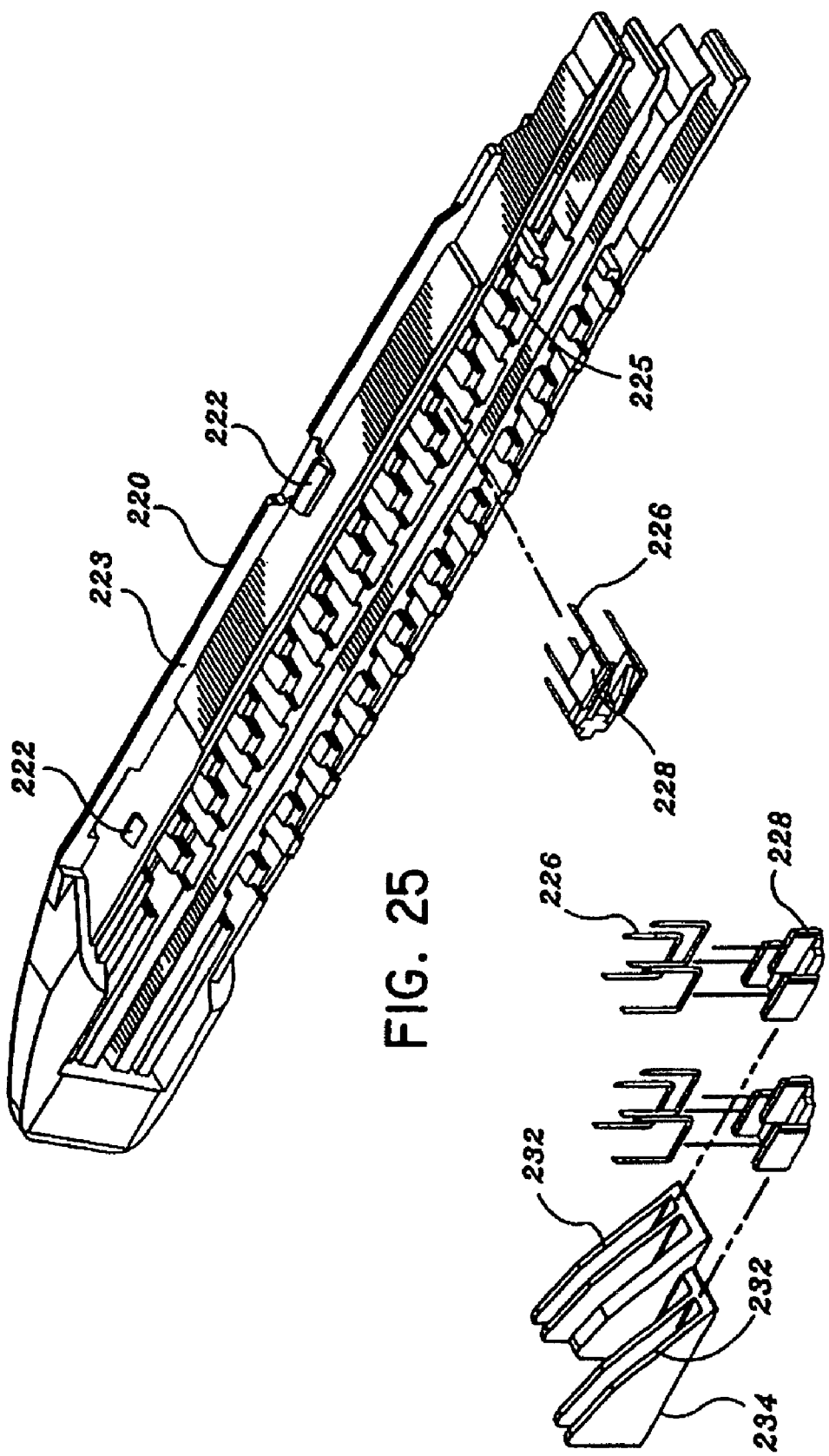

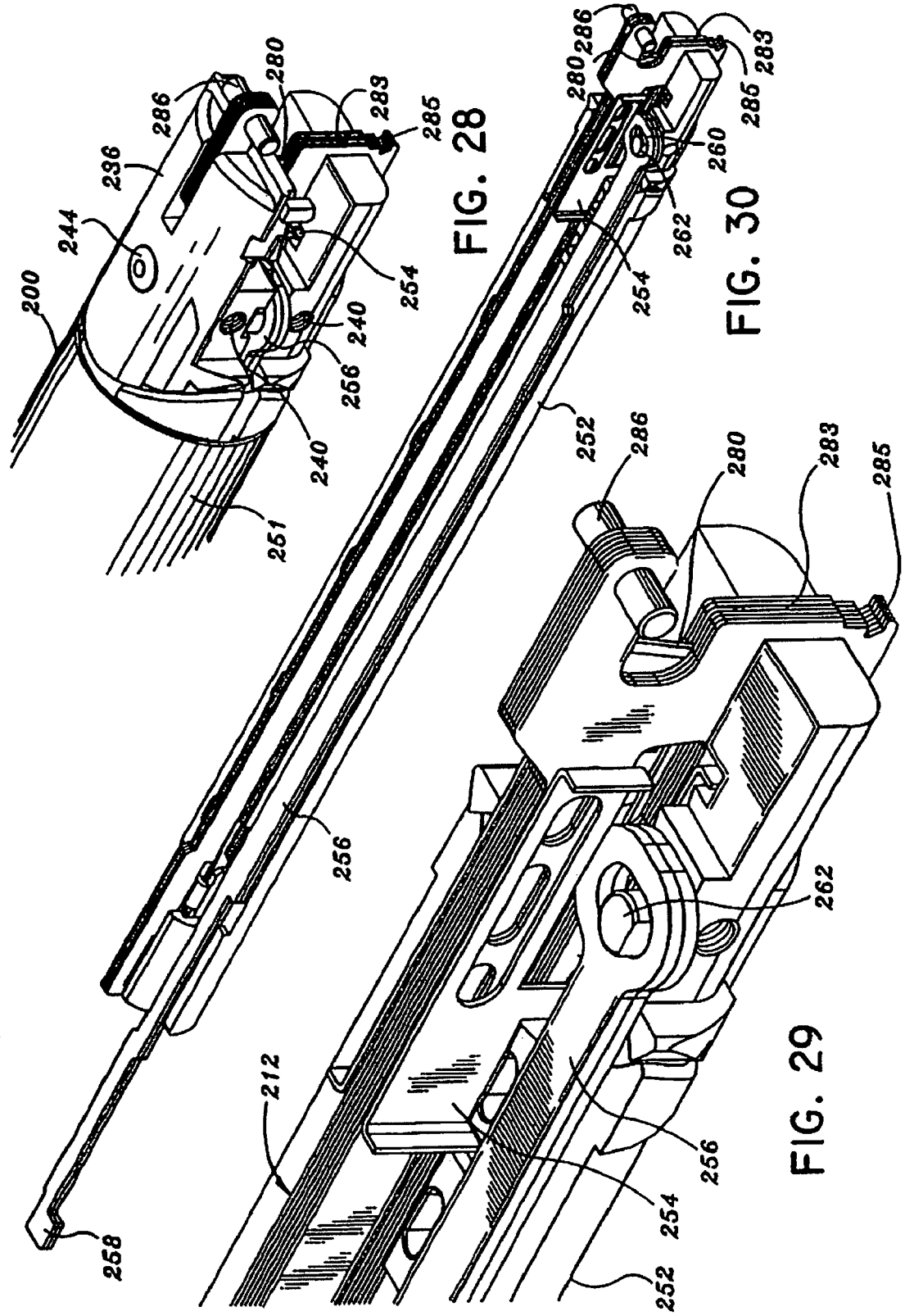

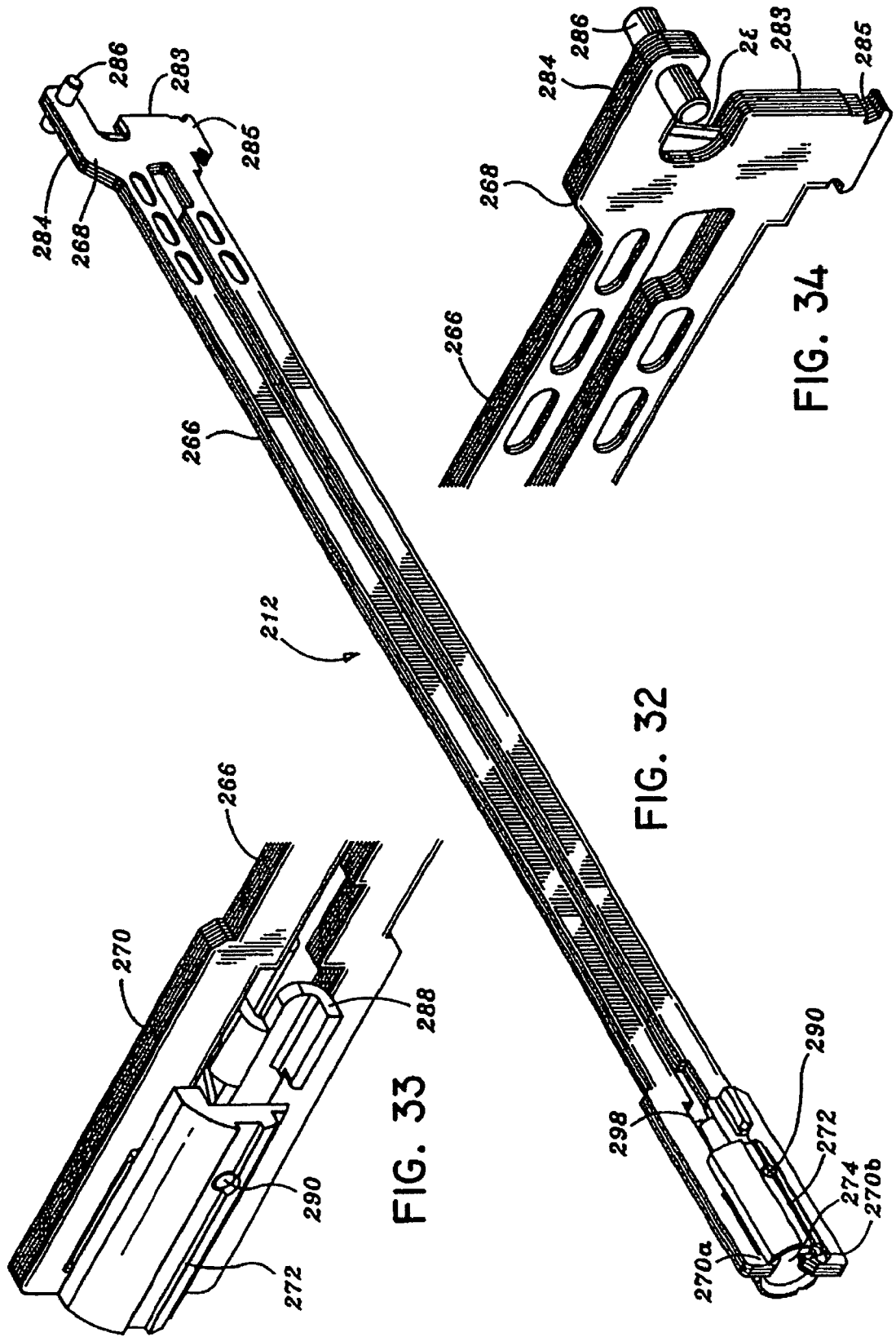

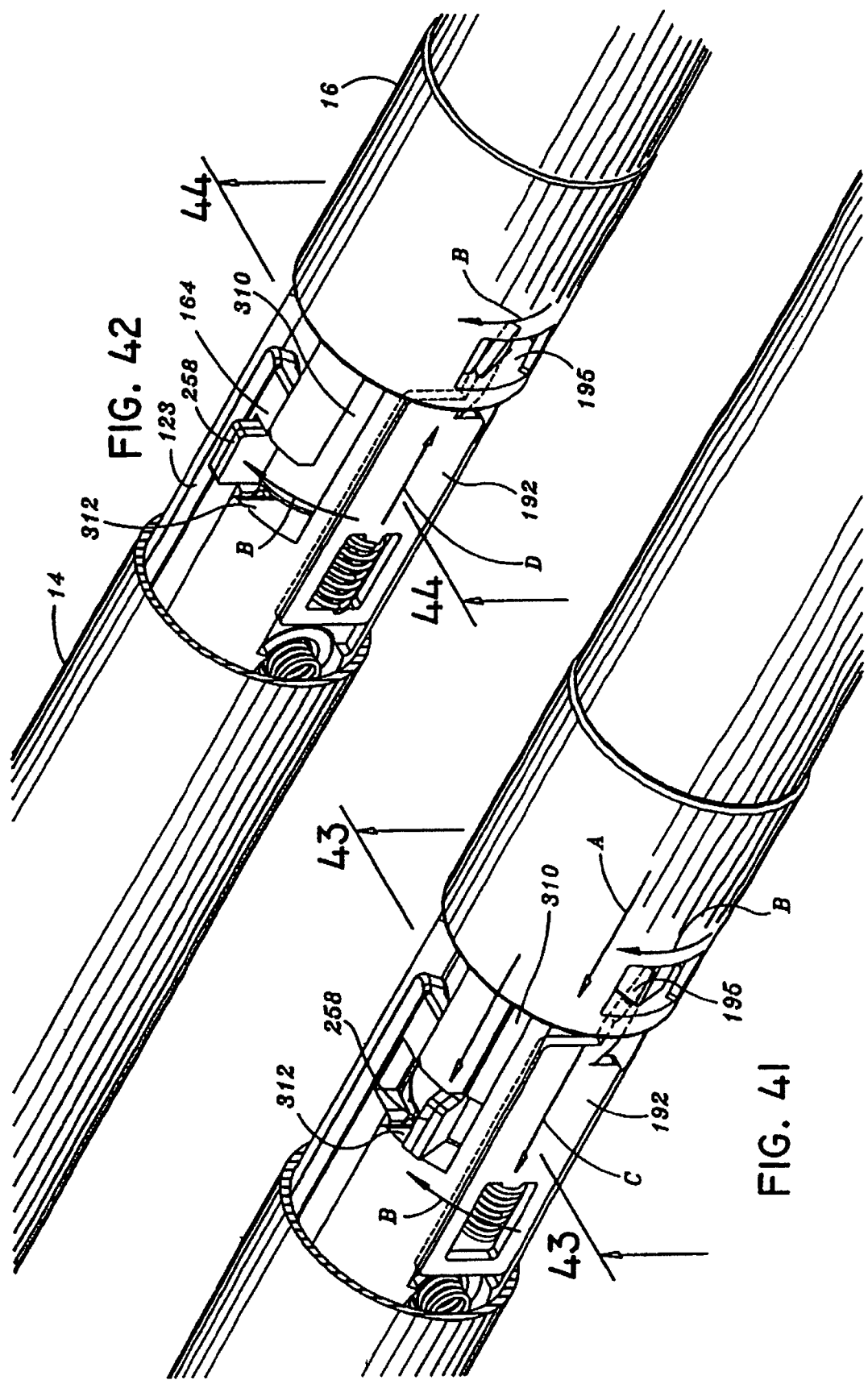

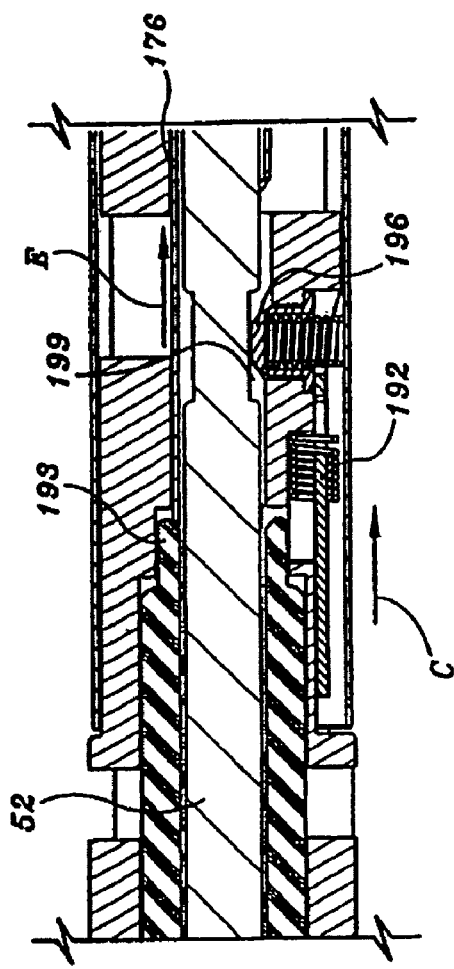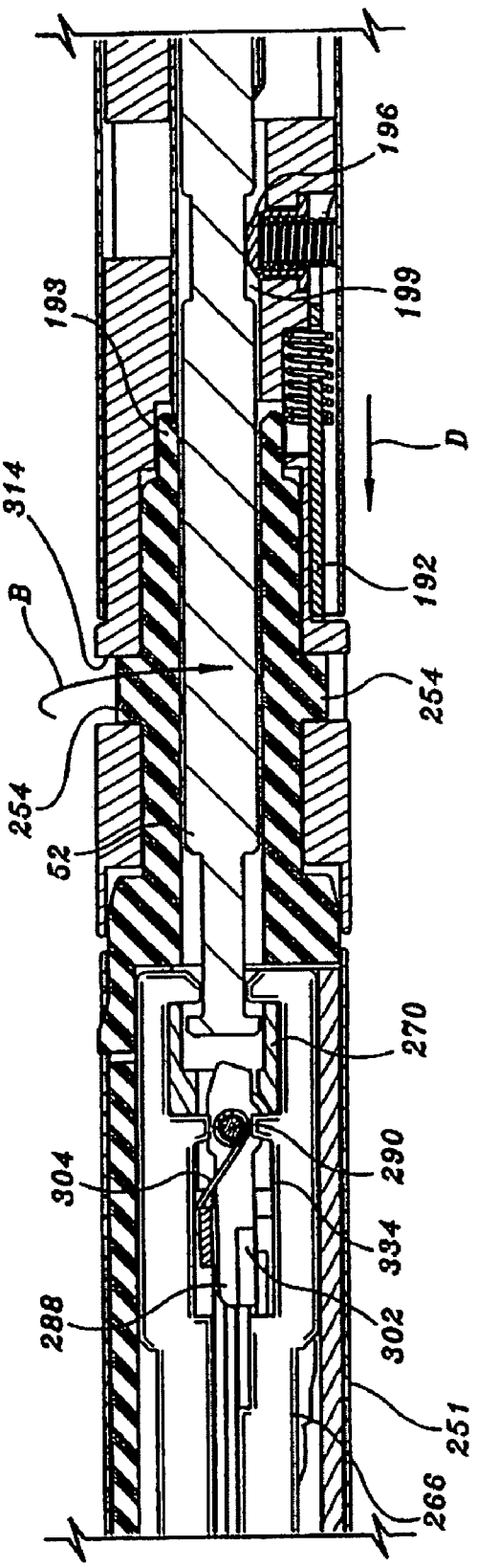

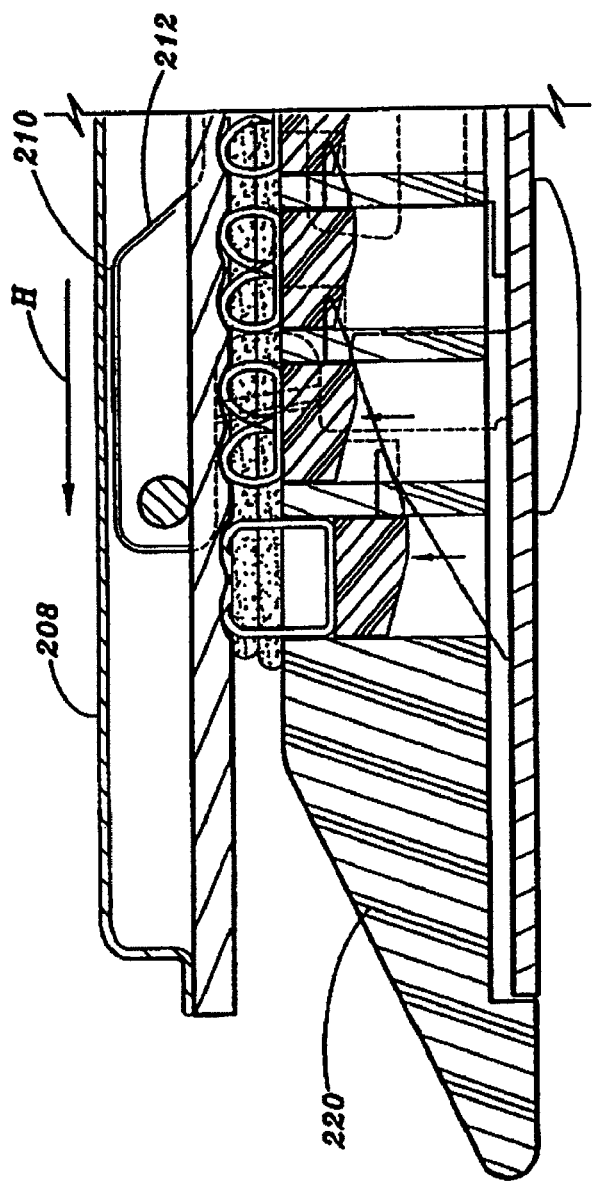
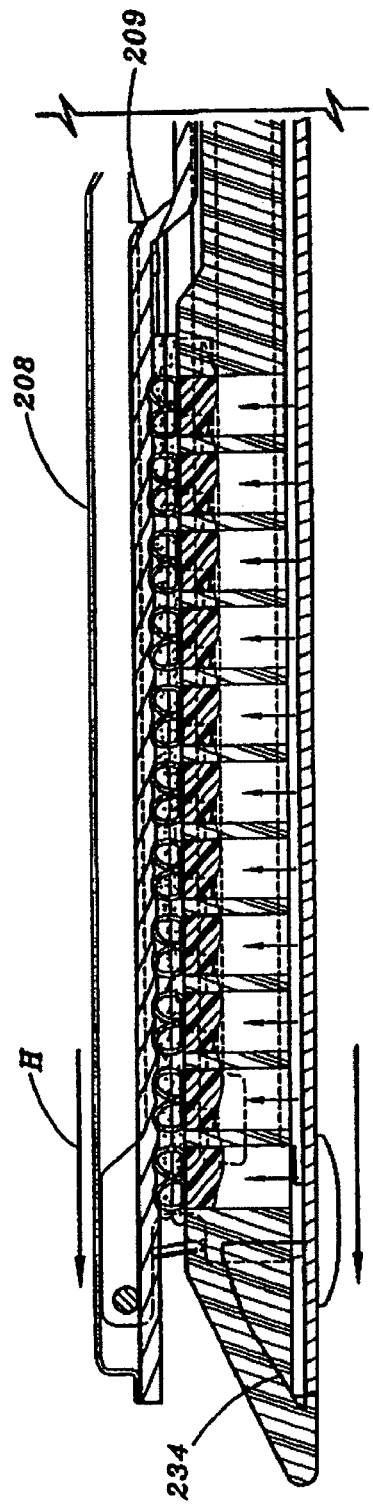
FIG. 51
FIG. 52

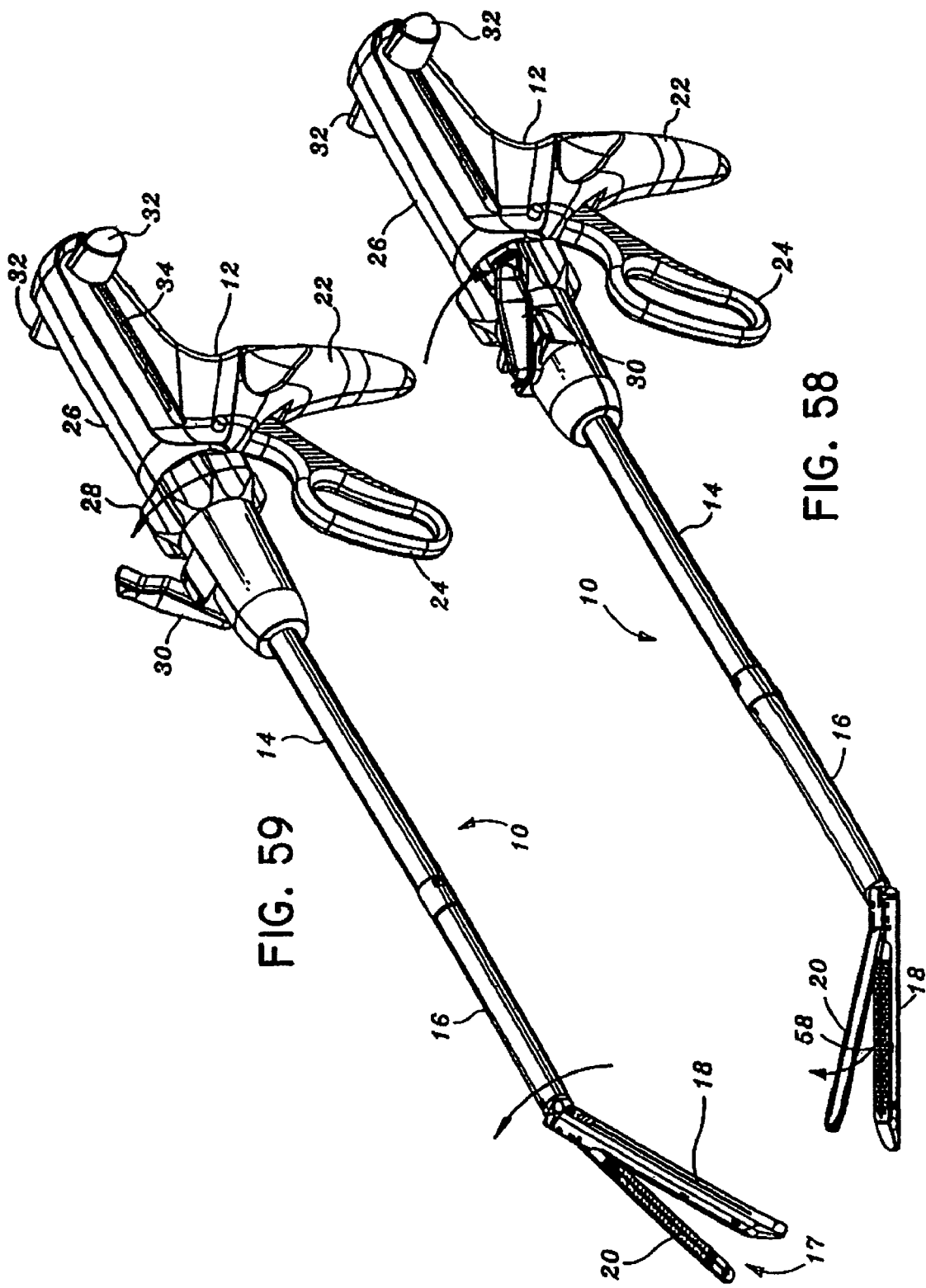

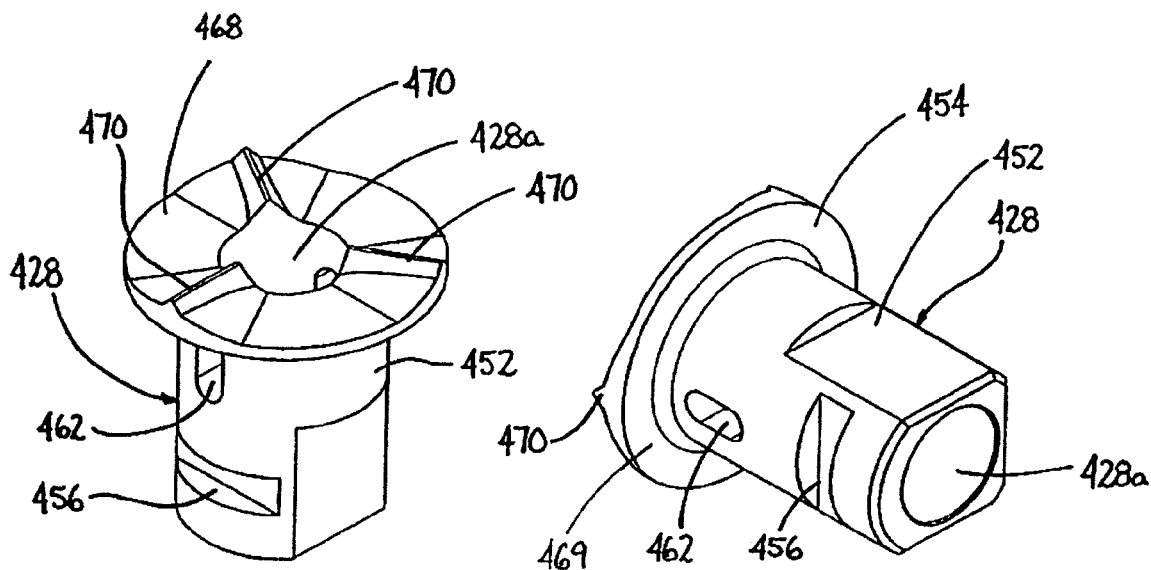
FIG. 68
FIG. 69
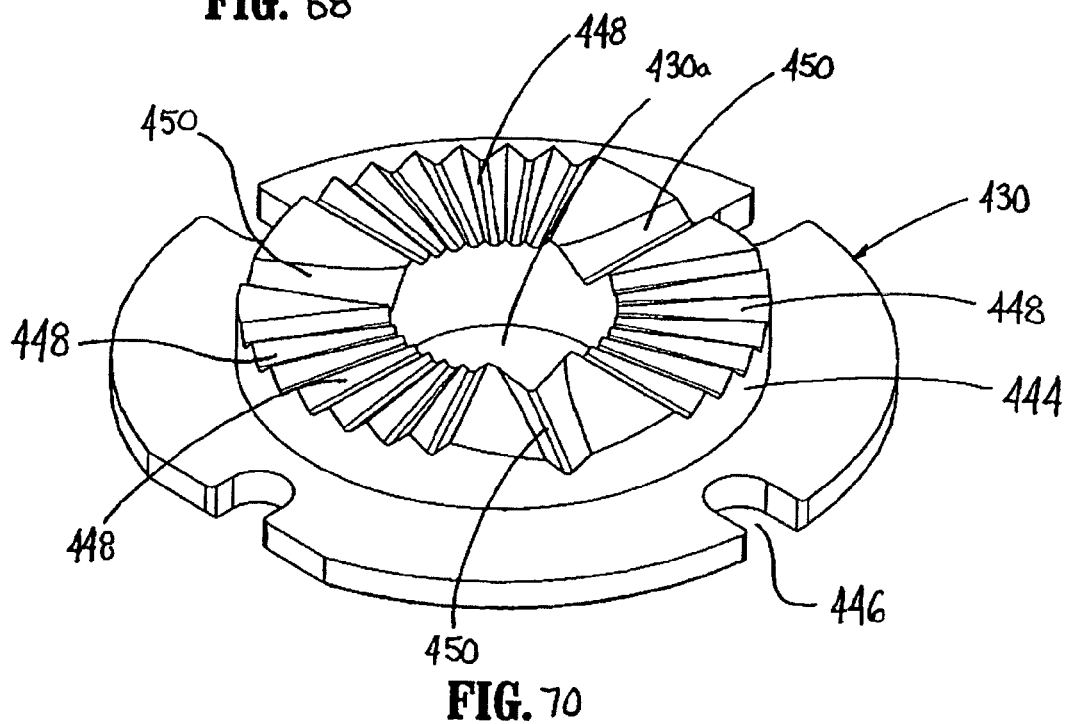
FIG. 70

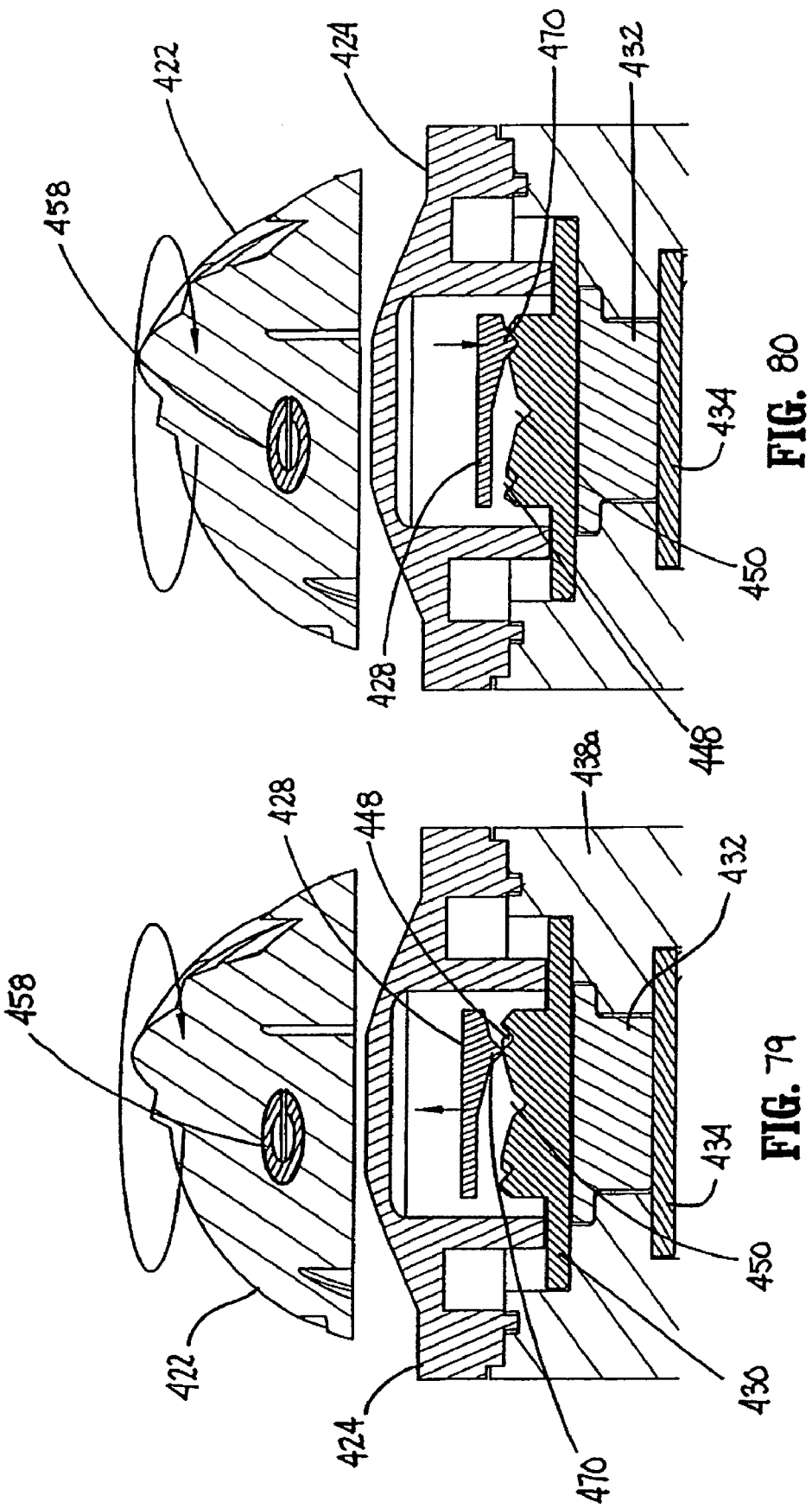

SURGICAL STAPLING APPARATUS

CROSS-REFERENCE TO RELATED APPLICATIONS

This application claims the benefit of U.S. Provisional Application Ser. No. 60/967,169, filed Aug. 31, 2007, the entire content of which is incorporated herein by reference.

BACKGROUND

1. Technical Field

This application relates to a surgical stapling apparatus, and more particularly, to an articulating mechanism for use with an endoscopic surgical stapling apparatus for sequentially applying a plurality of surgical fasteners to body tissue and optionally incising fastened tissue.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose can include two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. Nos. 3,079,606 and 3,490,675.

A later stapler disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. Other examples of such staplers are disclosed in U.S. Pat. Nos. 4,429,695 and 5,065,929.

Each of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); and U.S. Pat No. 5,332,142 (Robinson, et al.).

U.S. Surgical, the assignee of the present application, has manufactured and marketed endoscopic stapling instruments, such as the Multifire ENDO GIA* 30 instrument, for several years. These instruments have provided significant clinical benefits. Nonetheless, improvements are possible, for example, by reducing the cost and complexity of manufacture.

Current laparoscopic linear stapling devices are configured to operate with disposable loading units and/or staple cartridges of only one size. For example, individual linear staplers are presently available for applying parallel rows of staples measuring 30 mm, 45 mm and 60 mm in length. Thus, during a normal operation, a surgeon may be required to utilize several different stapling instruments to perform a single laparoscopic surgical procedure. Such practices increase the time, complexity and overall costs associated with laparoscopic surgical procedures. In addition, costs are greater in designing and manufacturing multiple stapler sizes, as opposed to creating a single, multipurpose stapler.

It would be extremely beneficial to provide a surgical device for use during laparoscopic and/or endoscopic surgical procedures that can be employed with several different sized disposable loading units to reduce the overall costs associated with such procedures. It would also be particularly beneficial if the device could perform multiple tasks, using disposable loading units of varying size and of varying purpose, such as, for example, to staple, clip, cut and/or articulate.

In making improvements or modifications to the current instruments, it would be highly desirable not to sacrifice any of the important benefits of the MULTIFIRE ENDO GIA* 30 instrument as compared to other commercially available products. For example, any improvement should advantageously provide a fresh knife blade for each firing of the instrument and ensure that the disposable loading unit is securely retained in the stapling instrument unless and until the operating team chooses to remove it. It is desirable for the end effector to be capable of articulating with respect to the elongated shaft of the instrument.

SUMMARY

In accordance with the present disclosure an articulation mechanism is provided including a housing defining a receptacle. The receptacle includes a throughbore. A main shaft is rotatably supported in the receptacle and includes a base portion and a cylindrical body portion. The base portion has an upper support surface and a bottom surface having a cam member extending from the bottom surface through the throughbore of the housing. A lower clutch is non-rotatably supported in the receptacle of the housing. The lower clutch has an outer rim portion and an inner annular serrated portion. The lower clutch defines a throughbore dimensioned to receive the cylindrical body portion of the main shaft. An upper clutch is rotatably fixed to the main shaft and has a base portion having a bottom surface having at least one projection. The upper clutch has a throughbore dimensioned to receive the cylindrical body of the main shaft and is positioned about the cylindrical body portion of the main shaft such that the bottom surface of the upper clutch is in juxtaposed alignment with the annular serrated portion of the lower clutch. In one embodiment, a cover is positioned over the receptacle of the housing. The cover encloses the main shaft, the lower clutch and the upper clutch within the receptacle. The cover defines a throughbore dimensioned to allow passage of the upper clutch. A biasing member is positioned between the cover and the upper clutch. The biasing member urges the bottom surface of the upper clutch into engagement with the serrated portion of the lower clutch. An articulation lever is rotatably fixed to the upper clutch and is rotatable to effect rotation of the upper clutch and the main shaft. A translation member includes a slot dimensioned to receive the cam member which extends from the bottom surface of the base portion of the main shaft such that rotation of the main shaft effects linear movement of the translation member. The at least one projection of the upper clutch and the annular serrated portion of the lower shaft are maintained in releasable engagement to releasably retain the articulation member in a fixed orientation.

BRIEF DESCRIPTION OF THE DRAWINGS

Various preferred embodiments are described herein with reference to the drawings:

FIG. 2 is a top view of the surgical apparatus shown in FIG. 1;

FIG. 3 is a side view of the surgical apparatus shown in FIG. 1;

FIG. 12a is a perspective view of a non-articulating disposable loading unit usable with the surgical stapling apparatus shown in FIG. 1;

FIG. 12b is a perspective view of the preferred articulating disposable loading unit of the surgical stapling apparatus shown in FIG. 1;

FIG. 19 is a perspective view of a disposable loading unit usable with the surgical stapling apparatus of FIG. 1;

FIG. 20 is another perspective view of a disposable loading unit usable with the surgical stapling apparatus of FIG. 1;

FIG. 23 is an enlarged perspective view of the distal end of the staple cartridge of the surgical stapling apparatus shown in FIG. 1;

FIG. 24 is a side cross-sectional view taken along section line 24-24 of FIG. 23;

FIG. 25 is a bottom perspective view of the staple cartridge shown in FIG. 21;

FIG. 26 is an enlarged perspective view of the actuation sled, the pushers and the fasteners shown in FIG. 21;

FIG. 28 is an enlarged perspective view of the mounting assembly of the disposable loading unit shown in FIG. 19 mounted to a distal end portion of the proximal housing portion;

FIG. 29 is an enlarged perspective view of the proximal housing portion and the mounting assembly of the disposable loading unit shown in FIG. 19 with the upper housing half removed;

FIG. 30 is a perspective view of the proximal housing portion and the mounting assembly of the disposable loading unit shown in FIG. 19 with the upper housing half removed;

FIG. 32 is an enlarged perspective view of the axial drive assembly shown in FIG. 31;

FIG. 33 is an enlarged perspective view of the proximal end of the axial drive assembly shown in FIG. 31 including the locking device;

FIG. 34 is an enlarged perspective view of the distal end of the axial drive assembly shown in FIG. 31;

FIG. 41 is an enlarged perspective view of the disposable loading unit of FIG. 19 during attachment to the elongated body of the surgical stapling apparatus shown in FIG. 1;

FIG. 42 is another enlarged perspective view of the disposable loading unit of FIG. 19 during attachment to the elongated body of the surgical stapling apparatus shown in FIG. 1;

FIG. 43 is a cross-sectional view taken along section line 43-43 of FIG. 41;

FIG. 44 is a cross-sectional view taken along section line 44-44 of FIG. 42;

FIG. 51 is a side cross-sectional view of the distal end of the tool assembly of the stapling apparatus shown in FIG. 1 during firing of the apparatus;

FIG. 52 is a side cross-sectional view of the distal end of the tool assembly of the stapling apparatus shown in FIG. 1 after firing of the apparatus;

FIG. 54 is a side cross-sectional view of the handle assembly of the stapling apparatus during actuation of the emergency release button;

FIG. 58 is a perspective view of the surgical stapling apparatus during articulation of the tool assembly;

FIG. 59 is a perspective view of the surgical stapling apparatus during articulation and rotation of the tool assembly;

FIG. 68 is a bottom side perspective view of the upper clutch of the articulation mechanism shown in FIG. 65;

FIG. 69 is a perspective view from the top of the upper clutch shown in FIG. 68;

FIG. 70 is a top perspective view of the lower clutch of the articulation mechanism shown in FIG. 65;

FIG. 79 is a cross-sectional view taken along section lines 79-79 of FIG. 78; and FIG. 80 is a cross-sectional view of the articulation mechanism shown in FIG. 64 with the articulation lever rotated and the upper clutch projection reengaged with the serrations of the lower clutch.

DETAILED DESCRIPTION OF EMBODIMENTS

Figure 1:
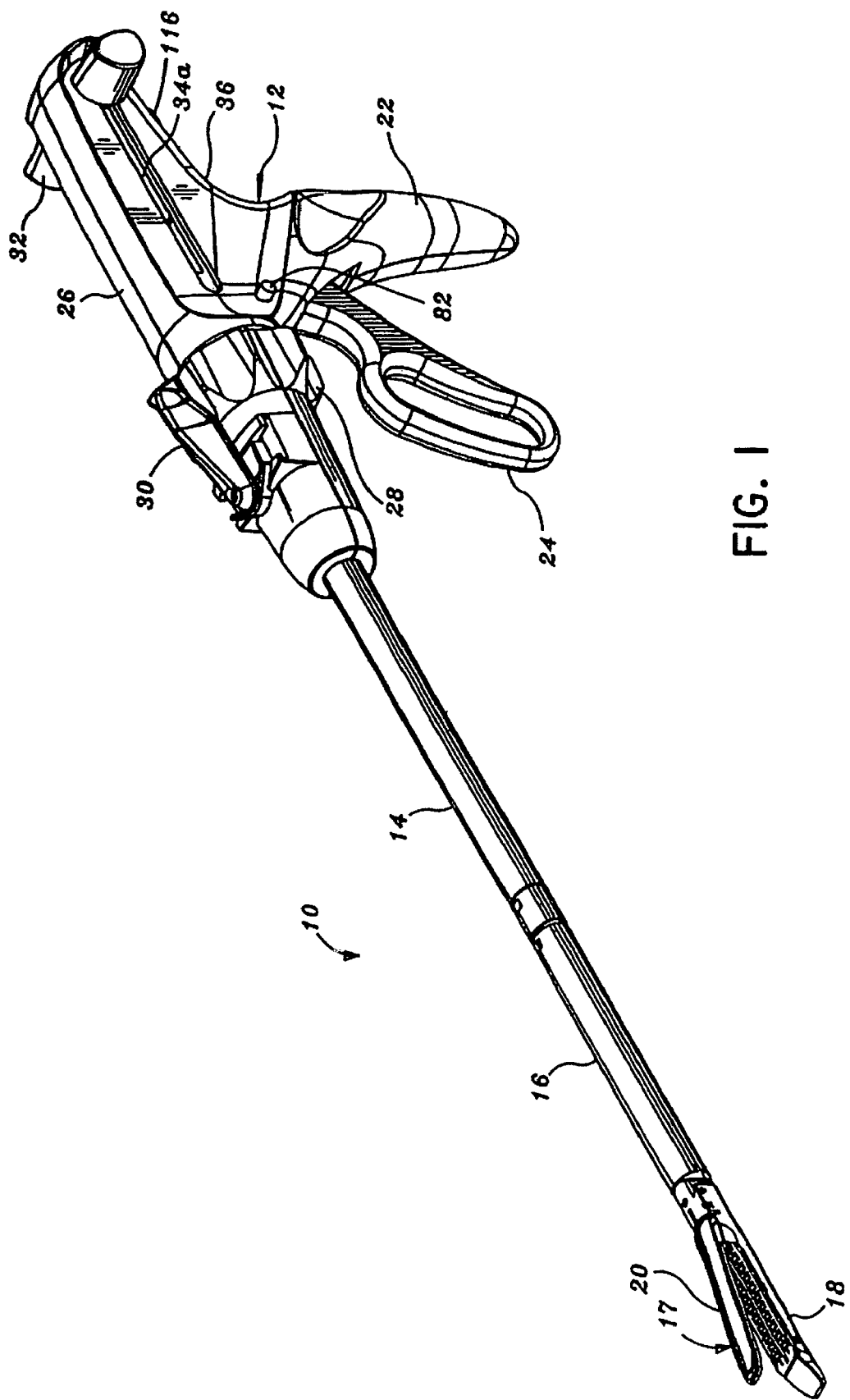
FIG. 1 is a perspective view of one preferred embodiment of the presently disclosed surgical stapling apparatus.

Preferred embodiments of the presently disclosed endoscopic surgical stapling apparatus will now be described in detail with reference to the drawings, in which like reference numerals designate identical or corresponding elements in each of the several views.

In the drawings and in the description that follows, the term "proximal", as is traditional, will refer to the end of the stapling apparatus which is closest to the operator, while the term distal will refer to the end of the apparatus which is furthest from the operator.

FIGS. 1-3 illustrate one embodiment of the presently disclosed surgical stapling apparatus shown generally as 10. Briefly, surgical stapling apparatus 10 includes a handle assembly 12 and an elongated body 14. A disposable loading unit or DLU 16 is releasably secured to a distal end of elongated body 14. Disposable loading unit 16 includes a tool assembly 17 having a cartridge assembly 18 housing a plurality of surgical staples and an anvil assembly 20 movably secured in relation to cartridge assembly 18. Disposable loading unit 16 is configured to apply linear rows of staples measuring from about 30 mm to about 60 mm in length. Disposable loading units having linear rows of staples of other lengths are also envisioned, e.g., 45 mm. Handle assembly 12 includes a stationary handle member 22, a movable handle member 24, and a barrel portion 26. A rotatable member 28 is preferably mounted on the forward end of barrel portion 26 to facilitate rotation of elongated body 14 with respect to handle assembly 12. An articulation lever 30 is also preferably mounted on the forward end of barrel portion 26 adjacent rotatable knob 28 to facilitate articulation of tool assembly 17. A pair of retraction knobs 32 are movably positioned along barrel portion 26 to return surgical stapling apparatus 10 to a retracted position, as will be described in detail below.

Figure 4:
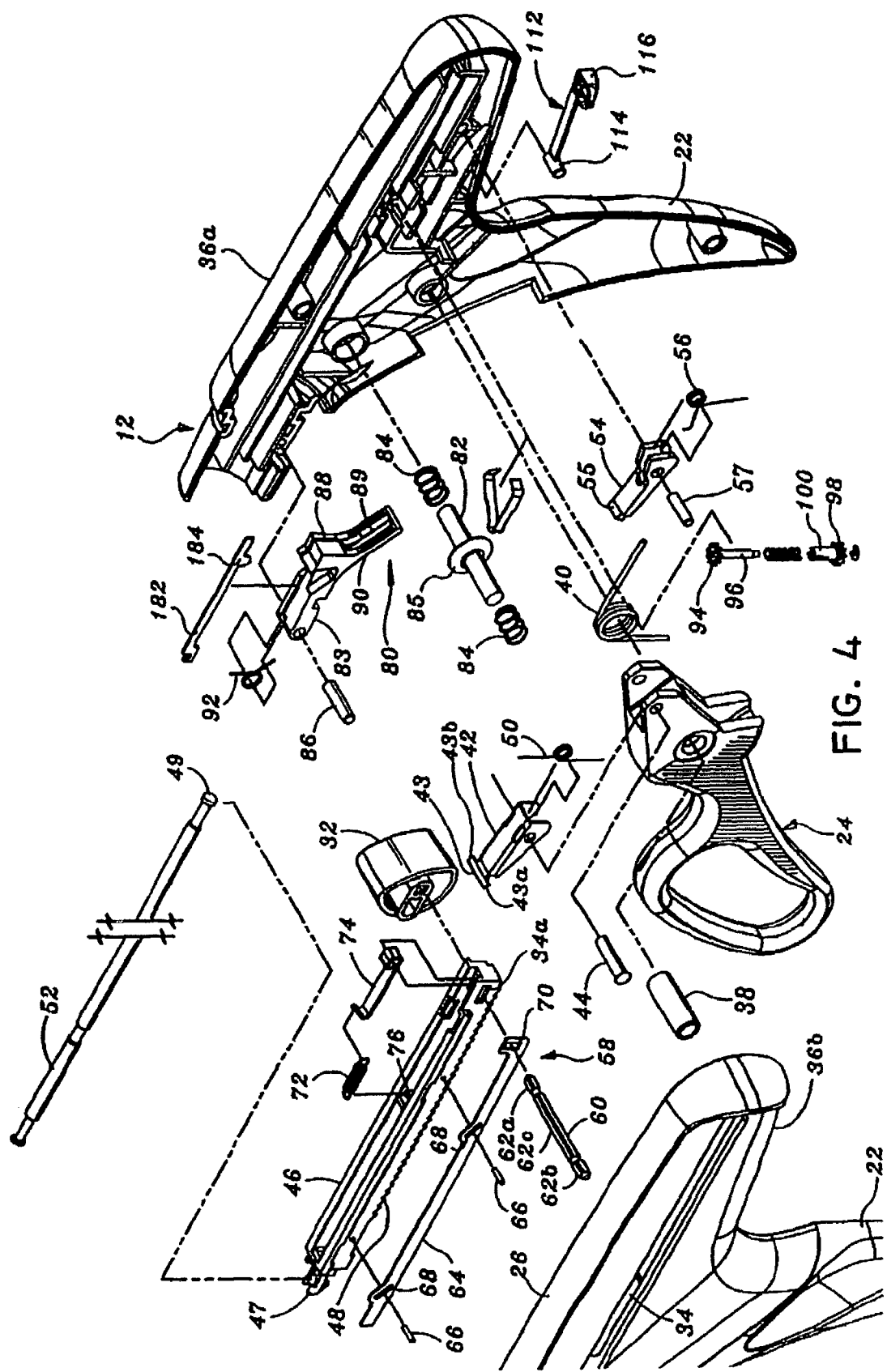
FIG. 4 is a perspective view with parts separated of the handle assembly of the surgical apparatus shown in FIG. 1.

Referring to FIG. 4, handle assembly 12 includes housing 36, which is preferably formed from molded housing half-sections 36a and 36b, which forms stationary handle member 22 and barrel portion 26 of handle assembly 12 (See FIG. 1). Movable handle member 24 is pivotably supported between housing half-sections 36a and 36b about pivot pin 38. A biasing member 40, which is preferably a torsion spring, biases movable handle 24 away from stationary handle 22. An actuation shaft 46 is supported within barrel portion 26 of housing 36 and includes a toothed rack 48. A driving pawl 42 having a rack engagement finger 43 with laterally extending wings 43a and 43b is pivotably mounted to one end of movable handle 24 about a pivot pin 44. A biasing member 50, which is also preferably a torsion spring, is positioned to urge engagement finger 43 of driving pawl 42 towards toothed rack 48 of actuation shaft 46. Movable handle 24 is pivotable to move engagement finger 43 of driving pawl 42 into contact with toothed rack 48 of actuation shaft 46 to advance the actuation shaft linearly in the distal direction. The forward end of actuation shaft 46 rotatably receives the proximal end 49 of a control rod 52 such that linear advancement of actuation shaft 46 causes corresponding linear advancement of control rod 52. A locking pawl 54 having a rack engagement member 55 is pivotably mounted within housing 36 about pivot pin 57 and is biased towards toothed rack 48 by biasing member 56, which is also preferably a torsion spring. Engagement member 55 of locking pawl 54 is movable into engagement with toothed rack 48 to retain actuation shaft 46 in a longitudinally fixed position.

A retraction mechanism 58 which includes a pair of retractor knobs 32 (See FIG. 1) is connected to the proximal end of actuation shaft 46 by a coupling rod 60. Coupling rod 60 includes right and left engagement portions 62a and 62b for receiving retractor knobs 32 and a central portion 62c which is dimensioned and configured to translate within a pair of longitudinal slots 34a formed in actuation shaft 46 adjacent the proximal end thereof. A release plate 64 is operatively associated with actuation shaft 46 and is mounted for movement with respect thereto in response to manipulation of retractor knobs 32. A pair of spaced apart pins 66 extend outwardly from a lateral face of actuation shaft 46 to engage a pair of corresponding angled cam slots 68 formed in release plate 64. Upon rearward movement of retractor knobs 32, pins 66 can release plate 64 downwardly with respect to actuation shaft 46 and with respect to toothed rack 48 such that the bottom portion of release plate 64 extends below toothed rack 48 to disengage engagement finger 43 of driving pawl 42 from toothed rack 48. A transverse slot 70 is formed at the proximal end of release plate 64 to accommodate the central portion 62c of coupling rod 60, and elongated slots 34 (See FIG. 1) are defined in the barrel section 26 of handle assembly 12 to accommodate the longitudinal translation of coupling rod 60 as retraction knobs 32 are pulled rearwardly to retract actuation shaft 46 and thus retract control rod 52 rearwardly. Actuation shaft 46 is biased proximally by spring 72 which is secured at one end to coupling rod portion 62 via connector 74 and at the other end to post 76 on actuation shaft 46.

Figure 5:
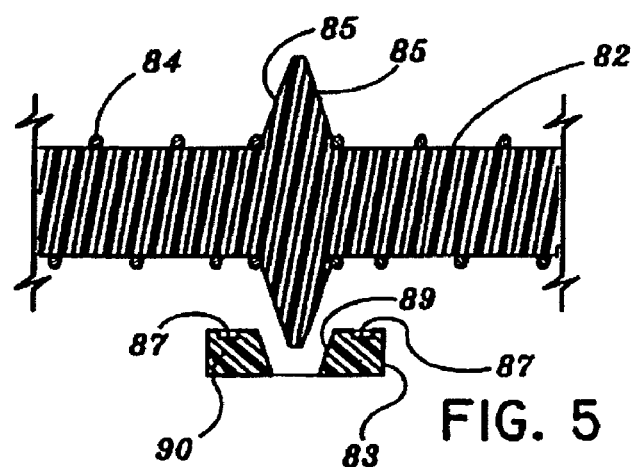
FIG. 5 is a cross-sectional view of a portion of the firing lockout mechanism shown in FIG. 4.

Referring also to FIG. 5, handle assembly 12 includes a firing lockout assembly 80 which includes a plunger 82 and a pivotable locking member 83. Plunger 82 is biased to a central position by biasing springs 84 and includes annular tapered camming surfaces 85. Each end of plunger 82 extends through housing 36 (See FIG. 1) adjacent an upper end of stationary handle 22. Pivotable locking member 83 is pivotably attached at its distal end between housing half-sections 36a and 36b about pivot pin 86 and includes a locking surface 88 and proximal extension 90 having a slot 89 formed therein. Locking member 83 is biased by spring 92 counter-clockwise (as viewed in FIG. 4) to move locking surface 88 to a position to abut the distal end of actuation shaft 46 to prevent advancement of shaft 46 and subsequent firing of stapling apparatus 10. Annular tapered camming surface 85 is positioned to extend into tapered slot 89 in proximal extension 90. Lateral movement of plunger 82 in either direction against the bias of either spring 84 moves tapered camming surface 85 into engagement with the sidewalls of tapered slot 89 to pivot locking member 83 clockwise about pivot pin 86, as viewed in FIG. 4, to move blocking surface 88 to a position to permit advancement of actuation shaft 46 and thus firing of stapling apparatus 10. Blocking surface 88 is retained in this position by recesses 87 which receive the tapered tip of camming surface 85 to lock locking member 83 in a counter-clockwise position. Operation of firing lockout assembly 80 will be further illustrated below.

Figure 6:
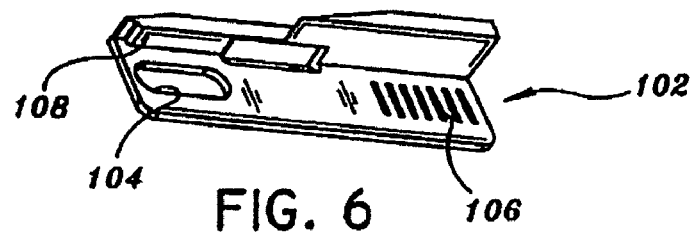
FIG. 6 is a perspective of the slide plate of the anti-reverse clutch mechanism of the surgical apparatus.
Figure 7:
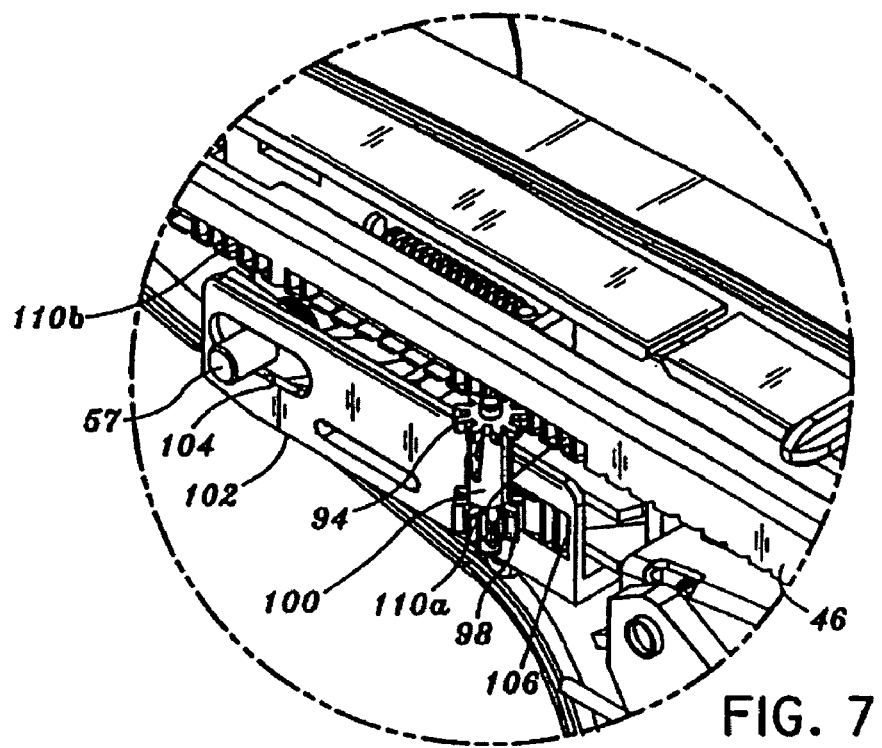
FIG. 7 is an enlarged perspective view of the anti-reverse clutch mechanism shown in FIG. 1.

Referring to FIGS. 4, 6, and 7, handle mechanism 12 also includes an anti-reverse clutch mechanism which includes a first gear 94 rotatably mounted on a first shaft 96, and second gear 98 mounted on a second shaft 100, and a slide plate 102 (FIGS. 6 and 7) slidably mounted within housing 36. Slide plate 102 includes an elongated slot 104 dimensioned and configured to be slidably positioned about locking pawl pivot pin 57, a gear plate 106 configured to mesh with the teeth of second gear 98, and a cam surface 108. In the retracted position, cam surface 108 of slide plate 102 engages locking pawl 54 to prevent locking pawl 54 from engaging toothed rack 48. Actuation shaft 46 includes a distal set of gear teeth 110a spaced from a proximal set of gear teeth 110b positioned to engage first gear 94 of actuation shaft 46 during movement of actuation shaft 46. When actuation shaft 46 is advanced by pivoting movable handle 24 about pivot pin 38, distal gear teeth 110a on actuation shaft 46 mesh with and rotate first gear 94 and first shaft 96. First shaft 96 is connected to second shaft 100 by spring clutch assembly such that rotation of first shaft 96 will cause corresponding rotation of second shaft 100. Rotation of second shaft 100 causes corresponding rotation of second gear 98 which is engaged with gear plate 106 on slide plate 102 to cause linear advancement of slide plate 102. Linear advancement of slide plate 102 is limited to the length of elongated slot 104. When slide plate has been advanced the length of slot 104, cam surface 108 releases locking pawl 54 such that it is moved into engagement with toothed rack 48. Continued advancement of actuation shaft 46 eventually moves gear teeth 110b into engagement with gear plate 106. However, since slide plate 102 is longitudinally fixed in position, the spring clutch is forced to release, such that continued distal advancement of actuation shaft 46 is permitted.

When actuation shaft 46 is returned to the retracted position (by pulling retraction knobs 34 proximally, as discussed above) gear teeth 110b engage first gear 94 to rotate second gear 98 in the reverse direction to retract slide member 102 proximally within housing 36. Proximal movement of slide member 102 advances cam surface 108 into locking pawl 54 prior to engagement between locking pawl 54 and toothed rack 48 to urge locking pawl 54 to a position to permit retraction of actuation shaft 46.

Referring again to FIG. 4, handle assembly 12 includes an emergency return button 112 pivotally mounted within housing 36 about a pivot member 114 supported between housing half-sections 36a and 36b. Return button 112 includes an externally positioned member 116 positioned on the proximal end of barrel portion 26. Member 116 is movable about pivot member 114 into engagement with the proximal end of locking pawl 54 to urge rack engagement member 55 out of engagement with toothed rack 48 to permit retraction of actuation shaft 46 during the firing stroke of the stapling apparatus 10. As discussed above, during the clamping portion of advancement of actuation shaft 46, slide plate 102 disengages pawl 54 from rack 48 and thus actuation of return button 112 is not necessary to retract the actuation shaft 46.

Figure 8:
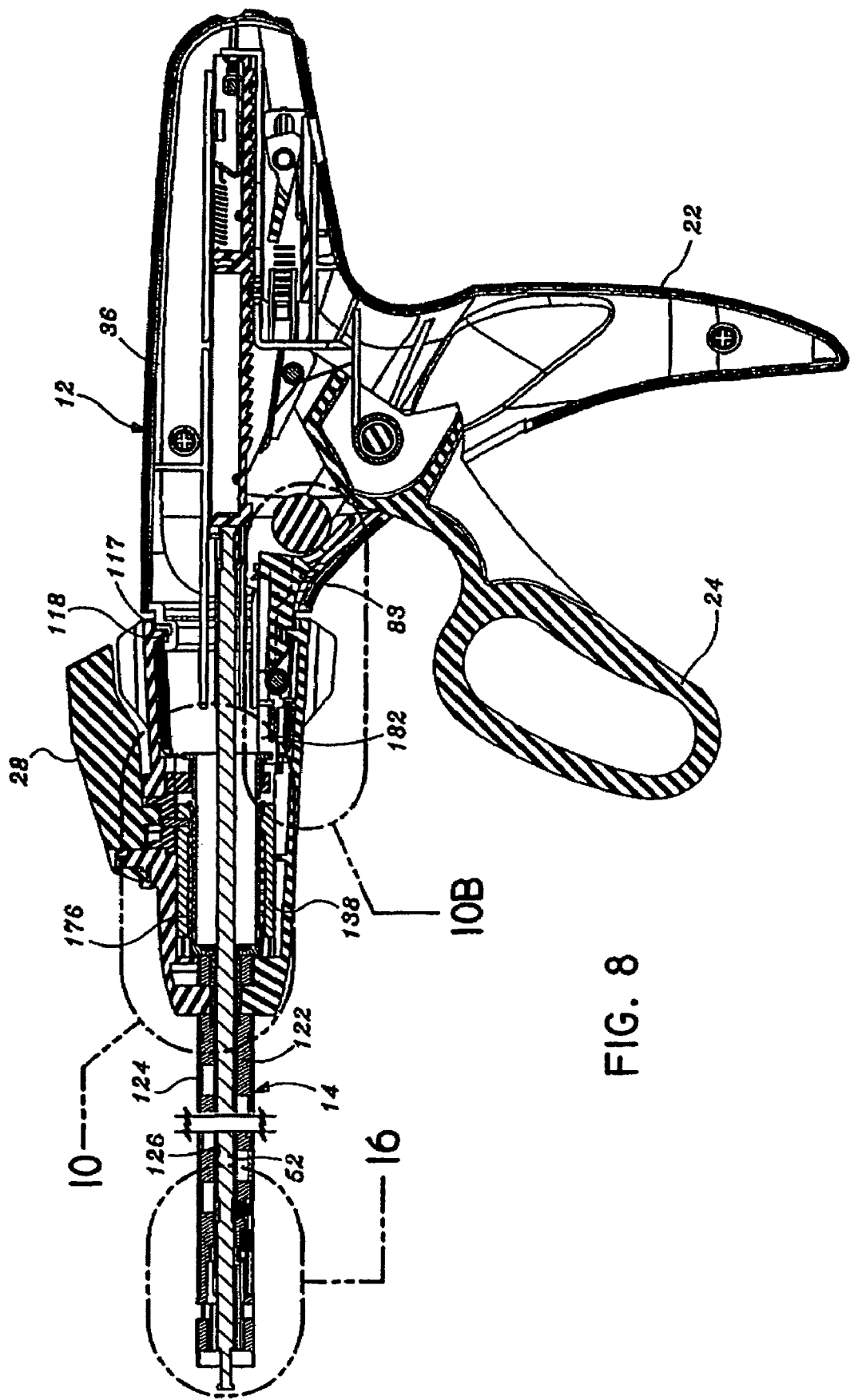
FIG. 8 is a side cross-sectional view of the surgical stapling apparatus shown in FIG. 1 in the non-actuated position with the disposable loading unit removed.
Figure 9:
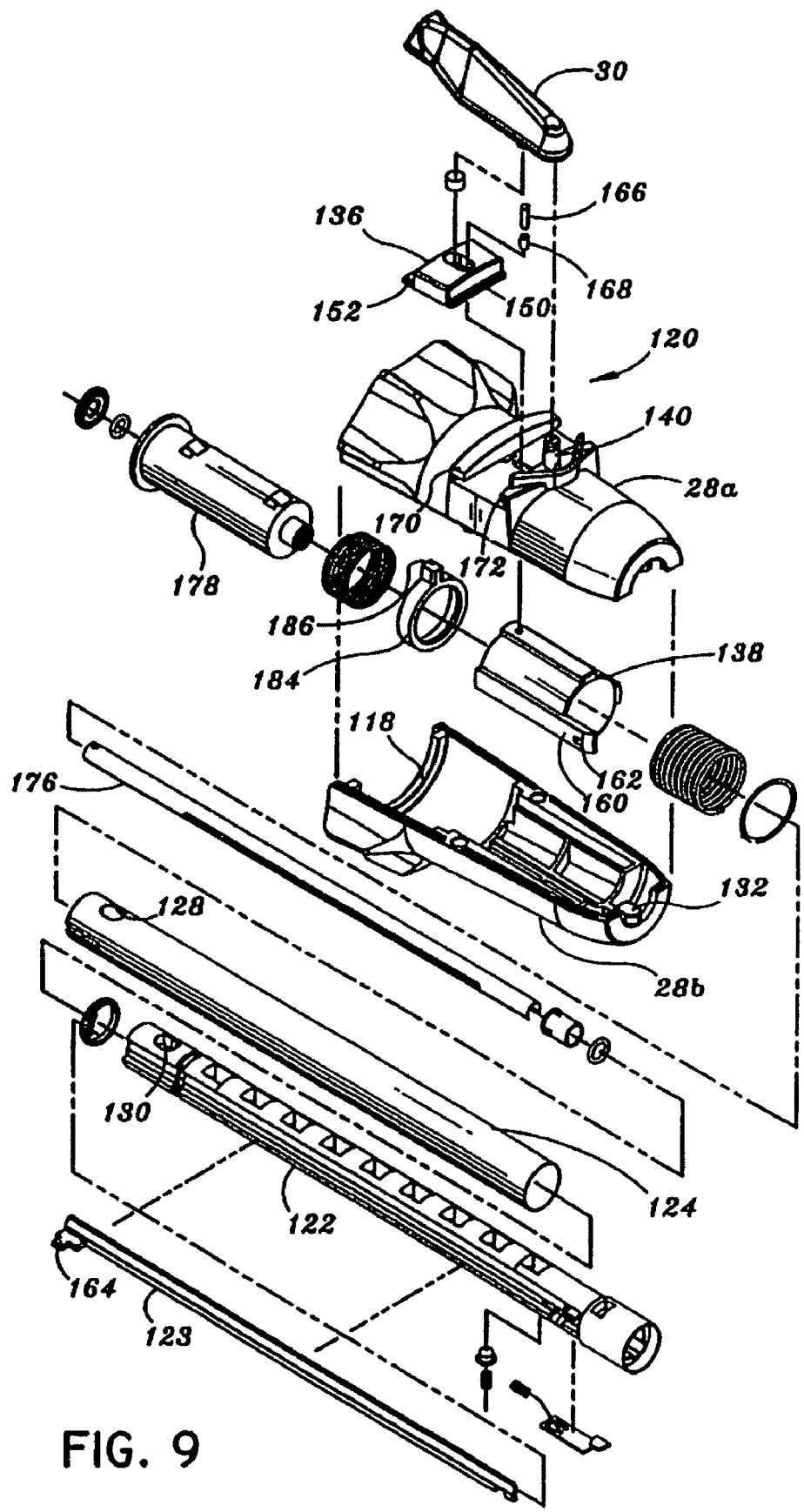
FIG. 9 is a perspective view with parts separated of the rotation member, the articulation mechanism, and the elongated body of the surgical stapling apparatus shown in FIG. 1.
Figure 10:
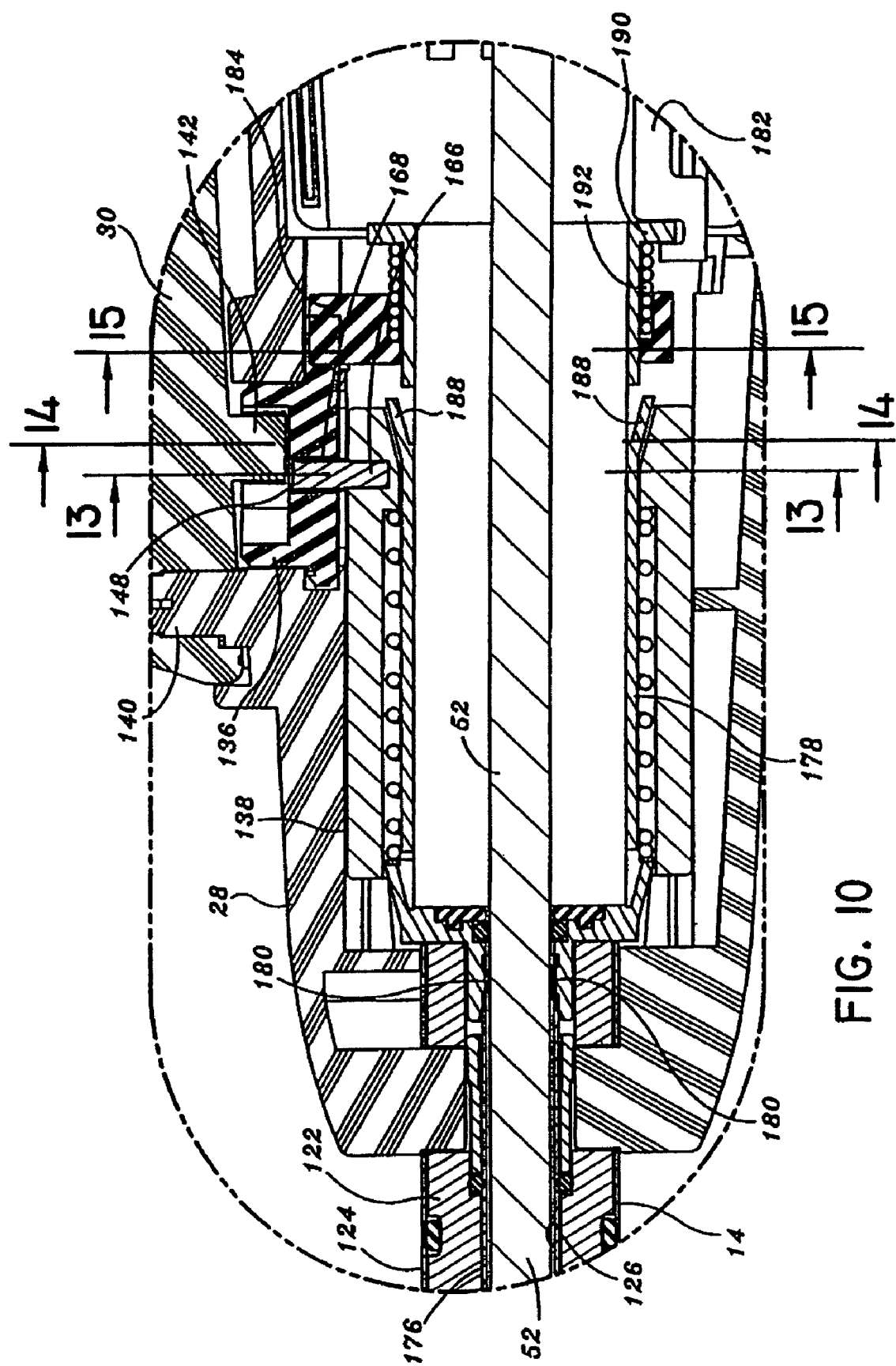
FIG. 10 is an enlarged view of the indicated area of detail shown in FIG. 8.

FIG. 8 illustrates the interconnection of elongated body 14 and handle assembly 12. Referring to FIGS. 8-10, housing 36 includes an annular channel 117 configured to receive an annular rib 118 formed on the proximal end of rotation member 28, which is preferably formed from molded half-sections 28a and 28b. Annular channel 117 and rib 118 permit relative rotation between rotation member 28 and housing 36. Elongated body 14 includes inner housing 122 and an outer casing 124. Inner housing 122 is dimensioned to be received within outer casing 124 and includes an internal bore 126 (FIG. 8) which extends therethrough and is dimensioned to slidably receive a first articulation link 123 and control rod 52. The proximal end of housing 122 and casing 124 each include a pair of diametrically opposed openings 130 and 128, respectively, which are dimensioned to receive radial projections 132 formed on the distal end of rotation member 28. Projections 132 and openings 128 and 130 fixedly secure rotation member 28 and elongated body 14 in relation to each other, both longitudinally and rotatably. Rotation of rotation knob 28 with respect to handle assembly 12 thus results in corresponding rotation of elongated body 14 with respect to handle assembly 12.

An articulation mechanism 120 is supported on rotatable member 28 and includes articulation lever 30, a cam member 136, a translation member 138, and first articulation link 123 (FIG. 9). Articulation lever 30 is pivotably mounted about pivot member 140 which extends outwardly from rotation member 28 and is preferably formed integrally therewith. A projection 142 extends downwardly from articulation lever 30 for engagement with cam member 136.

Figure 12:
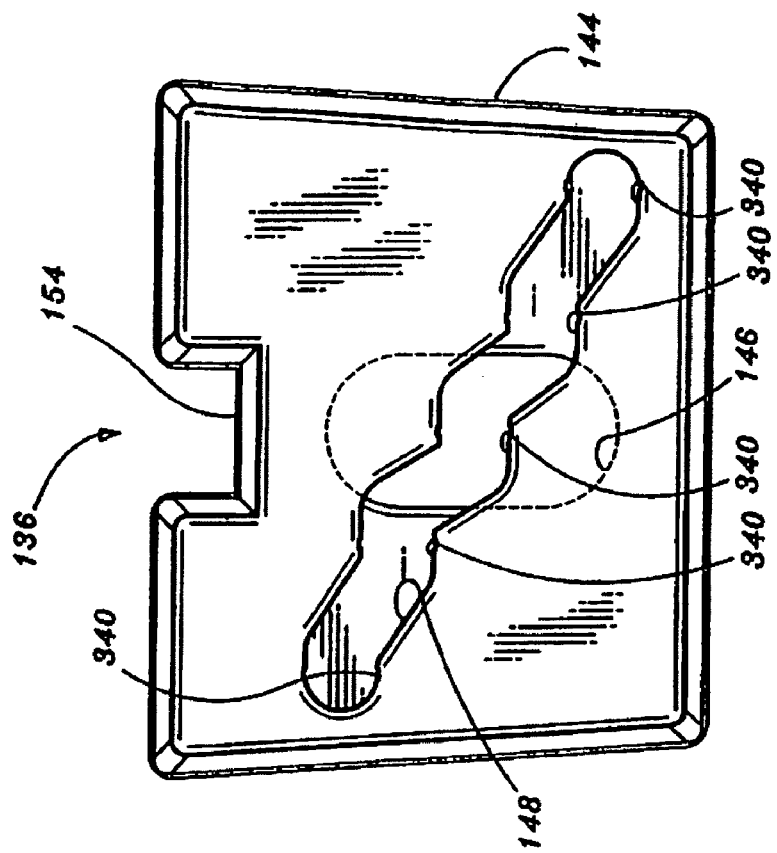
FIG. 12 is a top view of the cam member of the articulation mechanism of the surgical stapling apparatus shown in FIG. 1.
Figure 11:
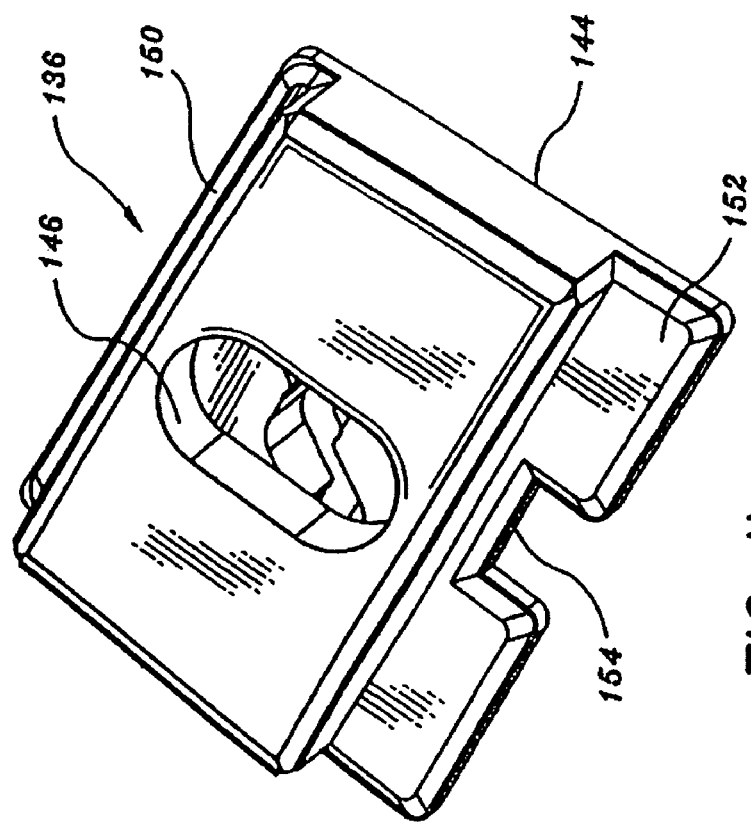
FIG. 11 is a perspective view of the cam member of the articulation mechanism of the surgical stapling apparatus shown in FIG. 1.

Referring temporarily to FIGS. 11 and 12, cam member 136 includes a housing 144 having an elongated slot 146 extending through one side thereof and a stepped camming surface 148 formed in the other side thereof. Each step of camming surface 148 corresponds to a particular degree of articulation of stapling apparatus 10. Although five steps are illustrated, fewer or more steps may be provided. Elongated slot 146 is configured to receive projection 142 formed on articulation lever 30. Housing 144 includes a distal stepped portion 150 and a proximal stepped portion 152. Proximal stepped portion 152 includes a recess 154.

Figure 13:
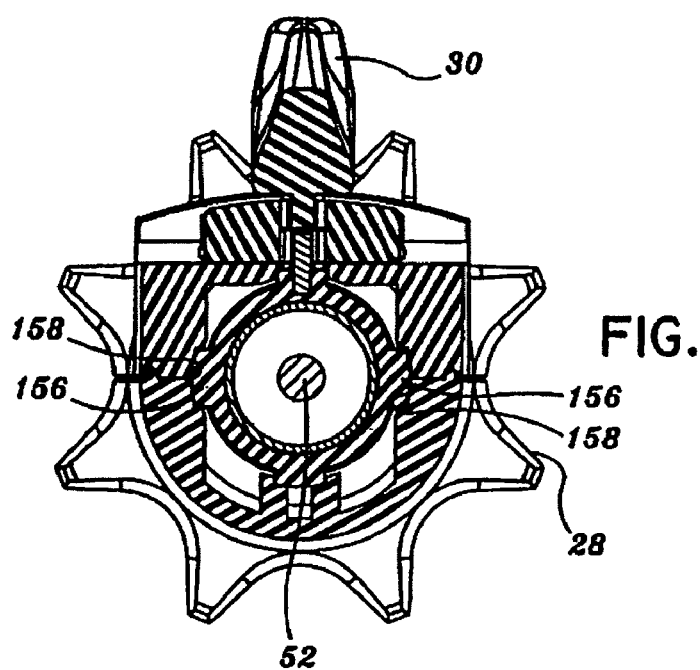
FIG. 13 is a cross-sectional view taken along section line 13-13 of FIG. 10.
Figure 14:
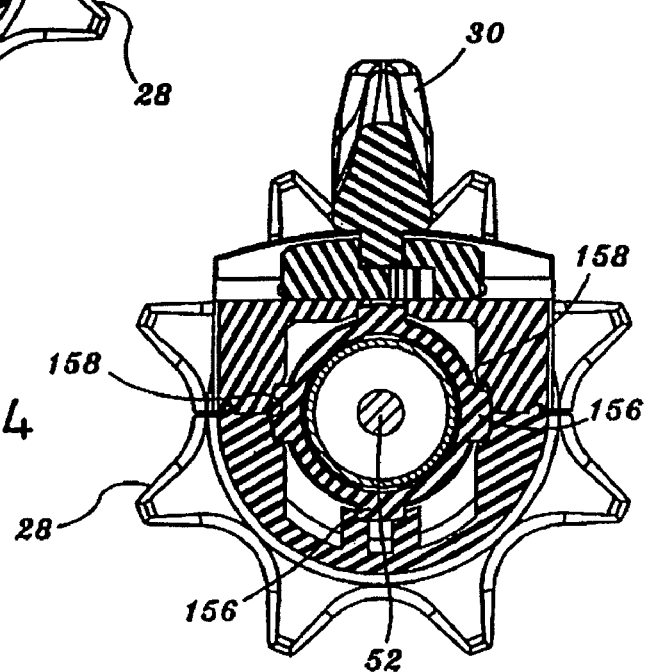
FIG. 14 is a cross-sectional view taken along section line 14-14 of FIG. 10.
Figure 15:
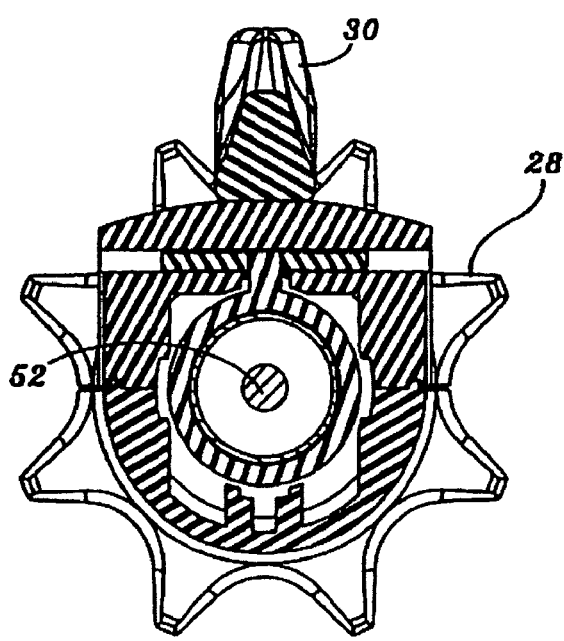
FIG. 15 is a cross-sectional view taken along section line 15-15 of FIG. 10.

Referring again to FIGS. 8-10 and also to FIGS. 13-15, translation member 138 includes a plurality of ridges 156 which are configured to be slidably received within grooves 158 formed along the inner walls of rotation member 28. Engagement between ridges 156 and grooves 158 prevent relative rotation of rotation member 28 and translation member 138 while permitting relative linear movement. The distal end of translation member 138 includes arm 160 which includes an opening 162 configured to receive a finger 164 extending from the proximal end of articulation link 123 (See FIG. 10a). A pin 166 having a housing 168 constructed from a non-abrasive material, e.g., teflon, is secured to translation member 138 and dimensioned to be received within stepped camming surface 148.

In an assembled condition, proximal and distal stepped portions 150 and 152 of cam member 136 are positioned beneath flanges 170 and 172 formed on rotation member 28 to restrict cam member 136 to transverse movement with respect to the longitudinal axis of stapling apparatus 10. When articulation lever 30 is pivoted about pivot member 140, cam member 136 is moved transversely on rotation member 28 to move stepped camming surface 148 transversely relative to pin 166, forcing pin 166 to move proximally or distally along stepped cam surface 148. Since pin 166 is fixedly attached to translation member 138, translation member 138 is moved proximally or distally to effect corresponding proximal or distal movement of first actuation link 123.

Figure 64:
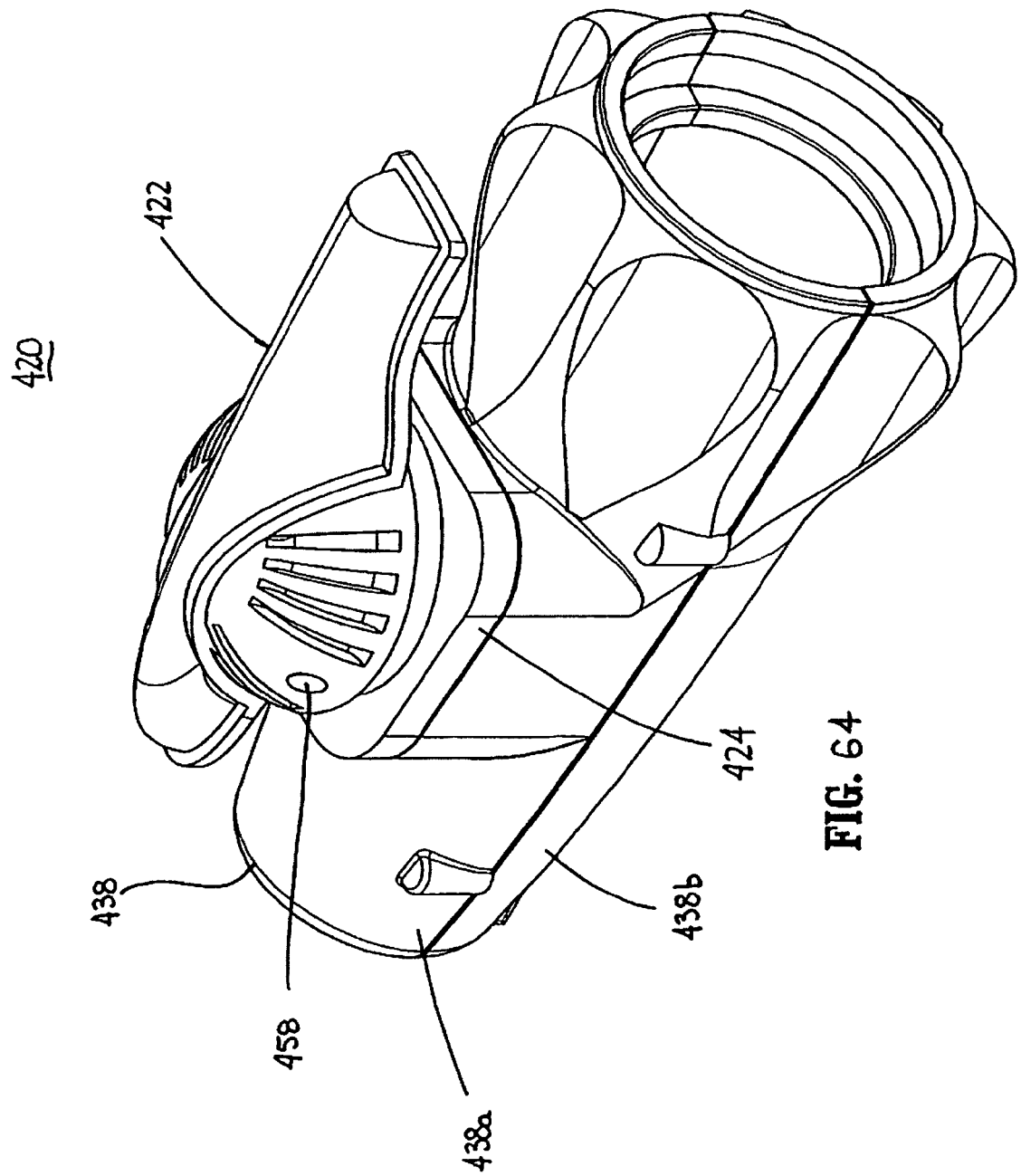
FIG. 64 is a perspective view of another embodiment of the presently disclosed articulation mechanism.
Figure 65:
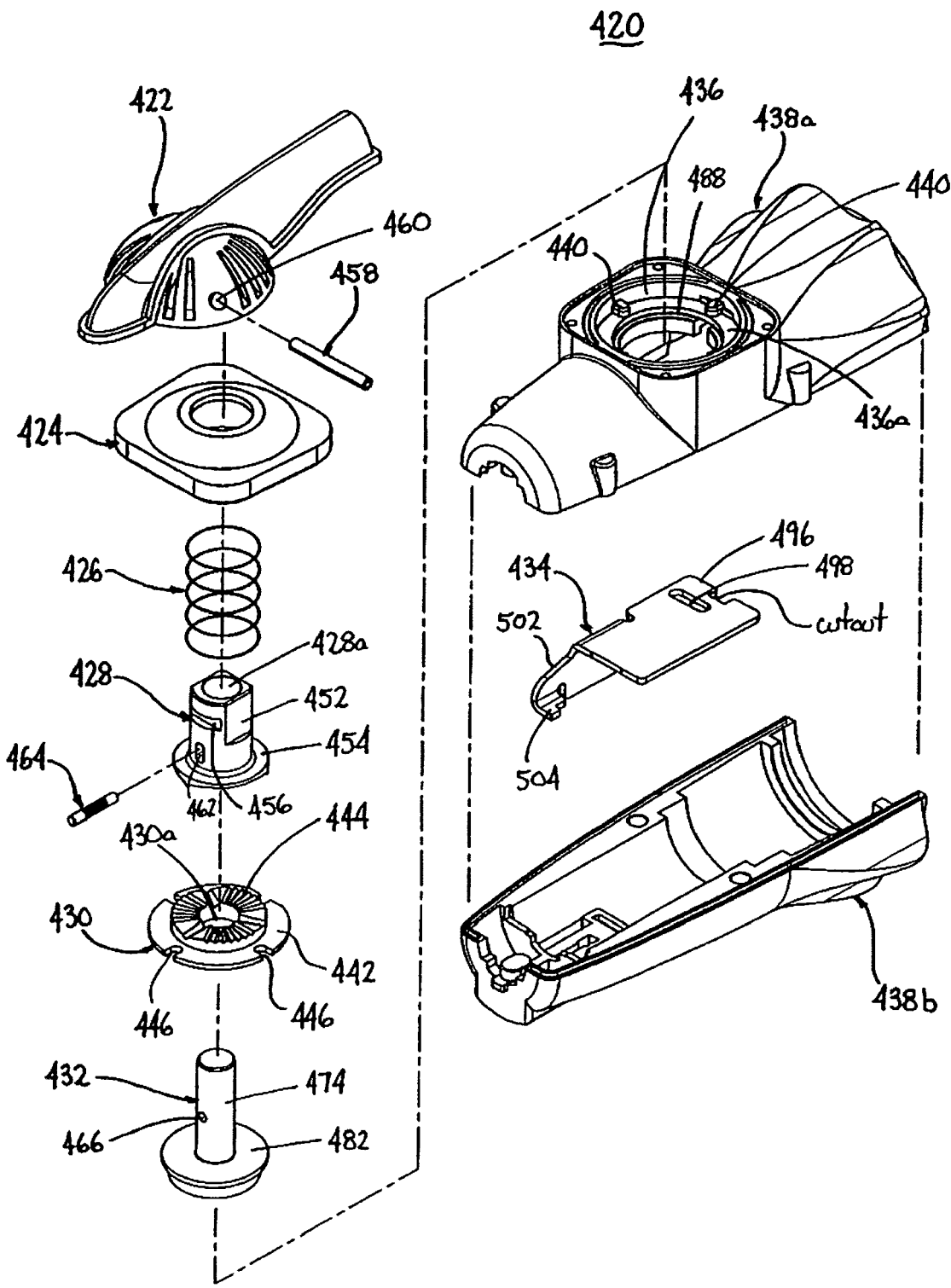
FIG. 65 is a perspective view of the articulation mechanism shown in FIG. 64 with parts separated.

FIGS. 64-80 illustrate another embodiment of the presently disclosed articulation mechanism shown generally as 420. Referring to FIGS. 64 and 65, articulation mechanism 420 includes an articulation lever 422, a mechanism cover 424, a biasing member 426, an upper clutch 428, a lower clutch 430, a main shaft 432 and a translation member 434. The entire articulation mechanism is supported in a receptacle 436 formed in the top half-section 438a of rotatable member 438 but may also be supported in the handle assembly. Receptacle 436 defines a substantially cylindrical throughbore having a shoulder 436a dimensioned to receive and support lower clutch 430. Shoulder 436a includes one or more tabs 440.

Figure 66:
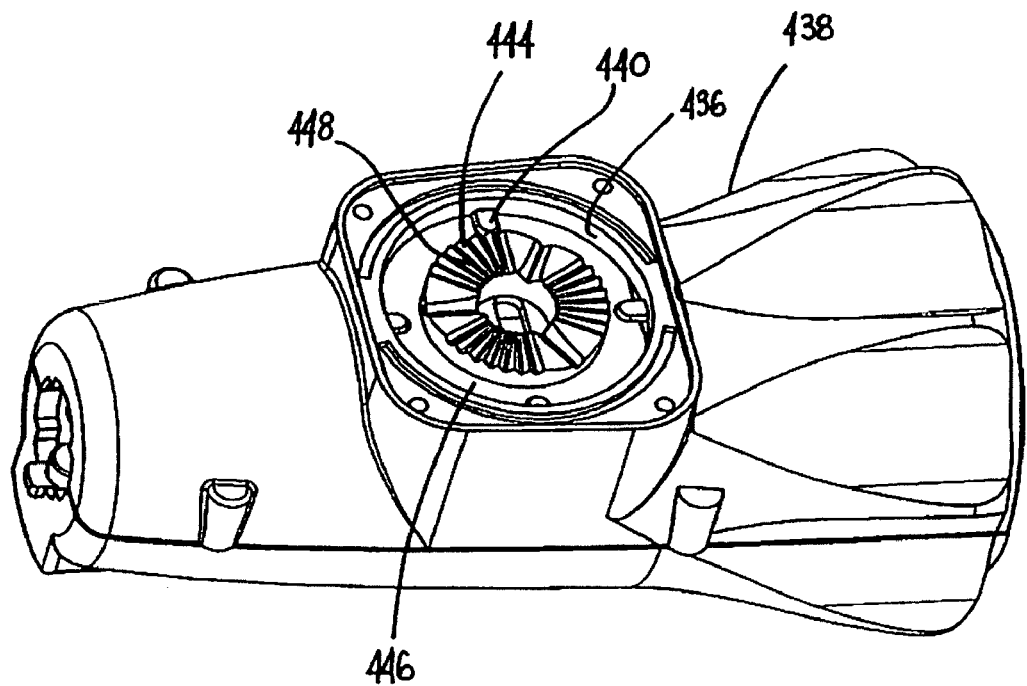
FIG. 66 is a perspective view of the rotatable member of the articulation mechanism shown in FIG. 64 with the lower clutch positioned in the receptacle of the rotatable member.

Referring also to FIGS. 66 and 70, lower clutch 430 includes an outer rim portion 442 and an inner circular serrated portion 444. Outer rim portion 442 includes one or more cutouts 446 which are dimensioned to receive tabs 440 on shoulder 436a of receptacle 436. Lower clutch 430 is positioned within receptacle 436 atop shoulder 436a such that tabs 440 are received within cutouts 446 and lower clutch 430 is prevented from rotating within receptacle 436 (FIG. 66). Circular serrated portion 444 includes a series of shallow serrations 448 and three spaced deep serrations 450 (FIG. 70). These serrations 448 and 450 include angled walls and function to retain articulation lever 422 at a plurality of different articulated positions as will be discussed in further detail below. Lower clutch 430 also defines a central throughbore 430a which is dimensioned to receive main shaft 432.

Referring to FIGS. 65, 68 and 69, upper clutch 428 includes a hub portion 452 and a base portion 454. Hub portion 452 defines a central throughbore 428a and a channel 456 which is dimensioned to receive a pin 458. Pin 458 is inserted through an opening 460 in articulation lever 422 and into channel 456 to rotatably fix articulation lever 422 to upper clutch 428. Hub portion 422 also includes an elongated slot 462 which is dimensioned to receive a pin 464. Pin 464 is inserted through slot 462 and a hole 466 formed in main shaft 432 to rotatably fix upper clutch 428 to main shaft 432. Pin 464 is longitudinally slidable in slot 462 to allow upper clutch 428 to move axially in relation to main shaft 432.

Base portion 454 of upper clutch includes an upper face 469 and a lower face 468 (FIG. 68) which is positioned in juxtaposed alignment with serrated portion 444 of lower clutch 430. Lower face 468 includes a plurality of spaced projections 470 configured to be received within deep and shallow serrations 450 and 448 of lower clutch 430. In one embodiment, projections 470 have a triangularly shaped cross-section in which the walls defining the triangle are steeper near the apex of the triangle. Such a configuration allows the apex of projections 470 to be received in shallow serrations 448 and substantially the entire projection 470 to be received in deep serrations 450, thus effecting a more secure engagement. The shape of projections 470 has two portions and two different engagement surfaces to define two different vertical positions for the mechanism.

Figure 71:
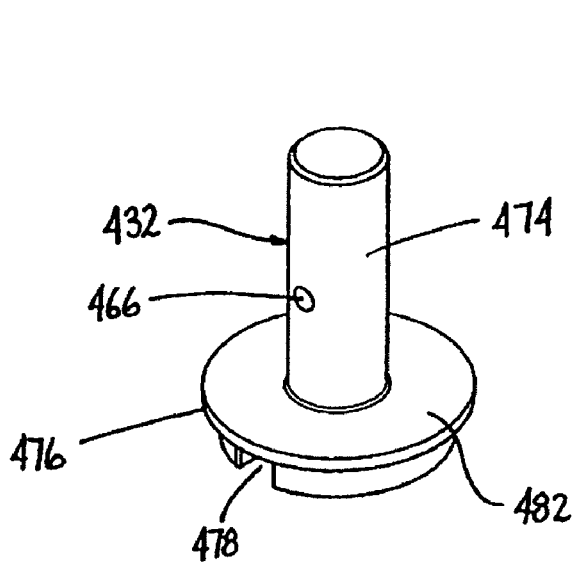
FIG. 71 is a top perspective view of the main shaft of the articulation mechanism shown in FIG. 65.
Figure 72:
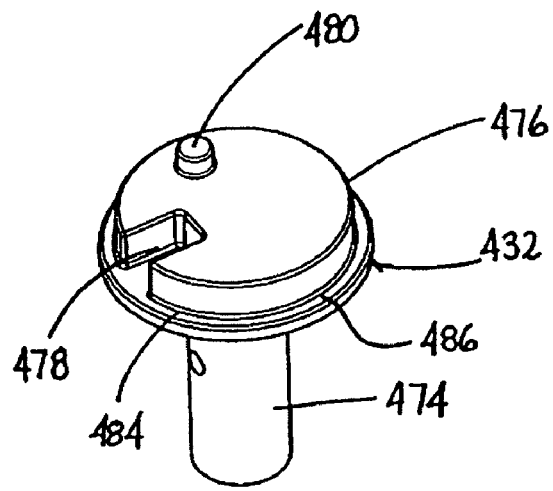
FIG. 72 is a bottom perspective view of the main shaft shown in FIG. 71.

Referring to FIGS. 65, 71 and 72, main shaft 432 includes a substantially cylindrical body portion 474 and a disc-shaped base portion 476. Base portion 476 defines a cutout 478 (FIG. 72) and includes a cam member or protrusion 480. Base portion 476 defines an annular support surface 482 (FIG. 71). Body portion 474 is dimensioned to extend through central throughbore 430a of lower clutch 430 and central throughbore 428a of upper clutch 428 such base portion 476 is positioned beneath upper clutch 428 and lower clutch 430 within receptacle 436 of rotatable member 438. Base portion 476 also includes a stepped portion 484 defining a shoulder 486. Shoulder 486 is supported on an annular shelf 488 (FIG. 65) formed in receptacle 436 such that main shaft 432 is rotatably supported within receptacle 436 of rotatable member 438.

Figure 73:
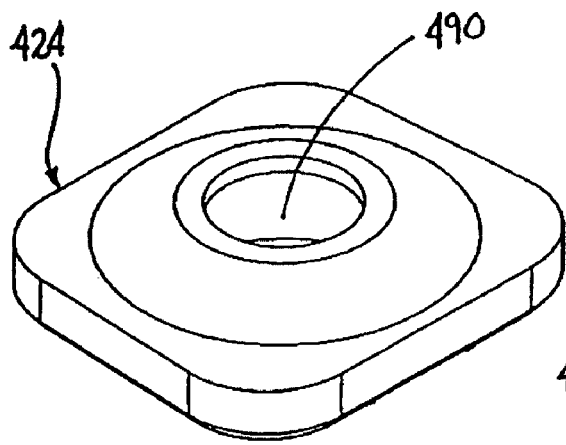
FIG. 73 is a top perspective view of the cover of the articulation mechanism shown in FIG. 65.
Figure 74:
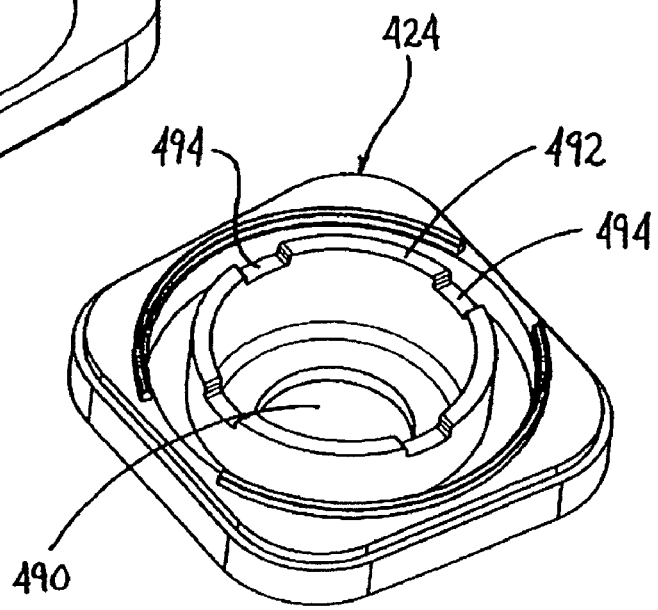
FIG. 74 is a bottom perspective view of the cover shown in FIG. 73.

Referring to FIGS. 65, 73 and 74, mechanism cover 424 defines an opening 490 dimensioned to allow passage of hub portion 452 of upper clutch 428 such that hub portion 452 can be rotatably fixed to articulation lever 422. An inner cylindrical portion 492 (FIG. 74) of cover 424 includes cutouts 494. When cover 424 is placed over receptacle 436 of top half section 438*a* of rotatable member 438, cutouts 494 of cylindrical portion 492 of cover 424 receive tabs 440 and cylindrical portion 492 compresses lower clutch 430 against shoulder 436*a* (FIG. 65). Cover 424 can be secured to rotatable member using any known fastening technique including welding, adhesives or any known mechanical attachment structure, e.g., screws, rivets, etc.

Figure 10A:
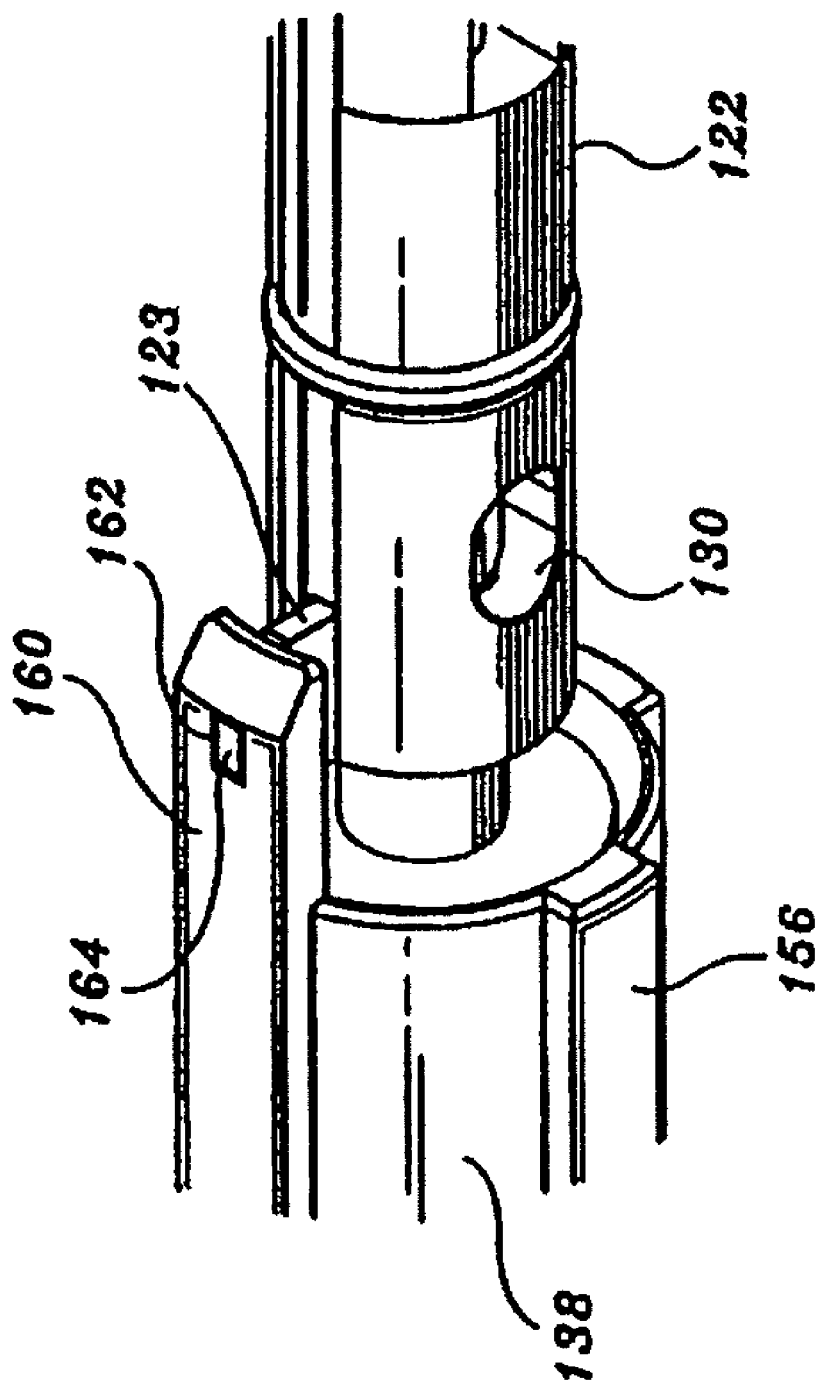
FIG. 10a is a perspective view of the translation member of the articulating mechanism and the proximal end of the elongated body of the surgical stapling apparatus shown in FIG. 1.
Figure 10B:
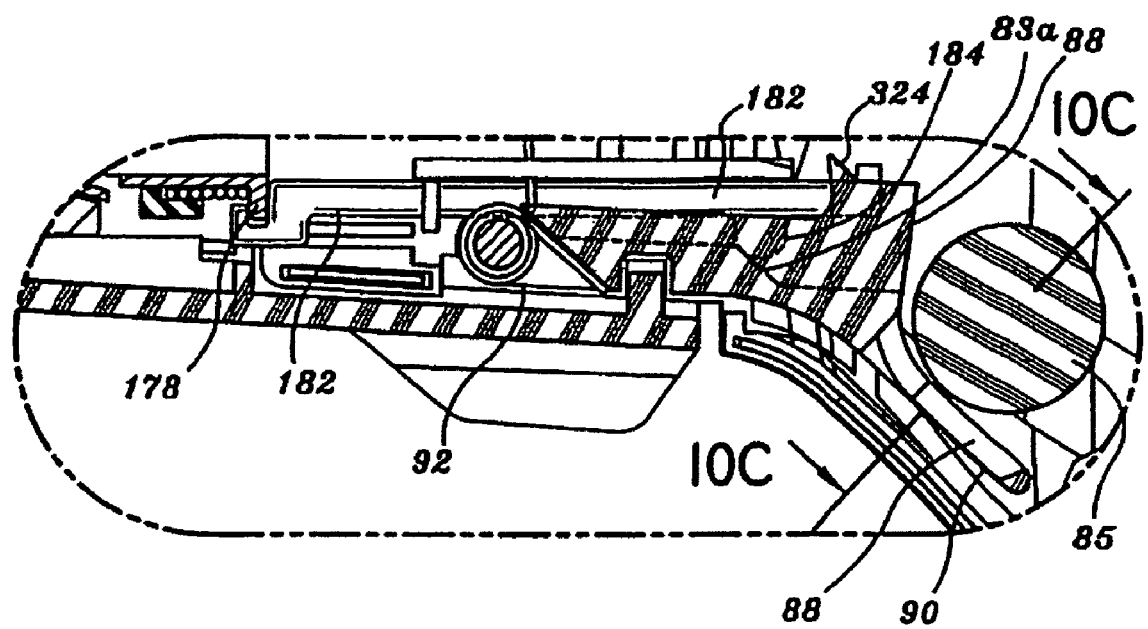
FIG. 10b is an enlarged cross-sectional view of the indicated area of detail of FIG. 8.
Figure 10C:
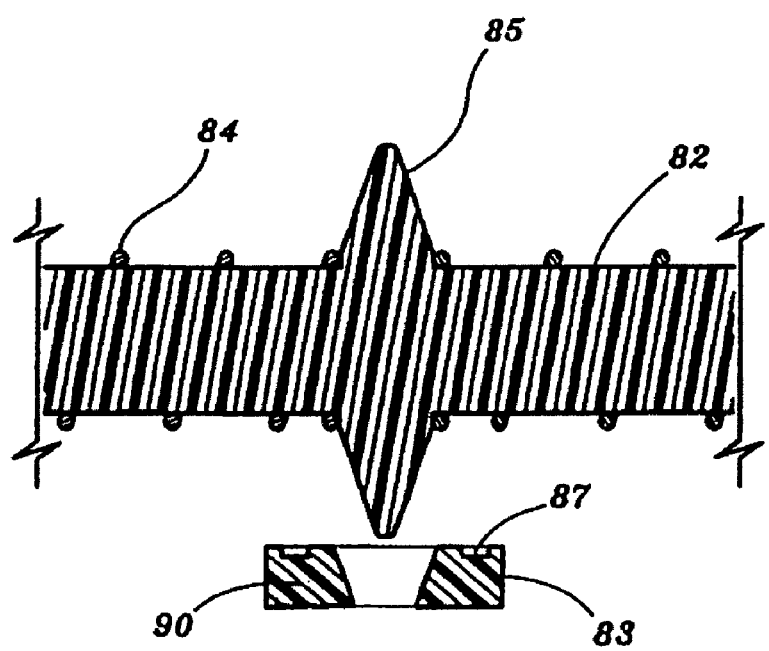
FIG. 10c is a cross-sectional view along section line 10c-10c of FIG. 8.

Referring to FIG. 65, translation member 434 includes an angled body 496 which defines a cam slot 498, a cutout 500 and an arm 502 having engagement structure 504 configured to engage a proximal end of an articulation link 123 (FIG. 10A). Although the engagement structure 504 is illustrated as a finger-like projection other mating engagement structures are envisioned to facilitate connection of translation member 434 to articulation link 123 (FIG. 10A).

Figure 67:
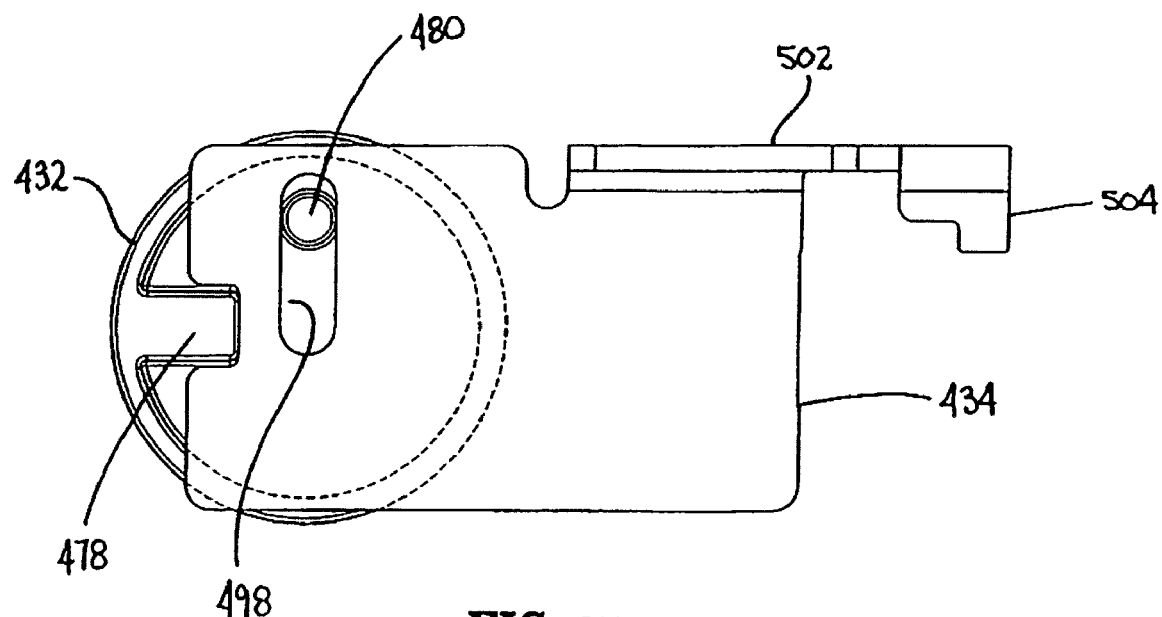
FIG. 67 is a bottom view of the upper clutch and translation member of the articulation mechanism shown in FIG. 65.

Referring also to FIG. 67, cam slot 498 of translation member 434 is dimensioned to slidably receive cam member 480 of main shaft 432. As discussed above, articulation lever 422 is rotatably fixed to upper clutch 428 and upper clutch 428 is rotatably fixed to body portion 474 of main shaft 432. Thus, when articulation lever 422 is rotated, upper clutch 428 and main shaft 432 also rotate to rotate cam member 480 in relation to translation member 434. Although not shown, translation member 434 is confined to linear movement within rotatable member 438. As such, when cam member 480 is driven in rotation, translation member 434 is forced to move linearly within rotatable member 438. Since translation member 438 is fastened to articulation link 123 (FIG. 10A), linear movement of translation member 438 effects linear movement of articulation link 123 to articulate tool assembly 17.

Figure 75:
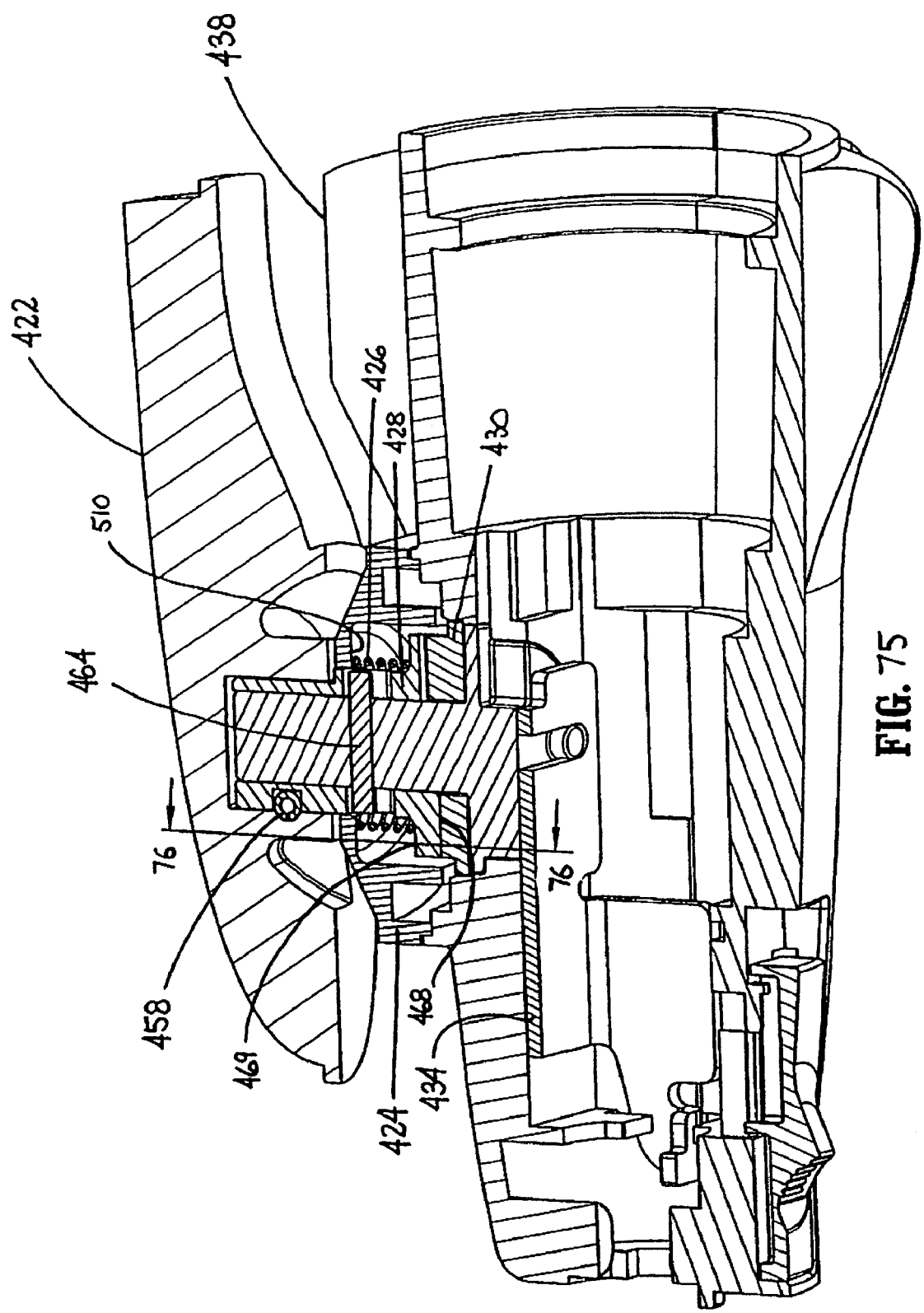
FIG. 75 is a cross-sectional view of the articulation mechanism shown in FIG. 64 with the articulation mechanism in a non-articulated position.
Figure 76:
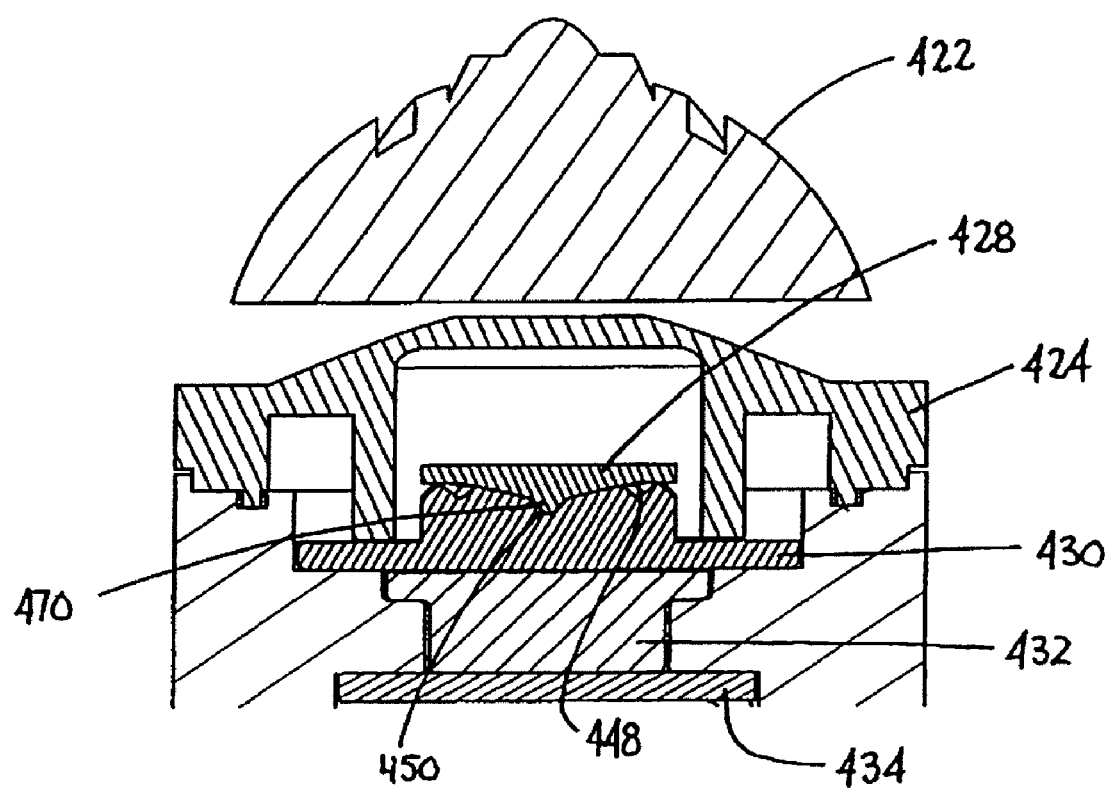
FIG. 76 is a cross-sectional view taken along section lines 76-76 of FIG. 75.
Figure 77:
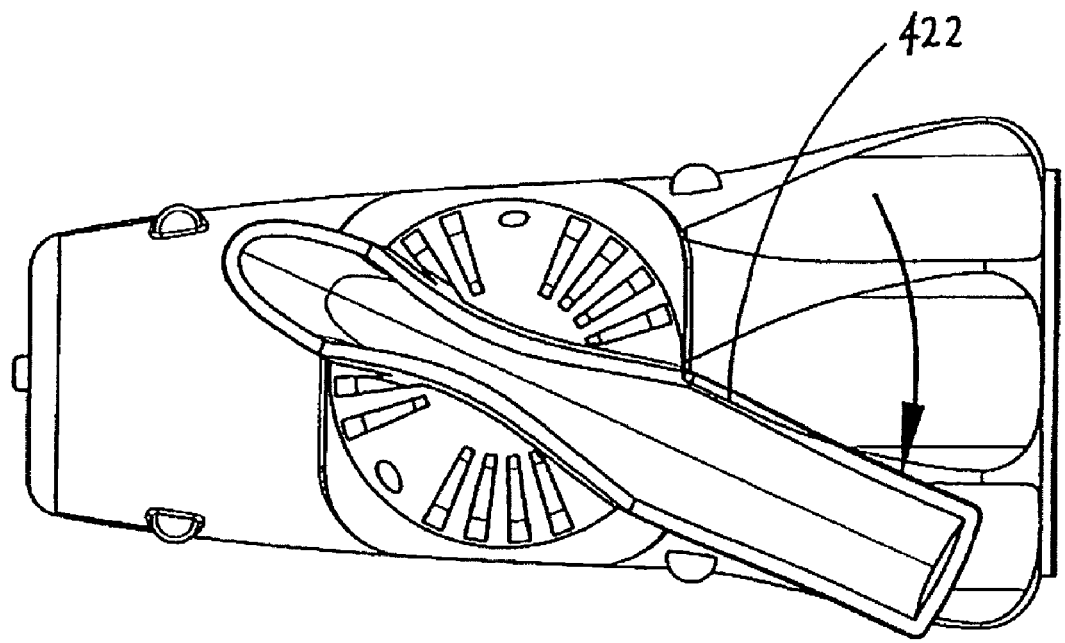
FIG. 77 is a top view of the articulation mechanism shown in FIG. 64 with the articulation lever rotated.
Figure 78:
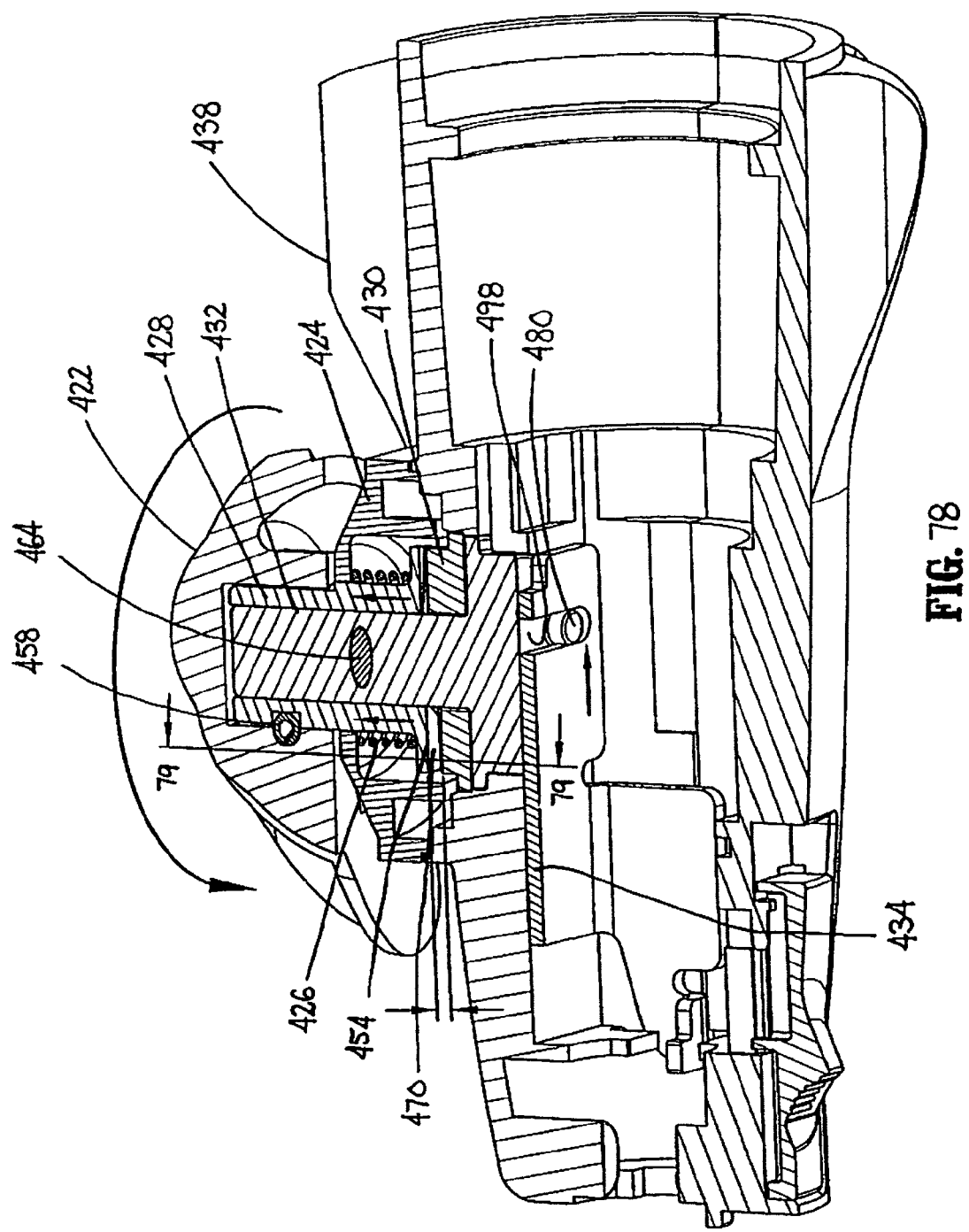
FIG. 78 is a cross-sectional view of the articulation mechanism shown in FIG. 64 with the articulation lever rotated as shown in FIG. 77.

Referring now to FIGS. 65 and 75, biasing member 426 is positioned between upper face 469 of base portion 454 of upper clutch 428 and an inner surface 510 of cover 424. Biasing member urges lower face 468 (FIG. 68) of upper clutch 428 into engagement with serrated portion 444 (FIG. 70) of lower clutch 430 such that spaced projections 470 on upper clutch 428 are received within shallow serrations 448 or deep serrations 450 of lower clutch 430. Engagement between projections 470 and serrations 448 and 450 releasably secure articulation mechanism 420 in a fixed position to thereby releasably secure a tool assembly 17 (FIG. 1) at a fixed angle of articulation. See FIG. 76.

Referring to FIGS. 77-80, when articulation lever 422 is rotated, (as discussed above) upper clutch 428 and main shaft 432 are driven in rotation. When base portion 454 of upper clutch 428 is rotated in relation to serrated portion 444 of lower clutch 428, the triangular projections 470 are driven against angled serrations 448 and 450. When this occurs, upper clutch 428 is urged upwardly against the bias of biasing member 426 (FIG. 78) to disengage projections 470 from serrations 448 or 450 (FIG. 79), to allow rotation of upper clutch 428, and thus, main shaft 432. Thereafter, biasing member 426 urges upper clutch downwardly to urge projection 470 back into engagement with the next serration (FIG. 80). It is noted, projections 470 are positioned to be received within deep serrations 450 when tool assembly 17 (FIG. 1) is in its non-articulated position aligned with body portion 14 (FIG. 1). This provides increased resistance to movement of tool assembly 17 from its non-articulated position. Desirably, the deep serrations 450 correspond to the non-articulated position of the tool assembly 17. However, deep serrations may be incorporated into the mechanism to provide other positions with increased resistance to movement.

Referring to FIGS. 8-10 and 16, a disposable loading unit sensing mechanism extends within stapling apparatus 10 from elongated body 14 into handle assembly 12. The sensing mechanism includes a sensor tube 176 which is slidably supported within bore 26 of elongated body 14. The distal end of sensor tube 176 is positioned towards the distal end of elongated body 14 and the proximal end of sensor tube 176 is secured within the distal end of a sensor cylinder 176 via a pair of nubs 180. The distal end of a sensor link 182 is secured to the proximal end of sensor cylinder 178. Sensor link 182 (See FIGS. 8*a* and 8*c*) has a bulbous end 184 which engages a camming surface 83*a* on pivotable locking member 83. When a disposable loading unit (not shown) is inserted in the distal end of elongated body 14, the disposable loading unit engages the distal end 177 of sensor tube 176 to drive sensor tube 176 proximally, and thereby drive sensor cylinder 178 and sensor link 182 proximally. Movement of sensor link 182 proximally causes bulbous end 184 of sensor link 182 to move distally of camming surface 83*a* to allow locking member 83 to pivot under the bias of spring 92 from a position permitting firing of stapling apparatus 10 to a blocking position, wherein blocking member 83 is positioned to engage actuation shaft 46 and prevent firing of stapling apparatus 10. Sensor link 182 and locking member 83 function to prevent firing of surgical stapling apparatus 10 after a disposable loading unit has been secured to elongated body 14, without first operating firing lockout assembly 80. It is noted that movement of link 182 proximally permits locking member 83 to move to its position shown in FIG. 5.

Referring again to FIGS. 9-12, cam member 136 includes recess 154. A locking ring 184 having a nub portion 186 configured to be received within recess 154 is positioned about sensor cylinder 178 between a control tab portion 188 and a proximal flange portion 190. A spring 192 positioned between flange portion 190 and locking ring 184 urges locking ring distally about sensor cylinder 178. When an articulating disposable loading unit 16*b* having an extended insertion tip 193 is inserted into the distal end of elongated body 14 of stapling apparatus 10, insertion tip 193 causes tab portion 188 to move proximally into engagement with locking ring 184 to urge locking ring 184 and nub 186 proximally of recess 154 in cam member 136 (See FIG. 12*b*). With nub 186 positioned proximally of recess 154, cam member 136 is free to move transversely to effect articulation of stapling apparatus 10. A non-articulating disposable loading unit does not have an extended insertion tip (See FIG. 12*a*). As such, when a non-articulating disposable loading unit is inserted in elongated body 14, sensor cylinder 178 is not retracted proximally a sufficient distance to move nub 186 from recess 154. Thus, cam member 136 is prevented from moving transversely by nub 186 of locking ring 184 which is positioned in recess 154 and articulation lever 30 is locked in its central position.

Figure 16:
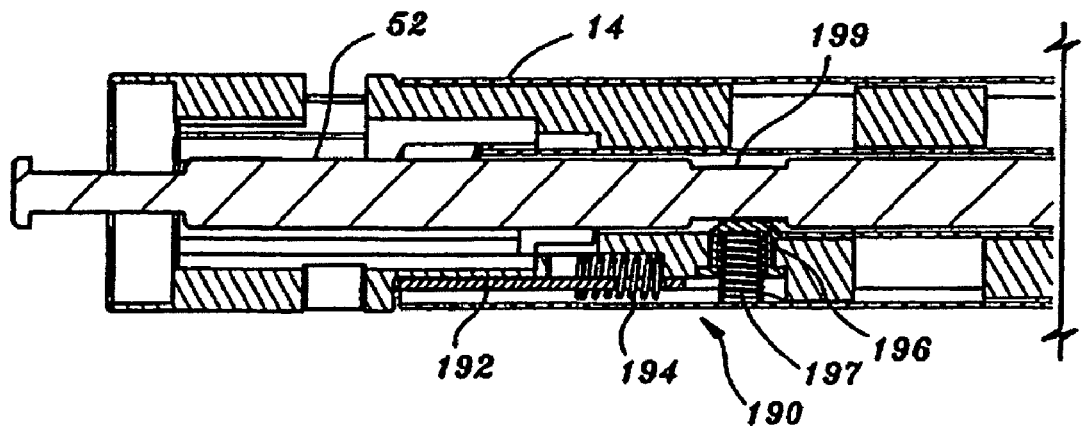
FIG. 16 is an enlarged view of the indicated area of detail shown in FIG. 8.
Figure 17:
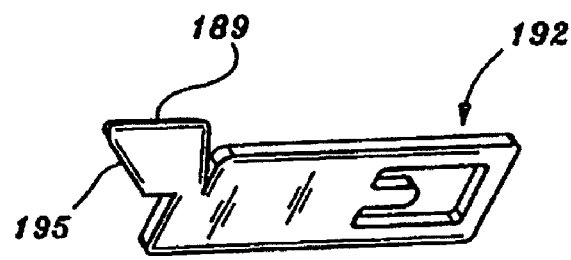
FIG. 17 is a side perspective view of the blocking plate of the surgical stapling apparatus shown in FIG. 1.
Figure 18:
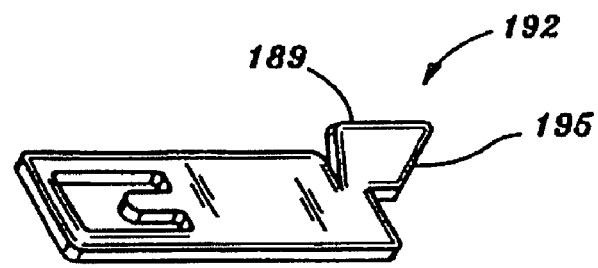
FIG. 18 is a top perspective view of the blocking plate of the surgical stapling apparatus shown in FIG. 1.
Figure 21:
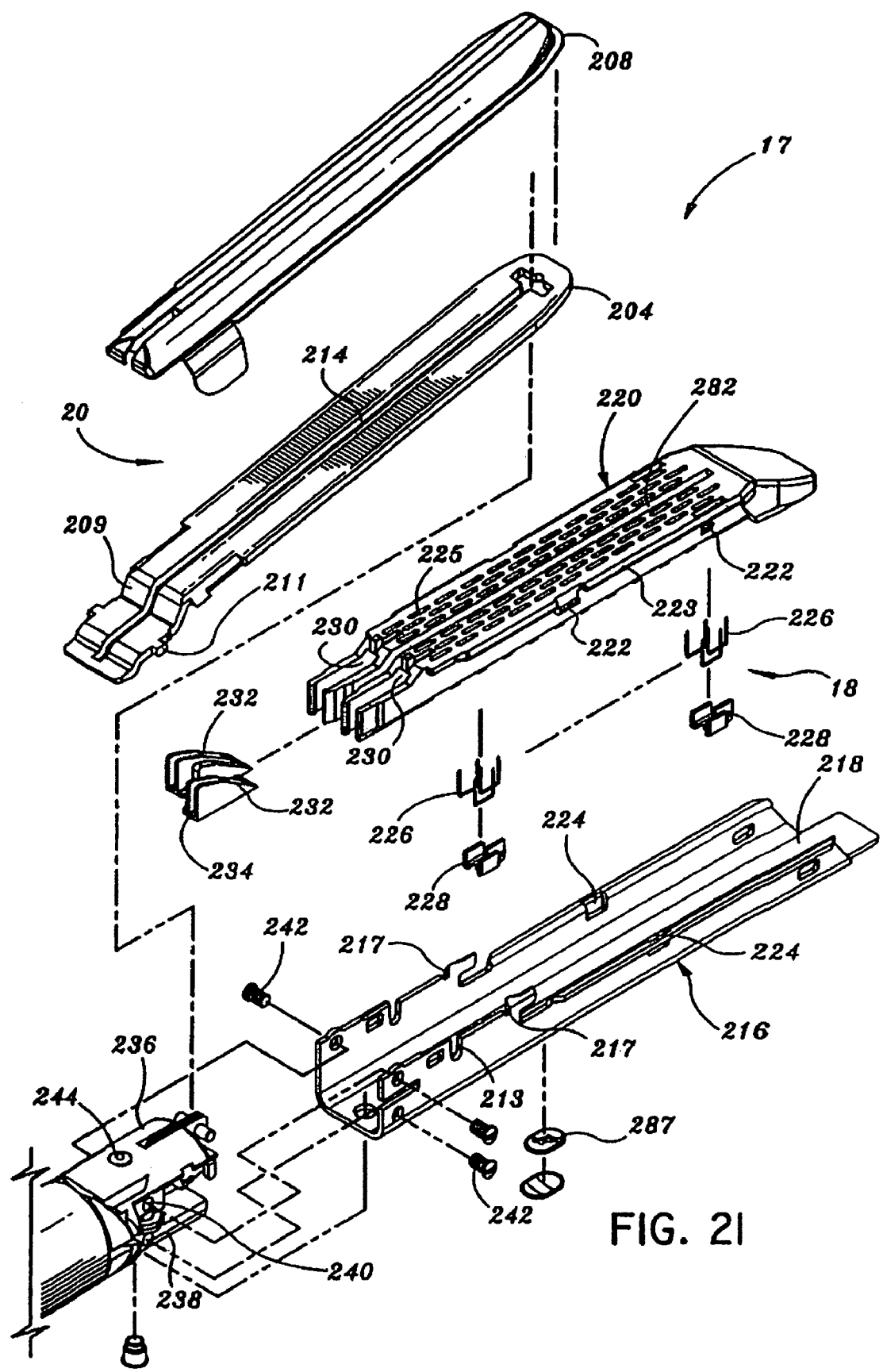
FIG. 21 is a perspective view of the tool assembly of the surgical stapling apparatus of FIG. 1 with parts separated.
Figure 22:
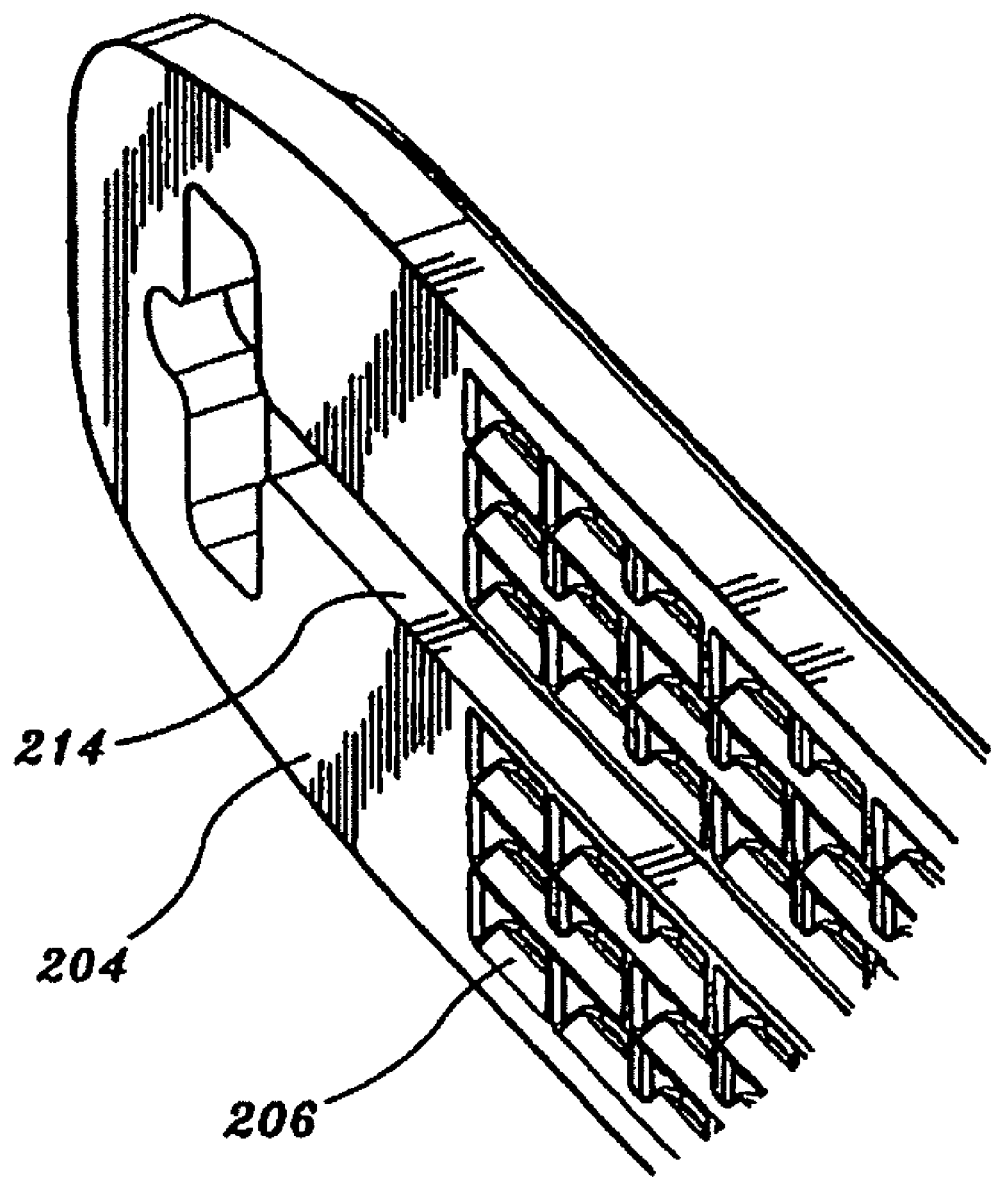
FIG. 22 is an enlarged perspective view of the distal end of the anvil assembly showing a plurality of staple deforming cavities.

Referring to FIGS. 16-18, the distal end of elongated body 14 includes a control rod locking mechanism 190 which is activated during insertion of a disposable loading unit into elongated body 14. Control rod locking mechanism 190 includes a blocking plate 192 which is biased distally by a spring 194 and includes a proximal finger 189 having angled cam surface 195. A semi-circular engagement member 196 is biased transversely towards control rod 52 by a spring 197. Control rod 52 includes an annular recess 199 configured to receive engagement member 196. Blocking plate 192 is movable from a distal position spaced from engagement member 196 to a proximal position located behind engagement member 196. In the proximal position, engagement member 196 is prevented from being biased from recess 199 by engagement with blocking plate 192. During insertion of a disposable loading unit 16 (See FIG. 1) into the distal end of elongated body 14, as will be described in further detail below, cam surface 195 of blocking plate 192 is engaged by a nub 254 (FIG. 30) on the disposable loading unit 16 as the disposable loading unit is rotated into engagement with elongated body 14 to urge plate 192 to the proximal position. Engagement member 196, which is positioned within recess 199, is retained therein by blocking plate 192 while nub 254 engages cam surface 195 to prevent longitudinal movement of control rod 52 during assembly. When the disposable loading unit 16 is properly positioned with respect to the elongated body 14, nub 254 on the proximal end of the disposable loading unit 16 passes off cam surface 195 allowing spring 194 to return blocking plate 192 to its distal position to permit subsequent longitudinal movement of control rod 52. It is noted that when the disposable loading unit nub passes off cam surface 195, an audible clicking sound is produced indicating that the disposable loading unit 16 is properly fastened to the elongated body 14.

Referring to FIGS. 19 and 20, disposable loading unit 16 includes a proximal housing portion 200 adapted to releasably engage the distal end of body portion 14 (FIG. 1). A mounting assembly 202 is pivotally secured to the distal end of housing portion 200, and is configured to receive the proximal end of tool assembly 17 such that pivotal movement of mounting assembly 202 about an axis perpendicular to the longitudinal axis of housing portion 200 effects articulation of tool assembly 17.

Referring to FIGS. 21-26, tool assembly 17 preferably includes anvil assembly 20 and cartridge assembly 18. Anvil assembly 20 includes anvil portion 204 having a plurality of staple deforming concavities 206 (FIG. 22) and a cover plate 208 secured to a top surface of anvil portion 204 to define a cavity 210 (FIG. 24) therebetween. Cover plate 208 is provided to prevent pinching of tissue during clamping and firing of stapling apparatus 10. Cavity 210 is dimensioned to receive a distal end of an axial drive assembly 212 (See FIG. 27). A longitudinal slot 214 extends through anvil portion 204 to facilitate passage of retention flange 284 of axial drive assembly 212 into the anvil cavity 210. A camming surface 209 formed on anvil portion 204 is positioned to engage axial drive assembly 212 to facilitate clamping of tissue 198. A pair of pivot members 211 formed on anvil portion 204 are positioned within slots 213 formed in carrier 216 to guide the anvil portion between the open and clamped positions. A pair of stabilizing members 215 engage a respective shoulder 217 formed on carrier 216 to prevent anvil portion 204 from sliding axially relative to staple cartridge 220 as camming surface 209 is deformed.

Cartridge assembly 18 includes a carrier 216 which defines an elongated support channel 218. Elongated support channel 218 is dimensioned and configured to receive a staple cartridge 220. Corresponding tabs 222 and slots 224 formed along staple cartridge 220 and elongated support channel 218 function to retain staple cartridge 220 within support channel 218. A pair of support struts 223 formed on staple cartridge 220 are positioned to rest on side walls of carrier 216 to further stabilize staple cartridge 220 within support channel 218.

Staple cartridge 220 includes retention slots 225 for receiving a plurality of fasteners 226 and pushers 228. A plurality of spaced apart longitudinal slots 230 extend through staple cartridge 220 to accommodate upstanding cam wedges 232 of actuation sled 234. A central longitudinal slot 282 extends along the length of staple cartridge 220 to facilitate passage of a knife blade 280. During operation of surgical stapler 10, actuation sled 234 translates through longitudinal slots 230 of staple cartridge 220 to advance cam wedges 232 into sequential contact with pushers 228, to cause pushers 228 to translate vertically within slots 224 and urge fasteners 226 from slots 224 into the staple deforming cavities 206 of anvil assembly 20.

Figure 27:
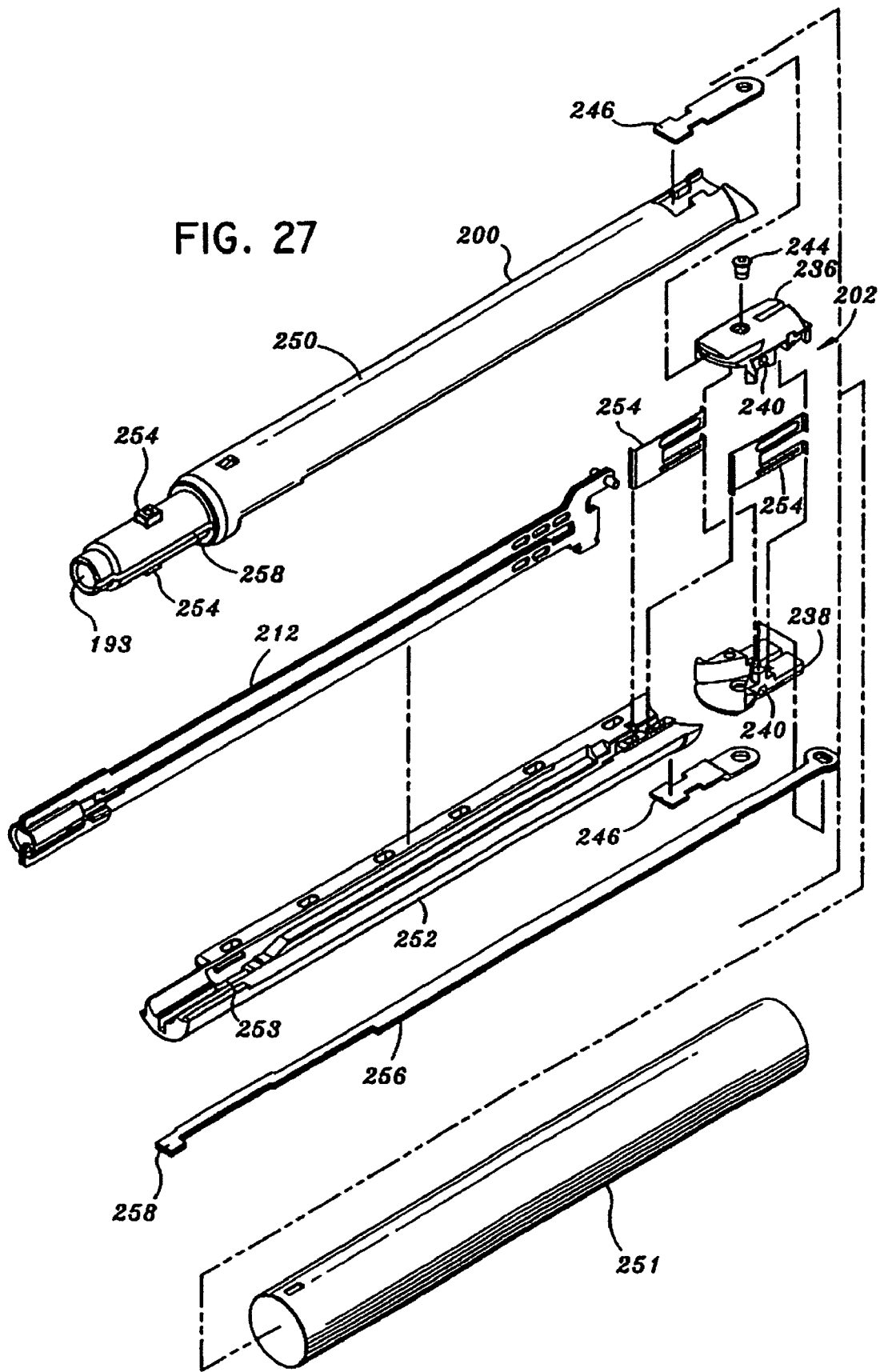
FIG. 27 is an enlarged perspective view with parts separated of the proximal housing portion and mounting assembly of the disposable loading unit shown in FIG. 19.
Figure 31:
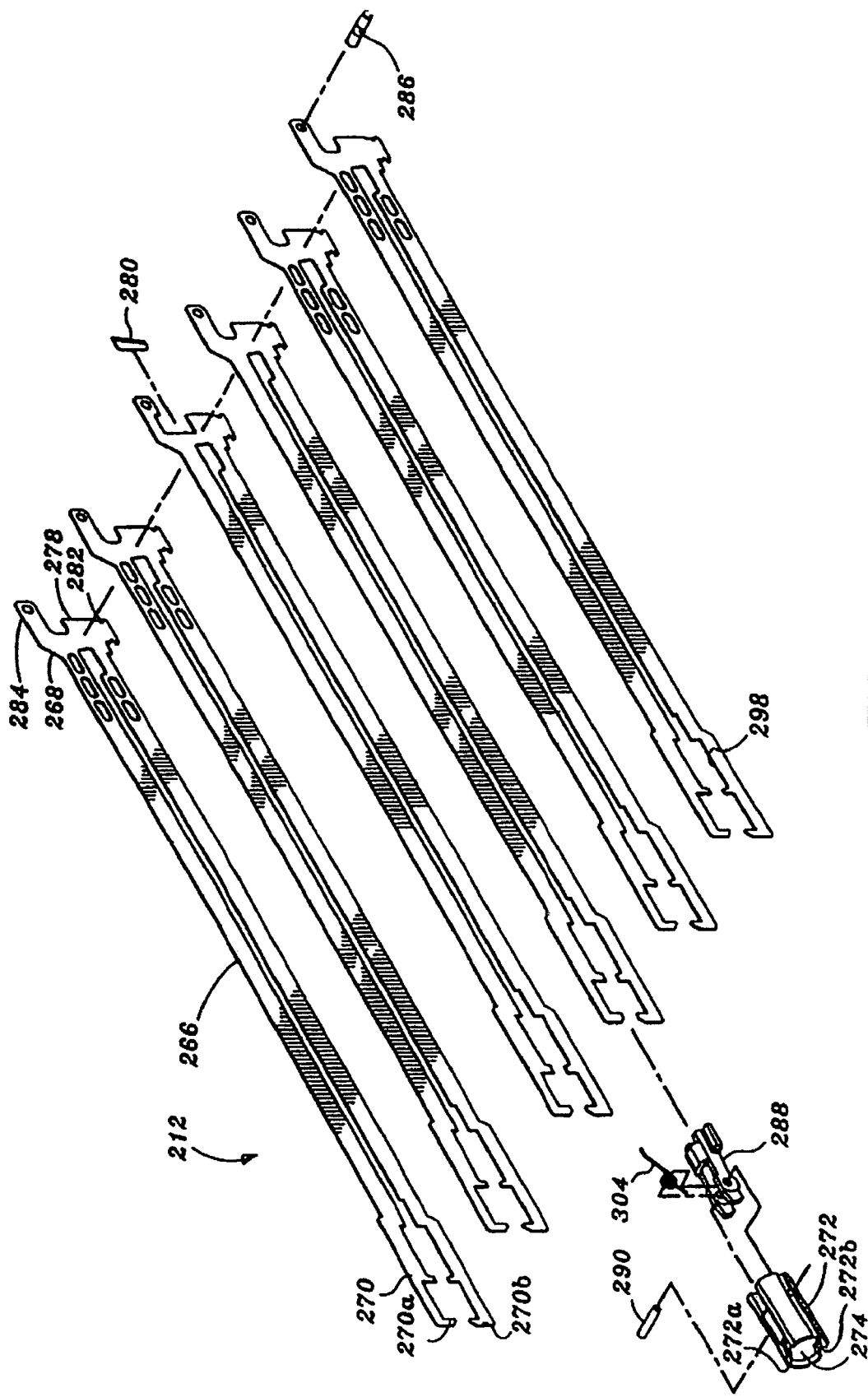
FIG. 31 is a perspective view with parts separated of the axial drive assembly.

Referring to FIGS. 27 and 28, mounting assembly 202 includes upper and lower mounting portions 236 and 238. Each mounting portion includes a threaded bore 240 on each side thereof dimensioned to receive threaded bolts 242 (See FIG. 21) for securing the proximal end of carrier 216 thereto. A pair of centrally located pivot members 244 (See FIG. 21) extends between upper and lower mounting portions via a pair of coupling members 246 which engage the distal end of housing portion 200. Coupling members 246 each include an interlocking proximal portion 248 configured to be received in grooves 250 formed in the proximal end of housing portion 200 to retain mounting assembly 202 and housing portion 200 in a longitudinally fixed position in relation thereto.

Housing portion 200 of disposable loading unit 16 includes an upper housing half 250 and a lower housing half 252 contained within an outer casing 251. The proximal end of housing half 250 includes engagement nubs 254 for releasably engaging elongated body 14 and an insertion tip 193. Nubs 254 form a bayonet type coupling with the distal end of body 14 which will be discussed in further detail below. Housing halves 250 and 252 define a channel 253 for slidably receiving axial drive assembly 212. A second articulation link 256 is dimensioned to be slidably positioned within a slot 258 formed between housing halves 250 and 252. A pair of blow out plates 254 are positioned adjacent the distal end of housing portion 200 adjacent the distal end of axial drive assembly 212 to prevent outward bulging of drive assembly 212 during articulation of tool assembly 17.

Referring to FIGS. 29-30, second articulation link 256 includes at least one elongated metallic plate. Preferably, two or more metallic plates are stacked to form link 256. The proximal end of articulation link 256 includes a hook portion 258 configured to engage first articulation link 123 (See FIG. 9) and the distal end includes a loop 260 dimensioned to engage a projection 262 formed on mounting assembly 202. Projection 262 is laterally offset from pivot pin 244 such that linear movement of second articulation link 256 causes mounting assembly 202 to pivot about pivot pins 244 to articulate tool assembly 17.

Figure 35:
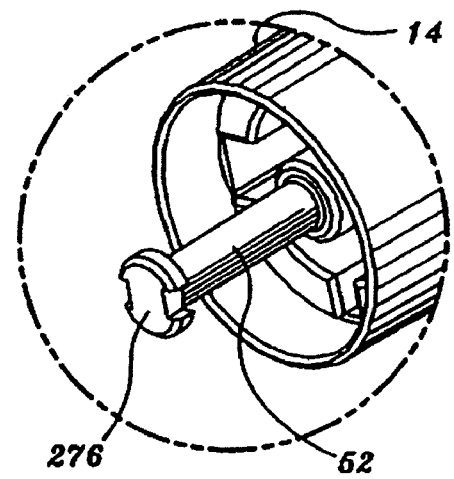
FIG. 35 is an enlarged perspective view of the distal end of the elongated body of the stapling apparatus shown in FIG. 1.
Figure 36:
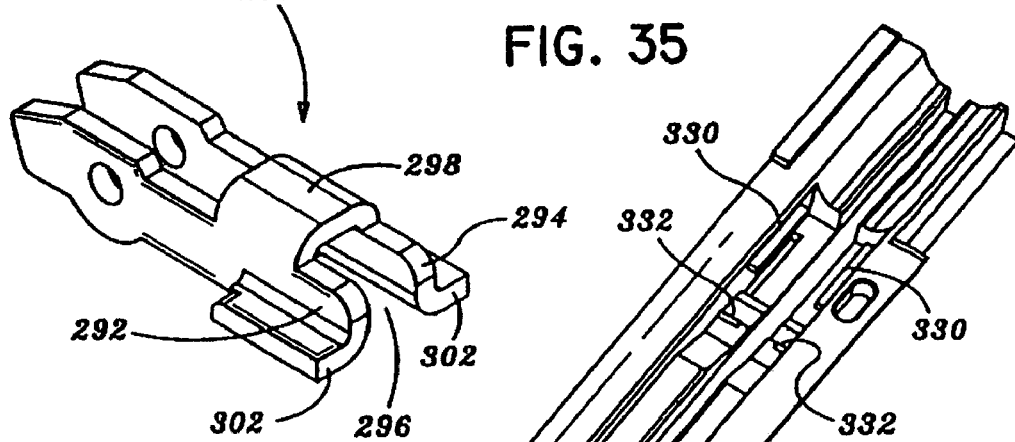
FIG. 36 is an enlarged perspective view of the locking device shown in FIG. 33.

Referring also to FIGS. 31-34, axial drive assembly 212 includes an elongated drive beam 266 including a distal working head 268 and a proximal engagement section 270. Drive beam 266 may be constructed from a single sheet of material or, preferably, multiple stacked sheets. Engagement section 270 includes a pair of engagement fingers 270a and 270b which are dimensioned and configured to mountingly engage a pair of corresponding retention slots 272a and 272b formed in drive member 272. Drive member 272 includes a proximal porthole 274 configured to receive the distal end 276 of control rod 52 (See FIG. 35) when the proximal end of disposable loading unit 16 is engaged with elongated body 14 of surgical stapling apparatus 10.

The distal end of drive beam 266 is defined by a vertical support strut 278 which supports a knife blade 280, and an abutment surface 283 which engages the central portion of actuation sled 234 during a stapling procedure. Surface 285 at the base of surface 283 is configured to receive a support member 287 slidably positioned along the bottom of the staple cartridge 220. Knife blade 280 is positioned to translate slightly behind actuation sled 234 through a central longitudinal slot 282 in staple cartridge 220 (FIG. 30) to form an incision between rows of stapled body tissue. A retention flange 284 projects distally from vertical strut 278 and supports a cylindrical cam roller 286 at its distal end. Cam roller 286 is dimensioned and configured to engage cam surface 209 on anvil body 204 to clamp anvil portion 204 against body tissue.

Referring also to FIGS. 36-39, a locking device 288 is pivotally secured to drive member 270 about a pivot pin 290. Locking device 288 includes a pair of elongate glides 292 and 294 which define a channel 296. A web 298 joins a portion of the upper surfaces of glides 292 and 294, and is configured and dimensioned to fit within elongated slot 298 formed in drive beam 266 at a position distal of drive member 270. Horizontal cams 300 and 302 extend from glides 292 and 294 respectively, and are accommodated along an inner surface of lower housing half 252. As best shown in FIG. 42, a torsion spring 304 is positioned adjacent drive member 270 and engages horizontal cams 300 and 302 of locking device 288 to normally bias locking device 288 downward toward lower housing half 252 onto ledge 310. Locking device 288 translates through housing portion 200 with axial drive assembly 212. Operation of locking device 288 will be described below.

Sequence of Operation

Referring to FIGS. 40-44, to use stapling instrument 10, a disposable loading unit 16 is first secured to the distal end of elongated body 14. As discussed above, stapling instrument 10 can be used with articulating and non-articulating disposable loading units having linear rows of staples between about 30 mm and about 60 mm. To secure disposable loading unit 16 to elongated body 14, the distal end 276 of control rod 52 is inserted into insertion tip 193 of disposable loading unit 16, and insertion tip 193 is slid longitudinally into the distal end of elongated body 14 in the direction indicated by arrow "A" in FIG. 41 such that hook portion 258 of second articulation link 256 slides within a channel 310 in elongated body 314. Nubs 254 will each be aligned in a respective channel (not shown) in elongated body 14. When hook portion 258 engages the proximal wall 312 of channel 310, disposable loading unit 16 is rotated in the direction indicated by arrow "B" in FIGS. 41-44 to move hook portion 258 of second articulation link 256 into engagement with finger 164 of first articulation link 123. Nubs 254 also forms a bayonet type coupling within annular channel 314 in body 14. During rotation of loading unit 16, nubs 254 engage cam surface 195 (FIG. 41) of block plate 192 to initially move plate 192 in the direction indicated by arrow "C" in FIGS. 41 and 43 to lock engagement member 196 in recess 199 of control rod 52 to prevent longitudinal movement of control rod 52 during attachment of disposable loading unit 16. During the final degree of rotation, nubs 254 disengage from cam surface 195 to allow blocking plate 192 to move in the direction indicated by arrow "D" in FIGS. 42 and 44 from behind engagement member 196 to once again permit longitudinal movement of control rod 52.

Figure 43A:
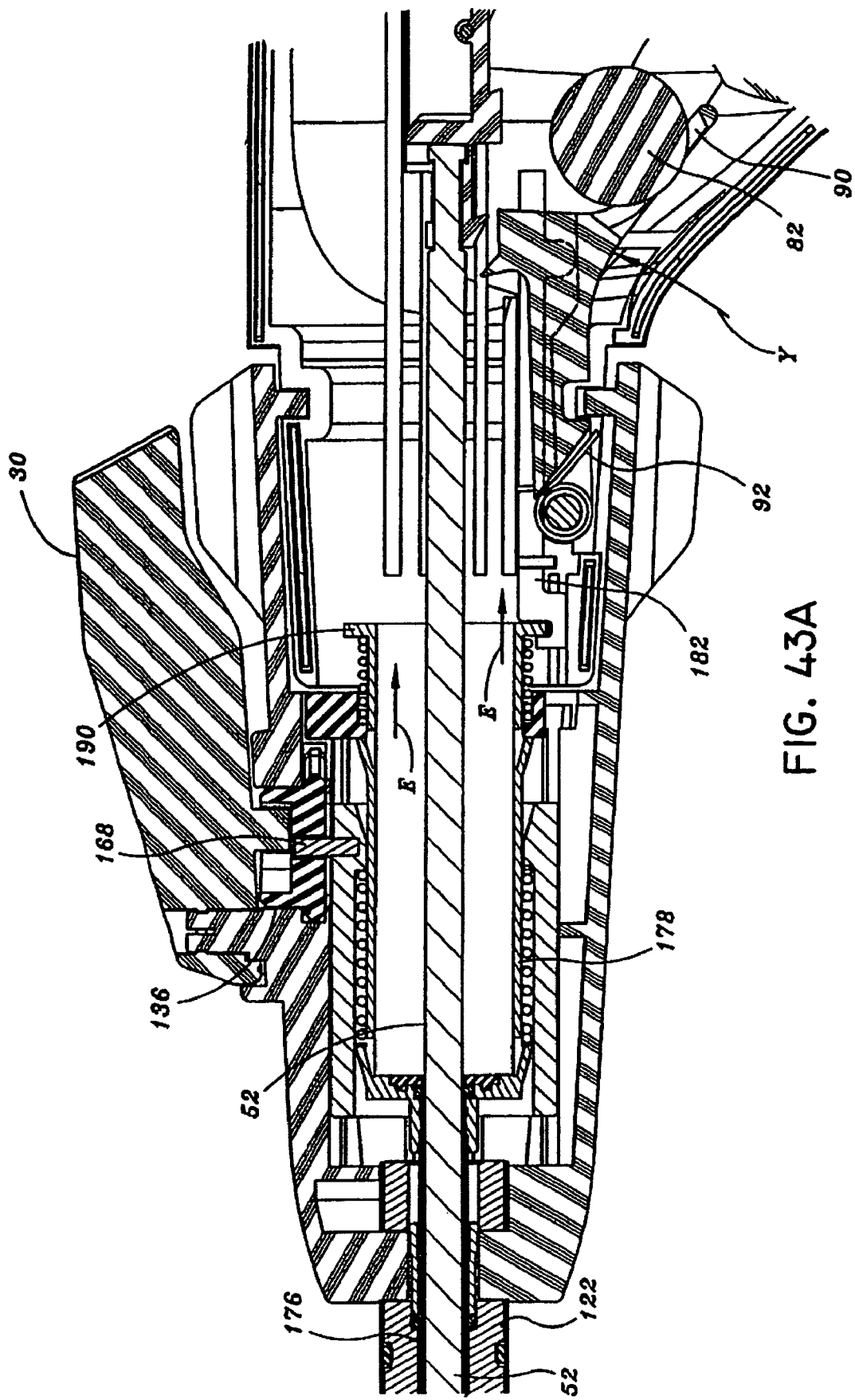
FIG. 43a is a side cross-sectional view of the rotation knob, articulation mechanism, and sensing mechanism during insertion of a disposable loading unit into the elongated body of the surgical stapling apparatus.

Referring to FIGS. 43 and 43a, when insertion tip 193 engages the distal end of sensor tube 176, the disposable loading unit sensing mechanism is actuated. Insertion tip 193 engages and moves sensor tube 176 proximally in the direction indicated by arrow "E" in FIG. 43. As discussed above, proximal movement of sensor tube 176 effects proximal movement of sensor cylinder 178 and sensor link 182 in the direction indicated by arrow "E" in FIG. 43a to pivot locking member 83 counter-clockwise, as indicated by arrow "Y" in FIG. 43a, from a non-blocking position to a position blocking movement of actuation shaft 46.

Figure 45:
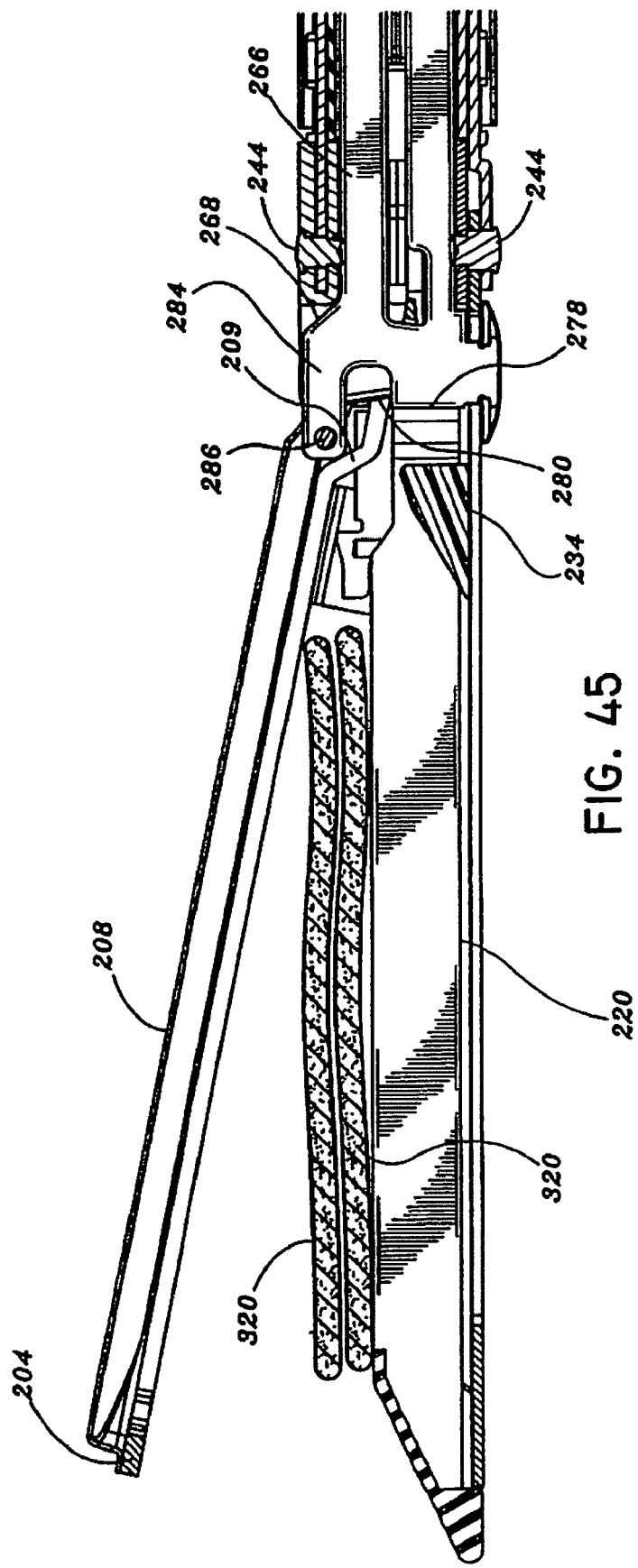
FIG. 45 is a side cross-sectional view of the distal end of the disposable loading unit of FIG. 1 with tissue positioned between the anvil and clamp assemblies.
Figure 46:
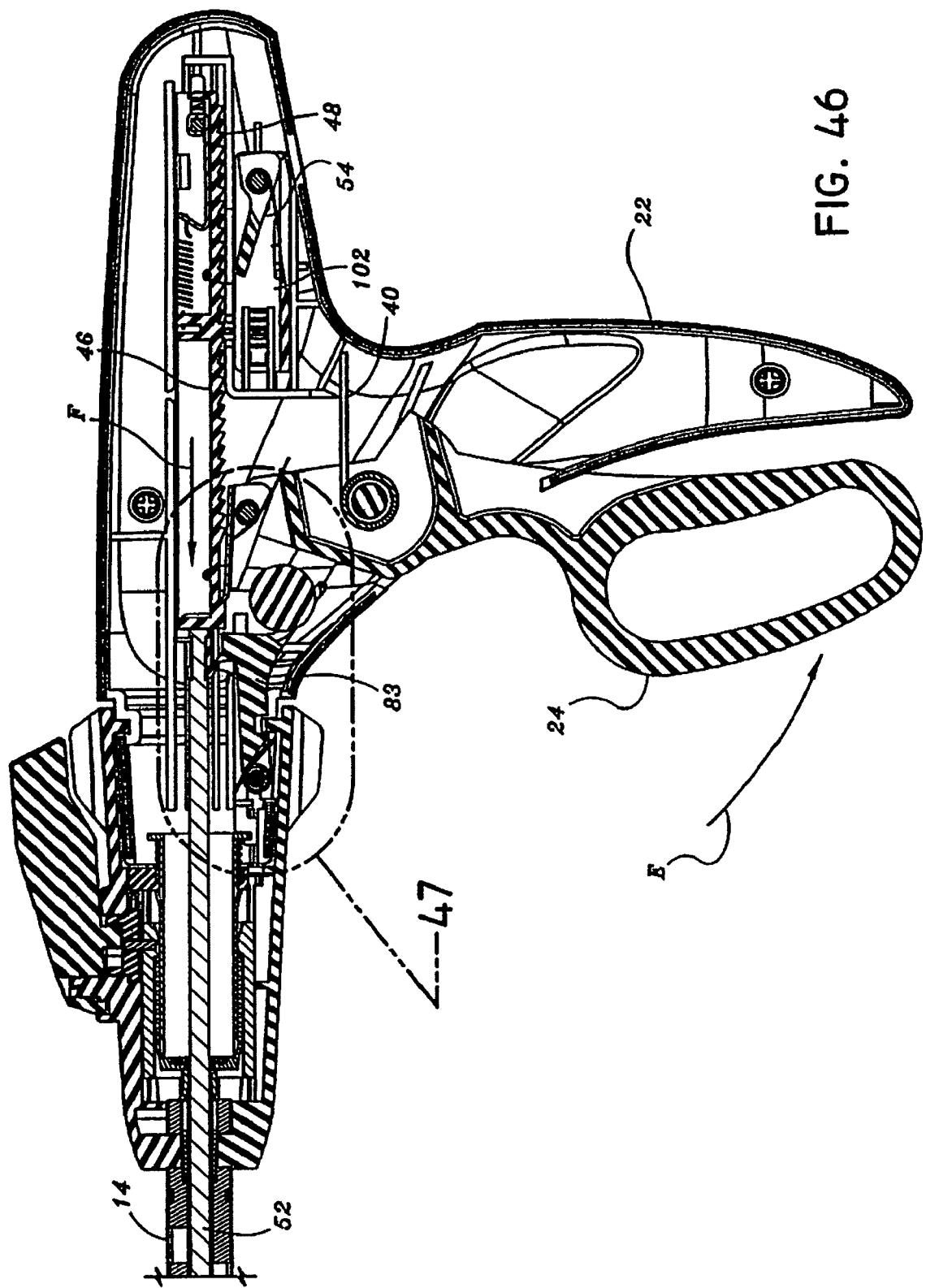
FIG. 46 is a side cross-sectional view of the handle assembly with the movable handle in an actuated position.
Figure 47:
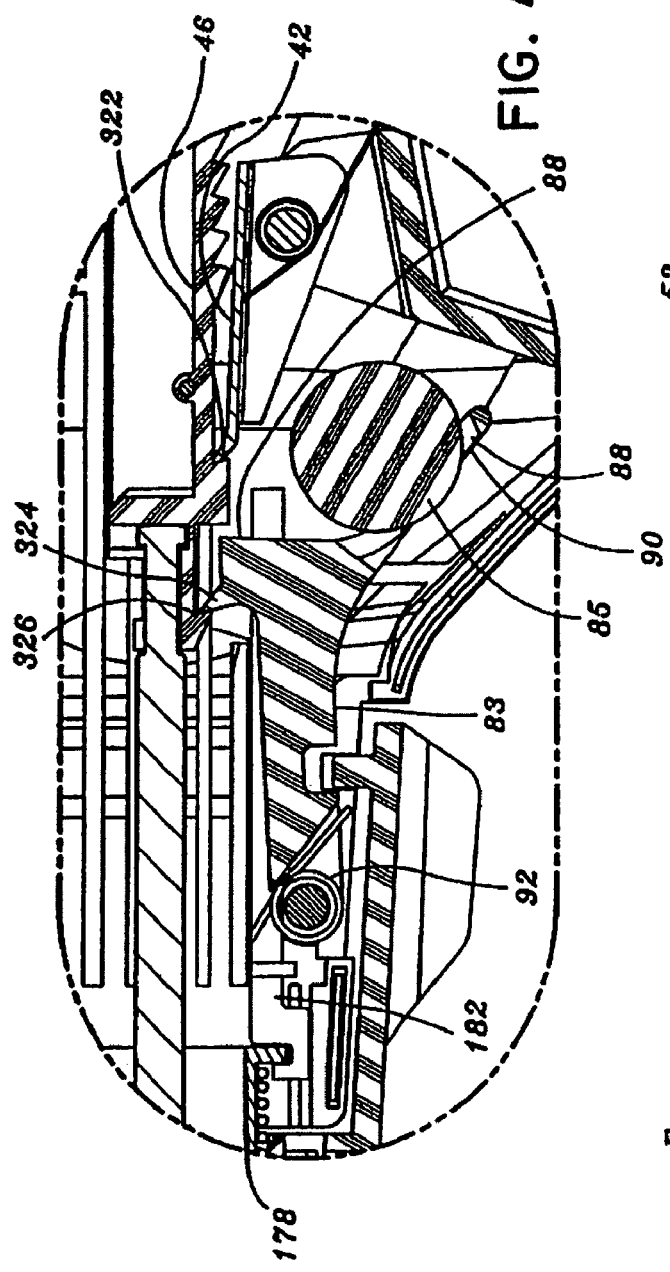
FIG. 47 is an enlarged view of the indicated area of detail shown in FIG. 46.
Figure 48:
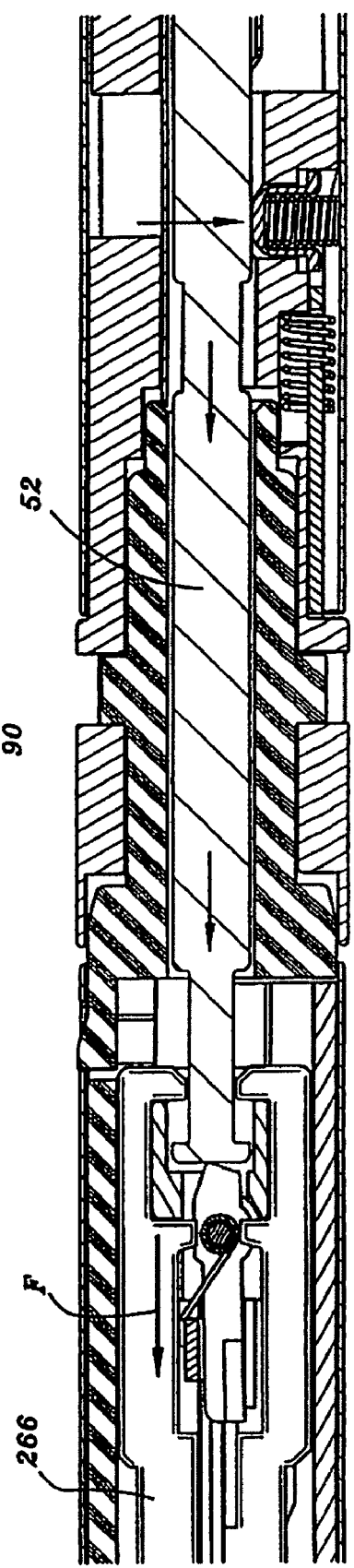
FIG. 48 is a cross-sectional view of the proximal end of the disposable loading unit of FIG. 19 and the distal end of the elongated body of the surgical stapling apparatus shown in FIG. 1 with the control rod in a partially advanced position.
Figure 49:
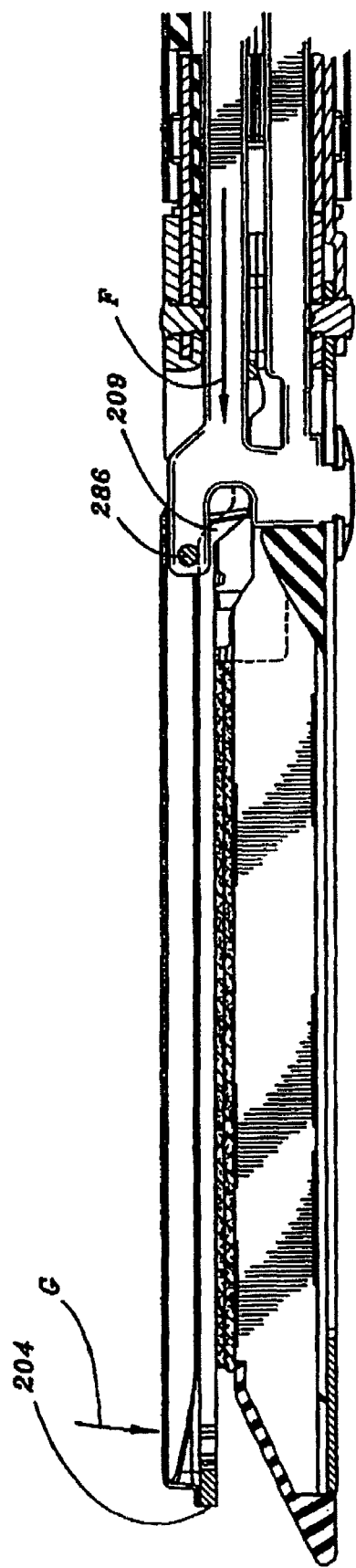
FIG. 49 is a cross-sectional view of the tool assembly of the surgical stapling apparatus shown in FIG. 1 positioned about tissue in the clamped position.

Referring to FIGS. 46-49, with a disposable loading unit attached to stapling instrument 10, tool assembly 17 can be positioned about tissue 320 (FIG. 45). To clamp tissue between anvil assembly 20 and cartridge assembly 18, stationary handle 24 is moved in the direction indicated by arrow "E" in FIG. 46 against the bias of torsion spring 40 to move driving pawl 42 into engagement with shoulder 322 on actuation shaft 46. Engagement between shoulder 322 and driving pawl 42 advances actuation shaft 46 and thus advances control rod 52 distally. Control rod 52 is connected at its distal end to axial drive assembly 212 (FIG. 48), including drive beam 266, such that distal movement of control rod 52 effects distal movement of drive beam 266 in the direction indicated by arrow "F" in FIGS. 48 and 49, moving cam roller 286 into engagement with cam surface 209 on anvil portion 204 to urge anvil portion 204 in the direction indicated by arrow "G" in FIG. 49. It is noted that one complete stroke of movable handle 24 advances actuation shaft 46 approximately 15 mm which is sufficient to clamp tissue during the first stroke but not to fire staples.

As discussed above with respect to the anti-reverse clutch mechanism, during the first (clamping) stroke of movable handle 24, slide plate 102 (FIG. 46) prevents locking pawl 54 from engaging toothed rack 48. To maintain actuation shaft 46 in its longitudinal position after handle 24 is released, an engagement member 324 (FIG. 47) is provided on locking member 83 to engage shoulder 326 on actuation shaft 46 and retain shaft 46 in its longitudinal position (See FIG. 47). Upon release of movable handle 24, drive pawl 42 moves over rack 48 as torsion spring 40 returns handle 24 to a position spaced from stationary handle 22. In this position, driving pawl 42 is urged into engagement with toothed rack 48 to retain actuation shaft 46 in its longitudinal fixed position.

In order to fire staples, movable handle 24 is actuated again, i.e., moved through another stroke. As discussed above, stapling apparatus 10 is capable of receiving disposable loading units having linear rows of staples of between about 30 mm and about 60 mm. Since each stroke of the movable handle 24 preferably advances actuation shaft 46 15 mm, and one stroke is required to clamp tissue, the movable handle must be actuated (n+1) strokes to fire staples, where n is the length of the linear rows of staples in the disposable loading unit attached to stapling instrument 10 divided by 15 mm.

Figure 50:
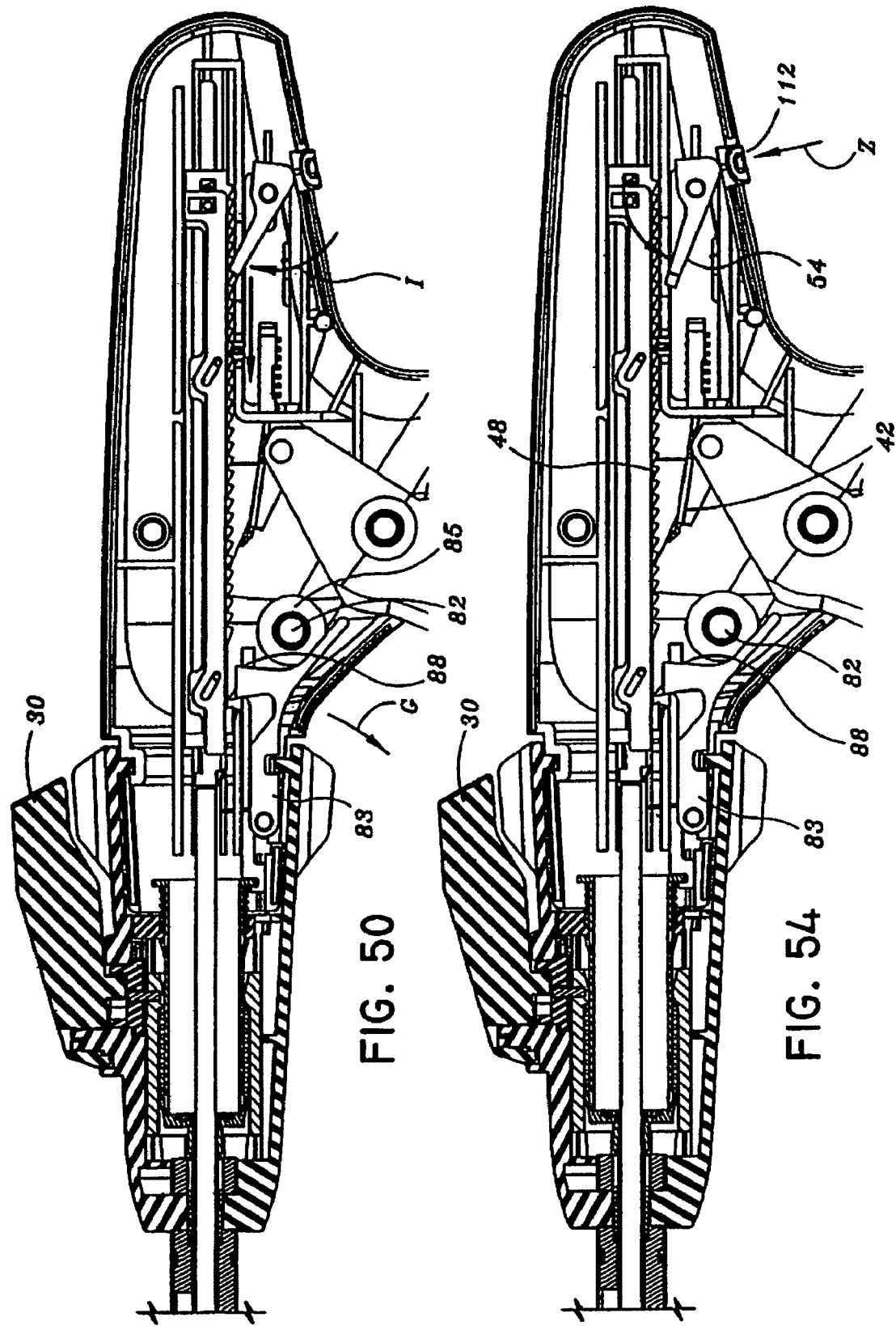
FIG. 50 is a cross-sectional view of the handle assembly of the stapling apparatus of FIG. 1 during the clamping stroke of the apparatus.

Referring to FIG. 50, prior to being able to fire staples, firing lockout assembly 80 (FIG. 4) must be actuated to move locking surface 88 from its blocking position (FIG. 47) to a non-blocking position. This is accomplished by pressing down on plunger 82 to move camming surface 85 into engagement with sidewalls of slot 89 of locking member 83 to pivot locking member 83 in the direction indicated by arrow "G" in FIG. 50 (see also FIG. 5). Thereafter, movable handle 24 may be actuated an appropriate number of strokes to advance actuation shaft 46, and thus control rod 52 and drive beam 266, distally in the direction indicated by arrow "H" in FIGS. 51 and 52 to advance actuation sled 234 through staple cartridge 220 to effect ejection of staples. It is noted that after the first or clamping stroke of movable handle 54 (during the second stroke), slide 102 passes over locking pawl 54 allowing torsion spring 56 to move locking pawl 54 in the direction indicated by arrow "I" in FIG. 50 into engagement with toothed rack 48 to retain actuation shaft 46 in its longitudinal position.

Figure 53:
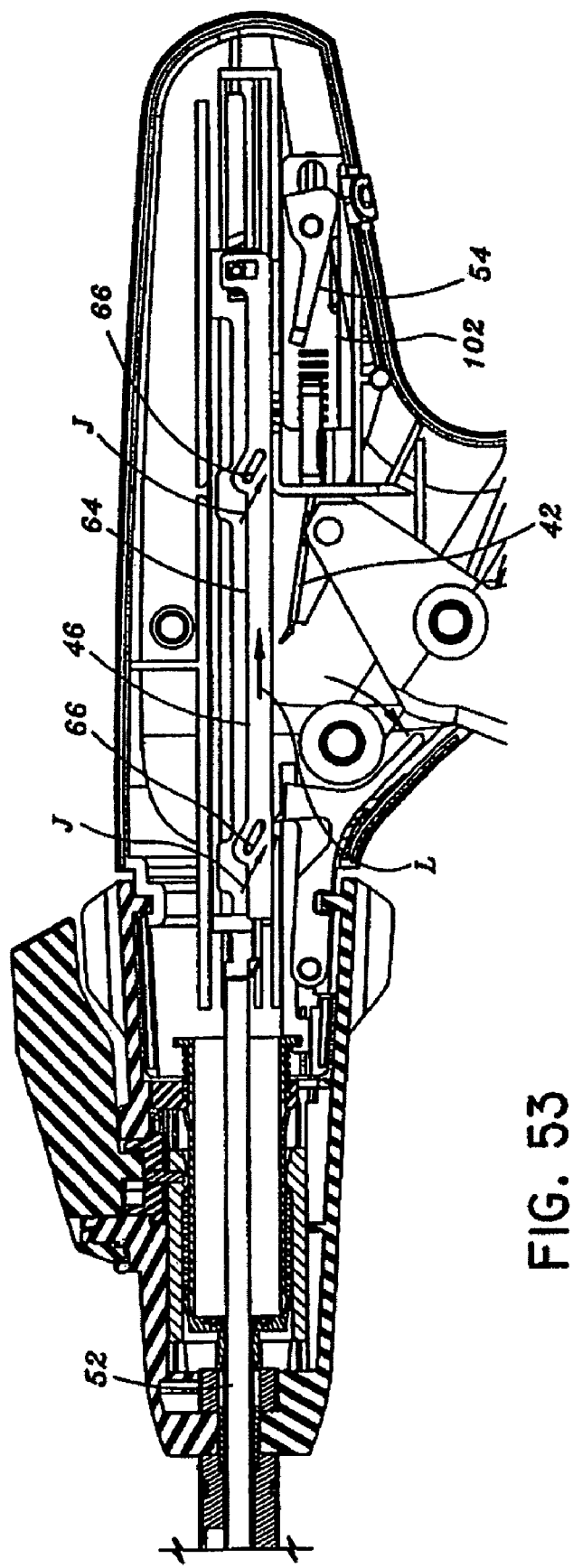
FIG. 53 is a side cross-sectional view of the handle assembly of the apparatus during retraction of the actuation shaft.

Referring to FIG. 53, to retract actuation shaft 46 and thus control rod 52 and drive member 266 after firing staples, retraction knobs 32 (see FIG. 1) are pulled proximally causing pins 66 to move release plate 64 in the direction indicated by arrow "J" in FIG. 53 over teeth 48 to disengage drive pawl 42 from engagement with teeth 48. As discussed above, with respect to the anti-reverse clutch mechanism, locking pawl 54 is urged by slide plate 102 out of engagement with toothed rack 48 (not shown) to permit actuation shaft 46 to be moved proximally, in the direction indicated by arrow "L", after drive pawl 42 is disengaged from teeth 48.

Referring to FIG. 54, in order to retract actuation shaft 46 prior to firing stapling apparatus, i.e., when locking pawl is currently engaged with toothed racked 48, emergency return button 112 is pushed in the direction indicated by arrow "Z" in FIG. 54 to disengage locking pawl 54 from toothed rack 48. Retraction knobs 32 (FIG. 1) must also be concurrently pulled rearwardly, as discussed above, to release drive pawl 42 from rack 48.

Figure 55:
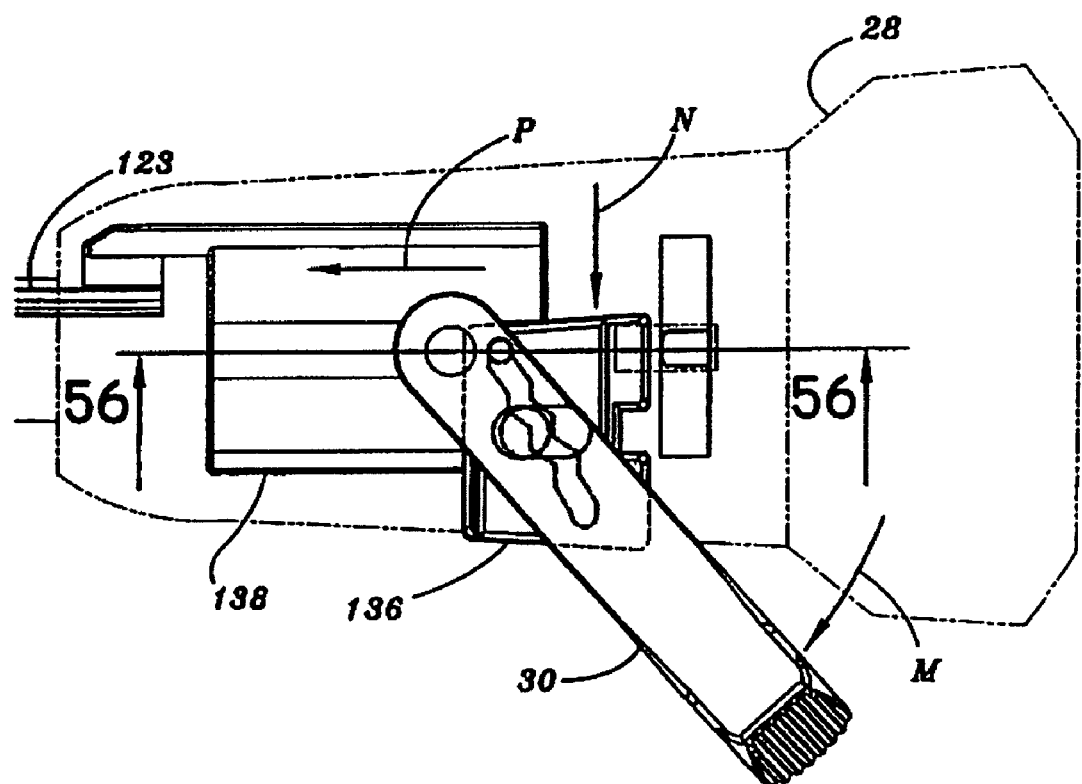
FIG. 55 is a top view of the articulation mechanism of the surgical stapling apparatus.
Figure 56:
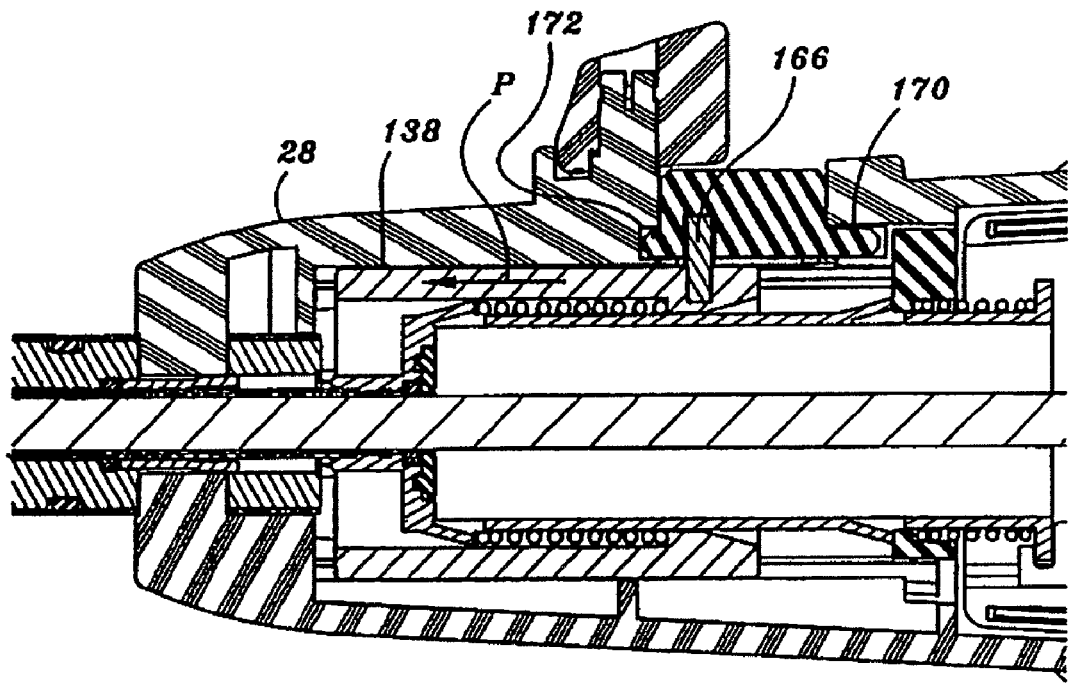
FIG. 56 is a side cross-sectional view of the articulation mechanism and rotation member of the surgical stapling apparatus shown in FIG. 1.
Figure 57:
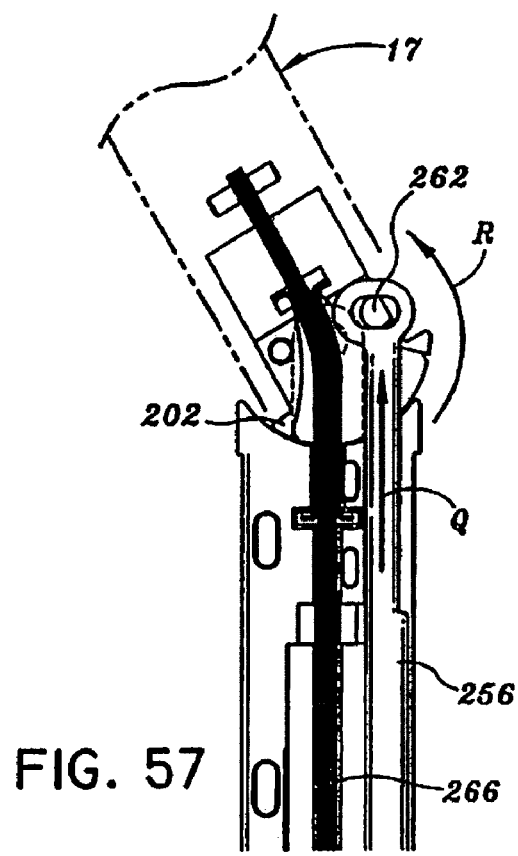
FIG. 57 is a top view of the distal end of the elongated body, the mounting assembly, and the proximal end of the tool assembly during articulation of the stapling apparatus.

Referring to FIGS. 55-61, when an articulating disposable loading unit is secured to elongated body 14 and articulation lever 30 is pivoted in the direction indicated by arrow "M" in FIG. 55, cam member 136 is moved transversely by projection 142 (FIG. 10) in the direction indicated by arrow "N" between flanges 170 and 172 of rotation knob 28. Since translation member 138 is prevented from rotating by ridges 156 (FIG. 13), pin 166, which is fixedly secured to translation member 138, is forced to move along stepped cam surface 148. Movement of pin 166 causes corresponding movement of translation member 138 in the direction indicated by arrow "P" in FIGS. 55 and 56 to advance first articulation link 123 in the distal direction. The distal end of first articulation link 123 engages the proximal end of second articulation link 256 (FIG. 42) which is connected to projection 262 on mounting assembly 202 to advance second link 256 in the direction indicated by arrow "Q" in FIG. 57. Projection 262 is laterally offset from pivot members 244, such that distal advancement of second articulation link 256 causes mounting assembly 202 and thus tool assembly 17 to pivot in the direction indicated by arrow "R" in FIGS. 57 and 58. Note in FIG. 59 that rotation member 28 can be rotated to rotate elongated body 14 about its longitudinal axis while tool assembly 17 is articulated.

Figure 60:
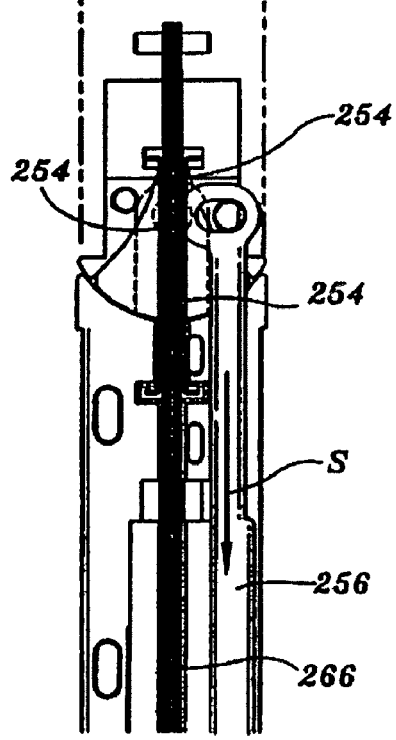
FIG. 60 is a top view of the distal end of the disposable loading unit immediately prior to articulation.
Figure 61:
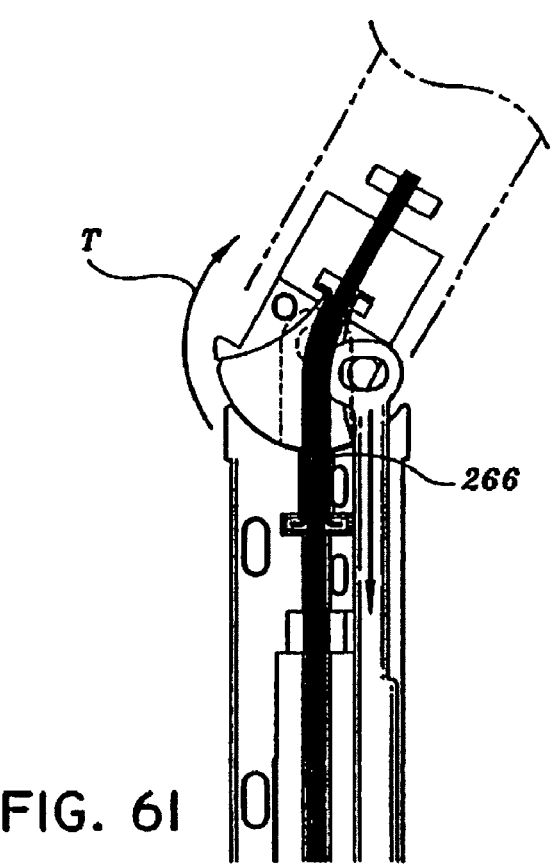
FIG. 61 is a top view of the distal end of the elongated body, the mounting assembly, and the proximal end of the tool assembly during articulation of the stapling apparatus.

FIGS. 60-61 illustrate articulation of tool assembly 17 in the opposite direction to that described above. When second articulation link 256 is retracted by rotating articulation lever 30 in a counter-clockwise direction (not shown) as viewed in FIG. 55, pin 66 is forced to move proximally along stepped camming surface 148, moving translation member 138 and first articulation link 123 proximally. Movement of first articulation link 123 proximally, causes second articulation link 256 to move proximally as indicated by arrow "S" in FIG. 58, to rotate tool assembly 17 in a clockwise direction, as indicated by arrow "T" in FIG. 61.

Referring to FIG. 12, movement of pin 166 (FIG. 9) between adjacent step portions 340 causes tool assembly 17 to articulate 22.5 degrees. Camming surface 148 includes five step portions 340. The third step portion corresponds to the non-articulated tool assembly position, whereas the first and the fifth step portions correspond to articulation of tool assembly 17 to forty-five degrees. Each step portion is flat to retain articulation lever 30 in a fixed position when pin 166 is engaged therewith.

Figure 37:
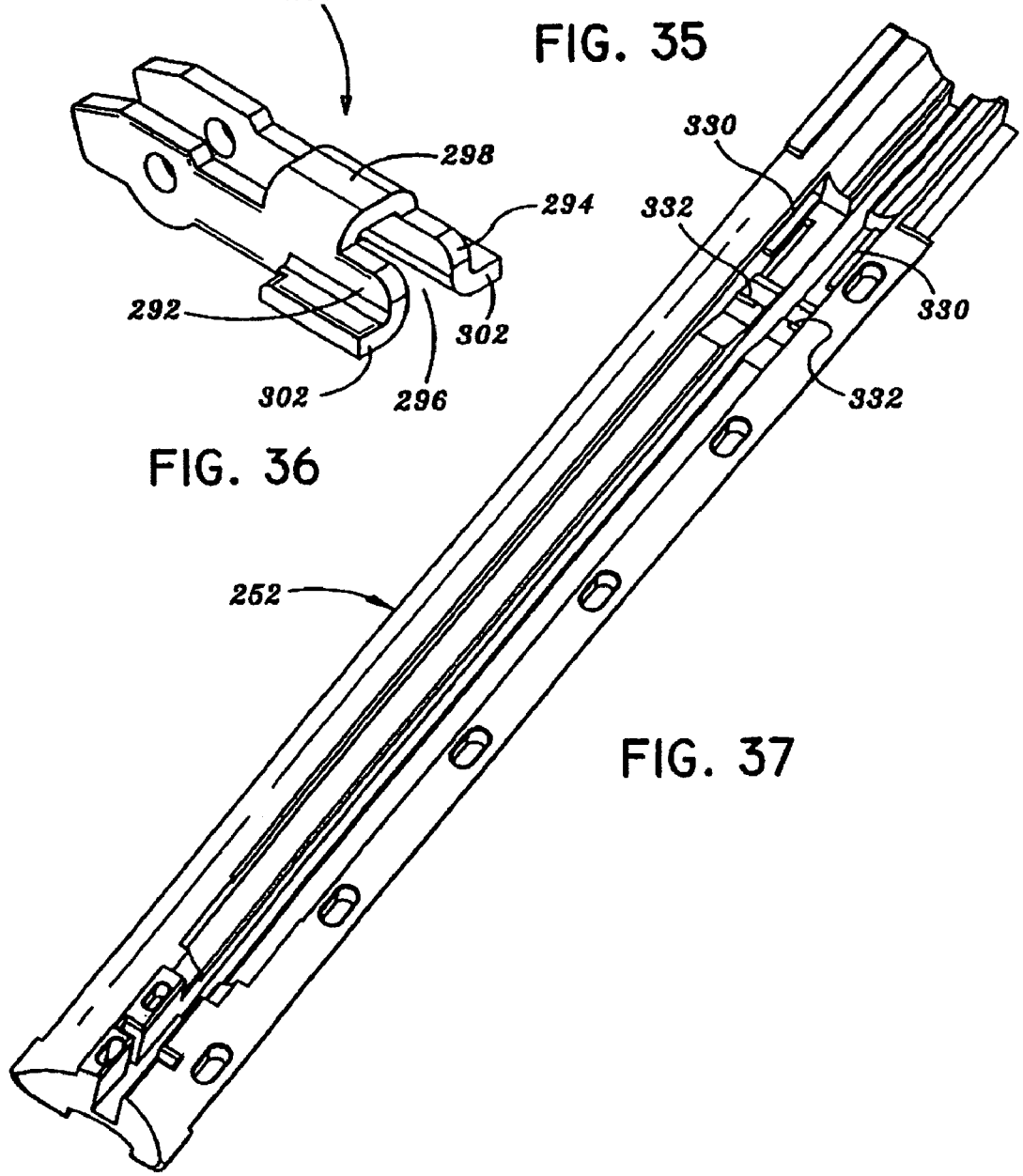
FIG. 37 is an enlarged perspective view of a lower housing half of the proximal housing portion of the disposable loading unit shown in FIG. 27.
Figure 38:
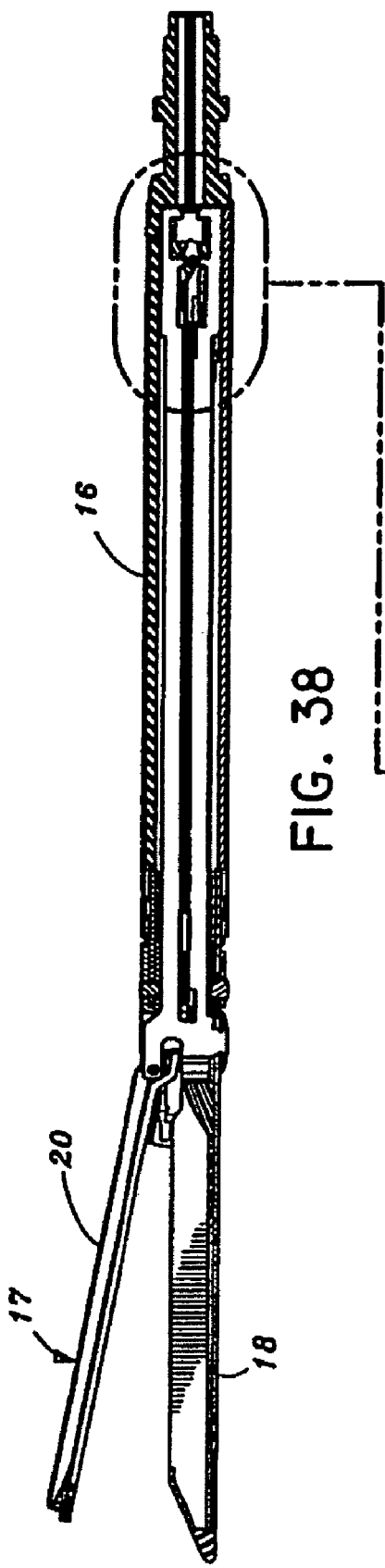
FIG. 38 is a side cross-sectional view of the disposable loading unit shown in FIG. 20.
Figure 39:
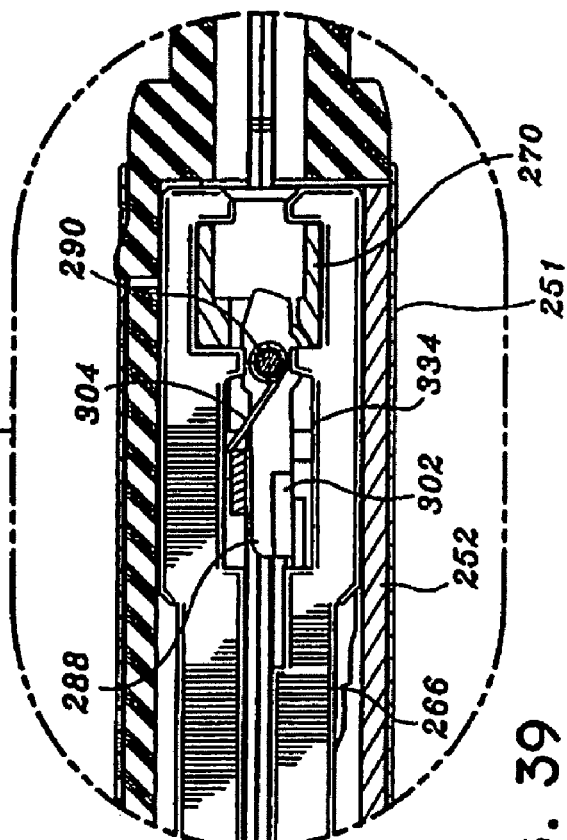
FIG. 39 is an enlarged view of the indicated area of detail shown in FIG. 38.
Figure 40:
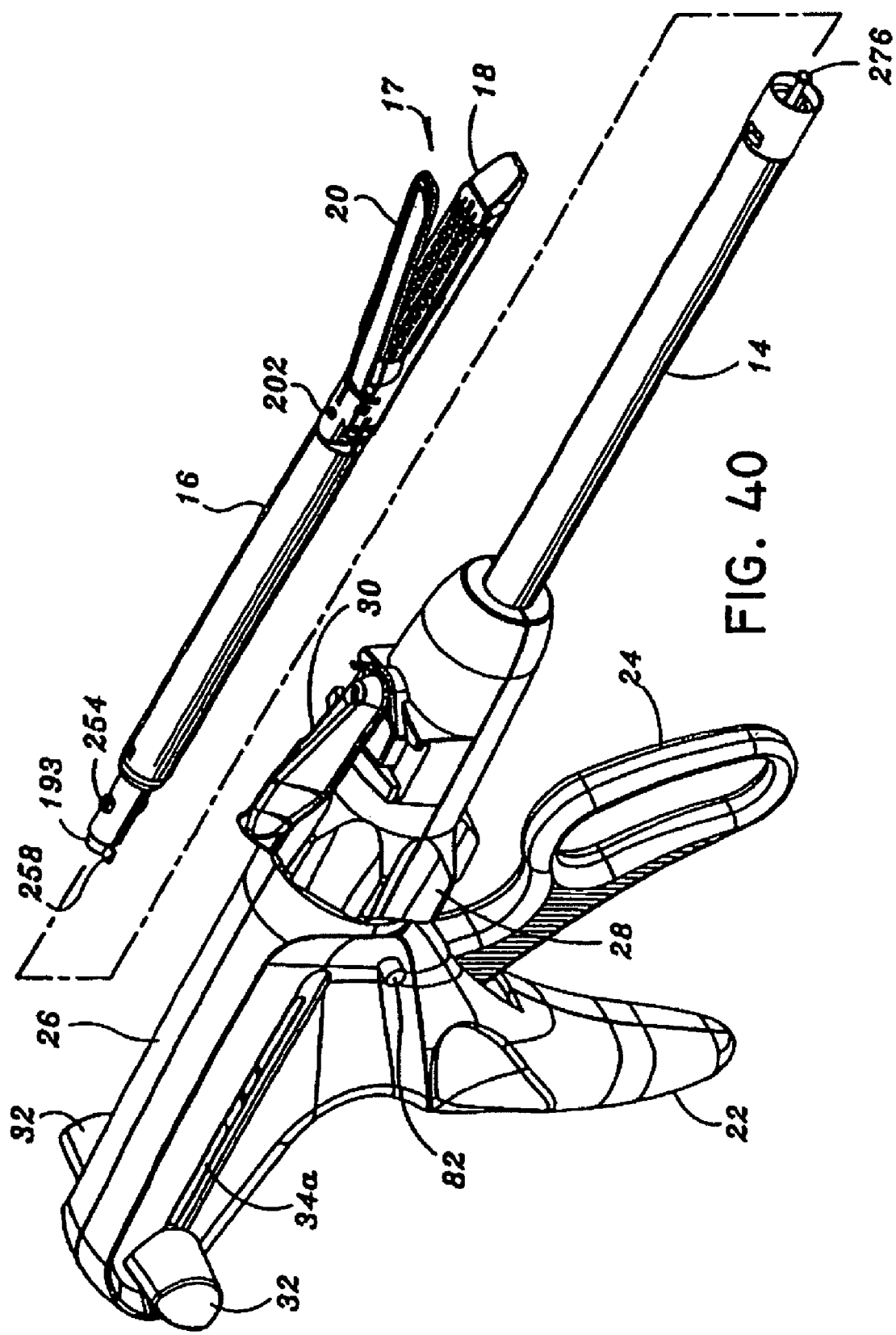
FIG. 40 is a perspective view of the surgical stapling apparatus shown in FIG. 1 with the disposable loading unit of FIG. 19 detached from the elongated body.

Referring now to FIGS. 37, 39, 62 and 63, the sequence of lockout operation will be described in detail. In FIG. 39, lockout device 288 is shown in its preferred position with horizontal cams 300 and 302 resting on top of projections 330 formed in the sidewalls of lower housing half 252 (FIG. 37). In this position, locking device 288 is held up out of alignment with projection 332 formed in the bottom surface of lower housing half 252, and web 298 is in longitudinal juxtaposition with shelf 334 defined in drive beam 266. This configuration permits the anvil 20 (FIG. 38) to be opened and repositioned onto the tissue to be stapled until the surgeon is satisfied with the position without activating locking device 288 to disable the disposable loading unit 16.

Figure 62:
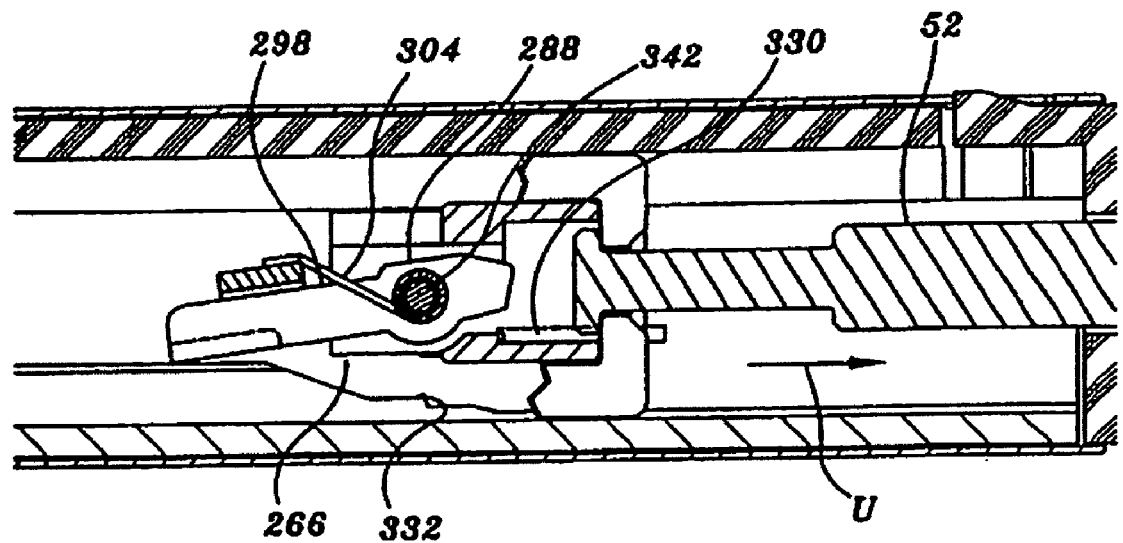
FIG. 62 is a partial cross-sectional view of a portion of the disposable loading unit during retraction of the locking device.
Figure 63:
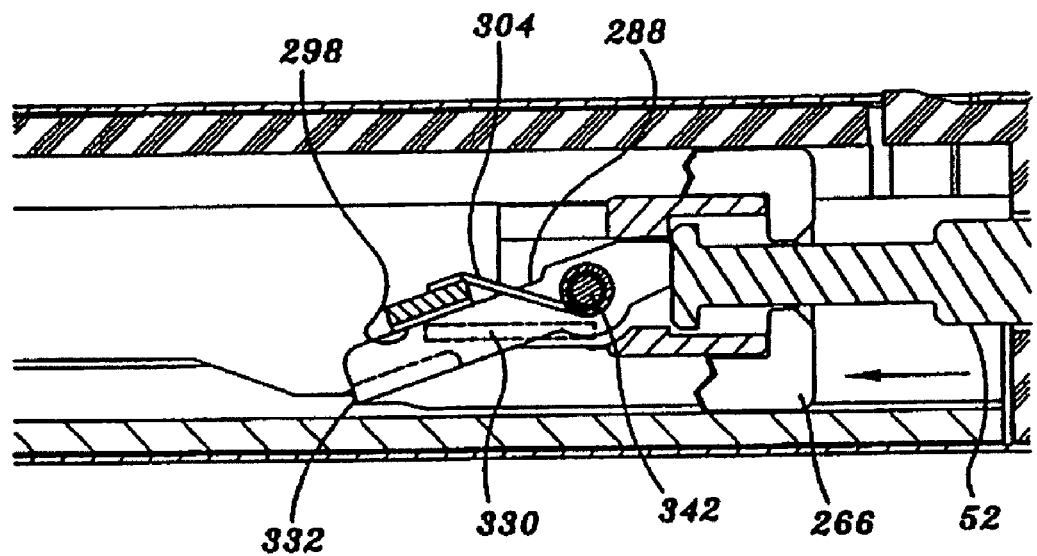
FIG. 63 is a partial cross-sectional view of a portion of the disposable loading unit with the locking device in the locked position.

As shown in FIG. 62, upon distal movement of drive beam 266, locking device 288 rides off of projections 330 (not shown) and is biased into engagement with base lower housing half 252 by spring 304, distal to projection 332. Locking device 288 remains in this configuration throughout firing of the apparatus.

Upon retraction of the drive beam 266 in the direction indicated by arrow "U" in FIG. 62, locking device 288 passes under projections 330 and rides over projection 332 until the distal most portion of locking device 288 is proximal to projection 332. Spring 304 biases locking device 288 into juxtaposed alignment with projection 332, effectively disabling the disposable loading unit. If an attempt is made to reactuate the apparatus, the control rod 52 will abut a proximal end surface of locking device 288 which surface is diagonally sloped to impart a moment about pivot pin 342 such that the distal end of locking device 288 is rotationally urged into contact with projection 332. Continued distal force in the direction indicated by arrow "W" in FIG. 63, will only serve to increase the moment applied to the locking device thus the locking device will abut projection 332 and inhibit distal movement of the control rod 52.

Referring again to FIGS. 41-44, the disabled or locked disposable loading unit can be removed from the distal end of elongated body 14 by rotating disposable loading unit 16 in the direction opposite to the direction indicated by arrow "B" in FIGS. 41, 42 and 44, to disengage hook portion 258 of second articulation link 256 from finger 164 of first articulation link 123, and to disengage nubs 254 from within channel 314 of elongated body 14. After rotation, disposable loading unit 16 can be slid in the direction opposite to that indicated by arrow "A" in FIG. 41 to detach body 14 from disposable loading unit 16. Subsequently, additional articulating and/or non-articulating disposable loading units can be secured to the distal end of elongated body, as described above, to perform additional surgical stapling and/or cutting procedures. As discussed above, each disposable loading unit may include linear rows of staples which vary from about 30 mm to about 60 mm.

It will be understood that various modifications may be made to the embodiments disclosed herein. For example, the stapling apparatus need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodi-

What is claimed is:

1. A surgical instrument comprising:
   (a) a handle assembly;
   (b) a body extending distally from the handle assembly, the body defining a first longitudinal axis;
   (c) a tool assembly pivotably supported on a distal end of the body, the tool assembly defining a second longitudinal axis, the tool assembly being pivotable from a non-articulated position in which the first longitudinal axis is aligned with the second longitudinal axis and at least one articulated position in which the second longitudinal axis is at an angle to the first longitudinal axis; and
   (d) an articulation mechanism including:
      (i) a receptacle positioned adjacent the handle assembly;
      (ii) a main shaft having base portion, the main shaft being rotatably supported within the receptacle;
      (iii) a lower clutch fixedly positioned within the receptacle, the lower clutch having a serrated portion and being positioned about the main shaft, the serrated portion including a series of shallow serrations and at least one deep serration;
      (iv) an upper clutch slidably positioned about the main shaft, the upper clutch being rotatably fixed to the main shaft such that rotation of the main shaft effects rotation of the upper clutch, the upper clutch including at least one projection positioned to engage the serrations of the lower clutch to releasably retain the main shaft at a rotatably fixed position; and
      (v) an articulation link having a proximal end operatively connected to the base portion of the main shaft and a distal end operatively connected to the tool assembly, wherein the main shaft is rotatable to move the articulation link to effect movement of the tool assembly between the non-articulated position and the at least one articulated position.

2. The surgical instrument according to claim 1, wherein the articulation mechanism further includes a substantially rigid translation member interconnecting the main shaft and the articulation link.

3. The surgical instrument according to claim 2, wherein the base portion of the main shaft includes a cam member and the translation member includes a cam slot configured to receive the cam member such that rotation of the base portion of the main shaft effects axial movement of the translation member.

4. The surgical instrument according to claim 1, wherein the articulation mechanism further includes a biasing member positioned to urge the upper clutch into the lower clutch.

5. The surgical instrument according to claim 1, wherein the at least one projection includes a plurality of projections.

6. The surgical instrument according to claim 5, wherein each of the plurality of projections has a triangularly-shaped cross-section and each of the plurality of serrations is defined by angled walls.

7. The surgical instrument according to claim 6, wherein the plurality of projections are dimensioned such that an apex of each projection is received in the shallow serrations and substantially the entire projection is received in the deep serrations.

8. The surgical instrument according to claim 1, wherein the articulation mechanism further includes an articulation lever fixedly attached to the main shaft and positioned externally of the receptacle.

9. The surgical instrument according to claim 1, further including a rotatable member rotatably supported adjacent the handle assembly, the proximal end of the body being supported by the rotatable member such that rotation of the rotatable member effects rotation of the body about the first longitudinal axis.

10. The surgical instrument according to claim 9, wherein the receptacle is formed in the rotatable member.

11. The surgical instrument according to claim 1, wherein the body is elongated.

12. The surgical instrument according to claim 1, wherein the at least one projection is positioned to be received within the at least one deep serration when the tool assembly is in the non-articulated position.

13. The surgical instrument according to claim 12, wherein the at least one deep serration includes three deep serrations and the at least one projection includes three projections.

14. The surgical instrument according to claim 1, wherein the tool assembly includes an anvil assembly and a staple cartridge.

* * * * *